United States Patent
Wang

(10) Patent No.: US 11,267,815 B2
(45) Date of Patent: Mar. 8, 2022

(54) CLASS OF AMINO-SUBSTITUTED NITROGEN-CONTAINING FUSED RING COMPOUNDS, PREPARATION METHOD THEREFOR, AND USE THEREOF

(71) Applicant: SHANGHAI RINGENE BIOPHARMA CO., LTD., Shanghai (CN)

(72) Inventor: Hui Wang, Nantong (CN)

(73) Assignee: SHANGHAI RINGENE BIOPHARMA CO., LTD., Shanghai (CN)

( * ) Notice: Subject to any disclaimer, the term of this patent is extended or adjusted under 35 U.S.C. 154(b) by 46 days.

(21) Appl. No.: 16/760,005

(22) PCT Filed: Oct. 30, 2018

(86) PCT No.: PCT/CN2018/112661
§ 371 (c)(1),
(2) Date: Apr. 28, 2020

(87) PCT Pub. No.: WO2019/085895
PCT Pub. Date: May 9, 2019

(65) Prior Publication Data
US 2020/0347061 A1    Nov. 5, 2020

(30) Foreign Application Priority Data
Oct. 30, 2017    (CN) .......................... 201711039980.6

(51) Int. Cl.
C07D 471/14      (2006.01)
A61K 31/496     (2006.01)
A61P 35/00       (2006.01)

(52) U.S. Cl.
CPC ............ *C07D 471/14* (2013.01); *A61P 35/00* (2018.01)

(58) Field of Classification Search
CPC .. C07D 471/14; C07D 265/30; A61K 31/496; A61K 31/519; A61K 31/4375; A61P 35/00
USPC ...... 544/251, 361; 546/82; 514/252.16, 257, 514/293
See application file for complete search history.

(56) References Cited

U.S. PATENT DOCUMENTS

| | | |
|---|---|---|
| 6,949,560 B2 | 9/2005 | Goldstein |
| 2016/0332971 A1 | 11/2016 | Watt et al. |
| 2021/0130353 A1 | 5/2021 | Xu et al. |

FOREIGN PATENT DOCUMENTS

| | | |
|---|---|---|
| CN | 105481858 A | 4/2010 |
| CN | 106588920 A | 4/2017 |
| EP | 3587419 A1 | 1/2020 |
| WO | 2016134294 A1 | 8/2016 |
| WO | 2018153373 A1 | 8/2018 |

OTHER PUBLICATIONS

Chinese Office Action issued in Chinese Patent Application No. 201811276459.9, dated Jul. 9, 2020.
International Search Report issued in International Patent Application No. PCT/CN2018/112661 dated Feb. 2, 2019.
Written Opinion of the International Searching Authority issued in International Patent Application No. PCT/CN2018/112661 dated Feb. 2, 2019.
First Office Action of corresponding Japanese application JP2020-544089 dated May 11, 2021.
EESR of corresponding EP application 18874000.5 dated Jun. 21, 2021.
Tao Yu et al"A FGFR1 inhibitor patent review: progress since 2010", Expert Opinion on Therapeutic Patents, Dec. 26, 2016 Dec. 16, 2016), pp. 1-16.
Japanese Second Office Action issued in Japanese Patent Application No. 2020-544089 dated Sep. 28, 2021.
Korean First Office Action issued in Korean Patent Application No. 10-2020-7015596 dated Nov. 23, 2021.

*Primary Examiner* — Charanjit Aulakh
(74) *Attorney, Agent, or Firm* — SZDC Law P.C.

(57) ABSTRACT

The present invention discloses a class of amino-substituted nitrogen-containing fused ring compounds, a preparation method therefor, and a use thereof. The structure of the amino-substituted nitrogen-containing fused ring compounds of the present invention is as shown in formula (I) below, and each group therein is as defined in the specification. The amino-substituted nitrogen-containing fused ring compounds of the present invention are novel specific FGFR kinase inhibitors, having excellent inhibitory activity for FGFR-related tumor cell proliferation, and is applicable to the treatment of diseases such as tumors associated with FGFR kinase mutations or abnormal expressions.

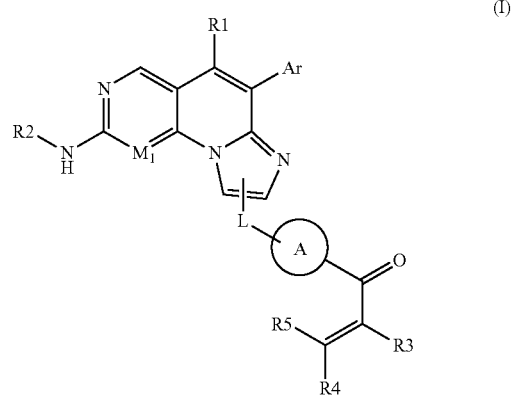

17 Claims, No Drawings

CLASS OF AMINO-SUBSTITUTED NITROGEN-CONTAINING FUSED RING COMPOUNDS, PREPARATION METHOD THEREFOR, AND USE THEREOF

This application is the national stage application of PCT/CN2018/112661, filed on Oct. 30, 2018, which claims the benefit of Chinese patent application CN201711039980.6 filed on Oct. 30, 2017, the content of which is incorporated herein by reference in its entirety.

FIELD OF THE INVENTION

The present disclosure relates to pharmaceutical chemistry field, and particularly relates to a class of amino-substituted nitrogen-containing fused ring compounds, a preparation method thereof and a use thereof.

BACKGROUND OF THE INVENTION

Abnormal expression and activation or gene mutation of receptor tyrosine kinase play a key role in tumorigenesis, development, invasion and metastasis and drug resistance etc., thus it becomes an important target for anti-tumor drug research and development. Among them, fibroblast growth factor receptor (FGFR) is an important member of tyrosine kinase family, mainly including four subtypes i.e., FGFR1, FGFR2, FGFR3 and FGFR4. Due to gene amplification, mutation, fusion or ligand induction, each of FGFR members continues to be activated, inducing tumor cell proliferation and invasion, promoting angiogenesis and tumor deterioration. FGFRs are highly expressed and abnormally activated in various tumors, and closely related to the poor prognosis of tumor patients. Therefore, FGFRs are recognized as important anti-tumor targets, and the research and development of small molecule FGFR inhibitors has gradually received more and more attention.

Clinically, many cancers such as hepatocellular carcinoma, gastric cancer, pancreatic cancer, bile duct cancer and other malignant tumors are accompanied by overexpression and overactivation of FGFR gene in tumor tissues. Therefore, specifically targeting fibroblast growth factor receptor FGFR is likely to become a new strategy for the treatment of various tumors, especially liver, bile duct cell cancer etc., which has attracted extensive attention of large pharmaceutical companies in recent years.

CONTENT OF THE INVENTION

The technical problem to be solved by the present disclosure is to develop more small molecule FGFR inhibitors, thereby providing a class of amino-substituted nitrogen-containing fused ring compounds, a preparation method therefor and a use thereof. The amino-substituted nitrogen-containing fused ring compounds of the present disclosure are novel specific FGFR kinase inhibitors and have excellent inhibitory activity on FGFR-related tumor cell proliferation, thus the compounds are useful for the treatment of diseases induced by abnormal FGFR kinase such tumors.

The present disclosure solves the above technical problem through the following technical solutions.

The present disclosure provides a compound represented by formula (I), or a pharmaceutically acceptable salt thereof, or an enantiomer, diastereomer, tautomer, solvate, polymorph or prodrug thereof,

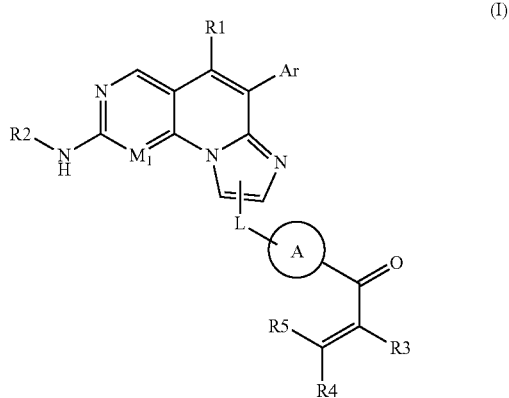

wherein:
$R_1$ is selected from hydrogen, halogen, $C_1$-$C_3$ alkyl, cyano; and $R_1$ is preferably selected from hydrogen, halogen, methyl;
$R_2$ is selected from hydrogen, $C_1$-$C_{10}$ alkyl, 3-8 membered cycloalkyl or heterocycloalkyl, 5-8 membered aryl or heteroaryl; and $R_2$ is preferably selected from hydrogen, alkyl unsubstituted or substituted by $C_1$-$C_6$;
each of $R_3$, $R_4$ and $R_5$ is independently selected from hydrogen, halogen, cyano, alkyl, sulfuryl, sulfinyl, acyl, sulfonyl, nitro; and each of $R_3$, $R_4$ and $R_5$ is preferably selected from hydrogen, halogen, methyl;
$M_1$ is selected from $CR_6$ or N; $R_6$ is selected from hydrogen, halogen, $C_1$-$C_3$ alkyl;
Ar is selected from 5-6 membered aryl or heteroaryl;
L is selected from a chemical bond, $C_1$-$C_{10}$ alkyl, alkenyl, alkynyl, alkoxyl, alkylthio, alkylamino, acyl, sulfonyl, 4-8 membered cycloalkyl or heterocycloalkyl, 5-10 membered aryl or heteroaryl; and L is preferably selected from $C_1$-$C_6$ alkyl;
A is selected from 4-8 membered cycloalkyl or heterocycloalkyl, 5-10 membered aryl or heteroaryl; and A is preferably selected from 5-6 membered heterocycloalkyl, 5-6 membered aryl or heteroaryl;
one or more hydrogen atoms in each of the above groups are optionally substituted by the substituent selected from the group consisting of deuterium, halogen, hydroxyl, amino, cyano, sulfuryl or sulfinyl, $C_1$-$C_8$ alkyl, $C_3$-$C_8$ cycloalkyl, $C_1$-$C_8$ alkoxyl, $C_1$-$C_8$ alkylamino, $C_2$-$C_6$ alkenyl, $C_2$-$C_6$ alkynyl, $C_2$-$C_6$ acyl or sulfonyl, 5-8 membered aryl or heteroaryl, 4-8 membered saturated cycloalkyl or heterocycloalkyl; wherein, the heteroaryl comprises 1-3 heteroatoms selected from the group consisting of N, O, P and S; the heterocycloalkyl comprises 1-3 heteroatoms selected from the group consisting of N, O, P and S.

Each of the ring systems in the above definitions is independently selected from monocyclic ring, fused ring, condensed ring, bridged ring or spiro ring; the heteroaryl can be partially oxidized and/or reduced.

Furthermore, the compound represented by formula (I), or the pharmaceutically acceptable salt thereof, or the enantiomer, diastereomer, tautomer, solvate, polymorph or prodrug thereof of the present disclosure,
in the formula,
$M_1$ is preferably selected from CH or N;
$R_1$ is preferably selected from hydrogen, halogen (e.g., fluorine), $C_1$-$C_3$ alkyl (e.g., methyl);
$R_2$ is preferably selected from hydrogen, $C_1$-$C_6$ alkyl (e.g., methyl), $C_1$-$C_6$ deuterated alkyl (e.g., —$CD_3$), $C_1$-$C_6$ haloalkyl (e.g., —CH$_2$C(CH$_3$)$_2$F), 5-8 membered aryl or heteroaryl, 4-6 membered cycloalkyl or heterocycloalkyl-(CH$_2$)x-, O(R$_6$)—(CH$_2$)y-, N(R$_7$)(R$_8$)—(CH$_2$)z-, N(CH$_3$)$_2$C(=O)CH$_2$—, HOC(CH$_3$)$_2$CH— or CH(CH$_2$OH)$_2$—CH$_2$—; wherein, the 5-8 membered aryl or heteroaryl is preferably pyridinyl, and preferably further substituted by one 6 membered heterocycloalkyl (e.g., N-methylpiperazinyl); the 4-6 membered cycloalkyl or heterocycloalkyl is preferably selected from cyclopropyl, tetrahydrofuryl, piperazinyl, piperidinyl or tetrahydropyrrolyl, and preferably further substituted by C$_1$-C$_6$ alkyl (e.g., methyl) or amino; each of R$_6$, R$_7$ and R$_8$ is independently selected from hydrogen or C$_1$-C$_6$ alkyl (e.g., methyl); each of x, y and z is independently selected from 0, 1, 2, 3 or 4;

more preferably, R$_2$ is selected from H, methyl, —CD$_3$, —CH$_2$C(CH$_3$)$_2$F, N(CH$_3$)$_2$C(=O)CH$_2$—, HOC(CH$_3$)$_2$CH—, CH(CH$_2$OH)$_2$—CH$_2$—,

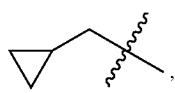

CH$_3$OCH$_2$CH$_2$—,

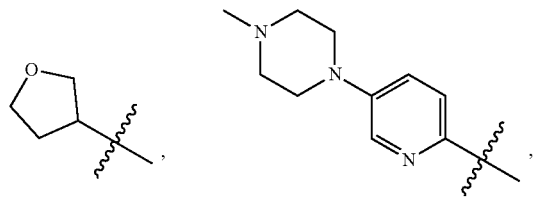

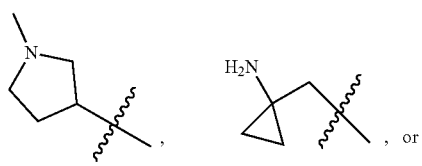

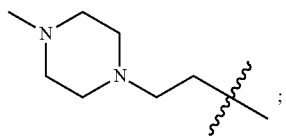

each of R$_3$, R$_4$ and R$_5$ is preferably independently selected from hydrogen, halogen (e.g., fluorine) or N(R$_9$)(R$_{10}$)—(CH$_2$)p- (wherein R$_9$ and R$_{10}$ are both C$_1$-C$_6$ alkyl, p is selected from 0, 1 or 2; e.g., N(R$_9$)(R$_{10}$)—(CH$_2$)p- is dimethylaminomethylene); more preferably, R$_3$ is selected from hydrogen or fluorine, and R$_4$ and R$_5$ are hydrogen;

Ar is preferably selected from 6 membered aryl, i.e., phenyl, more preferably, one or more (e.g., one, two, three or four) hydrogen atoms in the phenyl are substituted by the substituent selected from halogen, cyano, C$_1$-C$_8$ alkyl, C$_1$-C$_8$ alkoxyl, amino, hydroxyl, C$_2$-C$_6$ acyl or sulfonyl (more preferably the substituent is selected from halogen or C$_1$-C$_8$ alkoxyl); and more preferably substituted by two halogens (e.g., fluorine or chlorine) and two C$_1$-C$_8$ alkoxyls (e.g., methoxyl), e.g.,

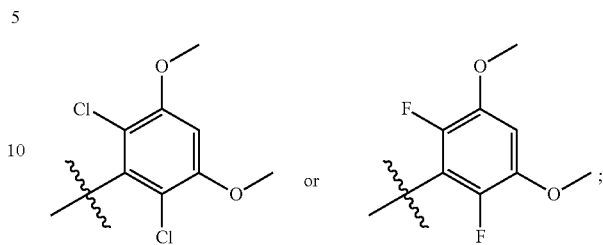

L is preferably a chemical bond, —(CH$_2$)$_d$— (wherein d is 1, 2 or 3, e.g., —CH$_2$—, —CH$_2$CH$_2$— or —CH$_2$CH$_2$CH$_2$—), —(CH$_2$)$_e$—CH=CH— (wherein e is 1 or 2, e.g., —CH$_2$—CH=CH—, and preferably the C$_{sp3}$ carbon atom contained therein is attached to ring A), or —O—(CH$_2$)$_n$— (wherein n is 1, 2, 3 or 4, e.g., —O—CH$_2$CH$_2$—, and preferably the oxygen atom contained therein is attached to ring A);

A is preferably selected from 5-6 membered heterocycloalkyl (the 5-6 membered heterocycloalkyl is further preferably piperazinyl, piperidinyl or tetrahydropyrrolyl), 5-6 membered heteroaryl-NH— (the 5-6 membered heteroaryl is further preferably pyridinyl, oxazolyl or triazolyl), -Ph-(CH$_2$)$_o$—NH— (wherein o is selected from 0 or 1), 5-6 membered heteroaryl-(CH$_2$)$_m$-5-6 membered heterocycloalkyl- (wherein the 5-6 membered heterocycloalkyl is more preferably piperazinyl, piperidinyl or tetrahydropyrrolyl, the 5-6 membered heteroaryl is more preferably pyridinyl, oxazolyl or triazolyl, m is selected from 0 or 1); and, the two substituents on A are preferably located in meta or para-position with respect to each other;

more preferably, A is a structural fragment selected from:

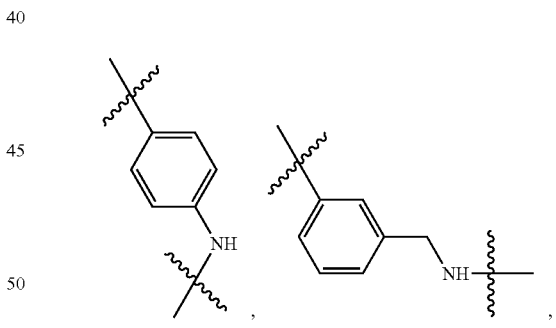

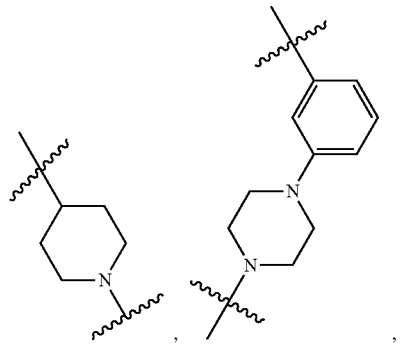

-continued

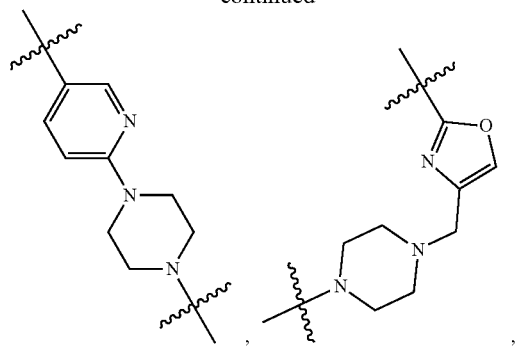,

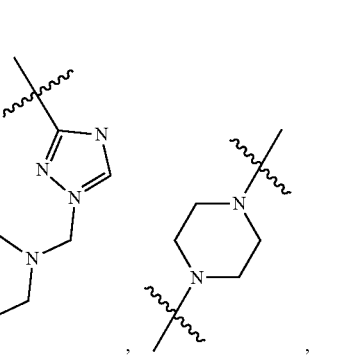,

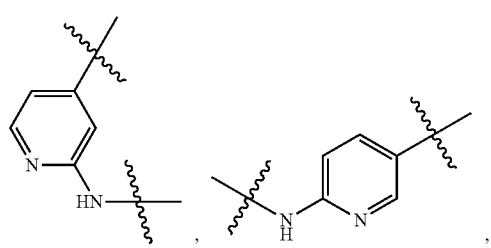,

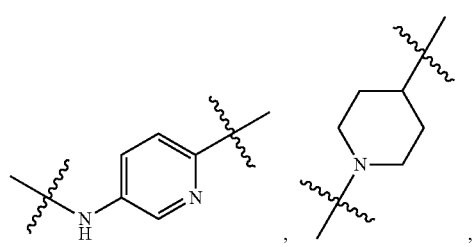,

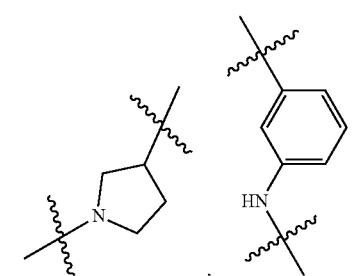.

wherein, L is invariably connected to the side of aryl, heteroaryl or non-fatty amino in the structure of A.

Furthermore, the compound represented by formula (I), or the pharmaceutically acceptable salt thereof, or the enantiomer, diastereomer, tautomer, solvate, polymorph or prodrug thereof of the present disclosure, wherein the compound represented by formula (I) has a structure selected from

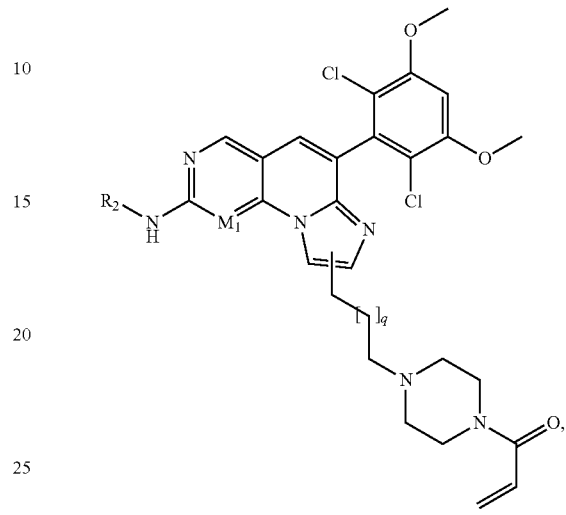,

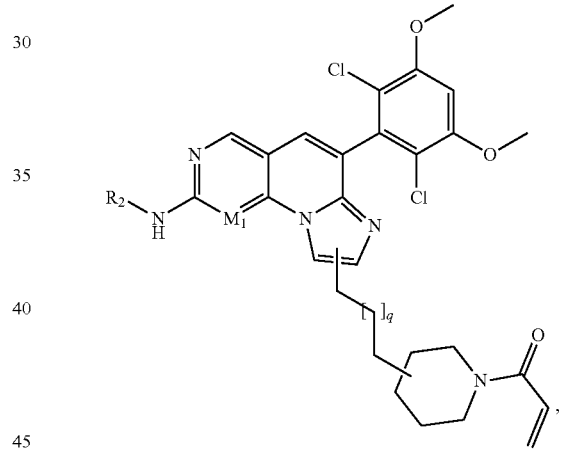,

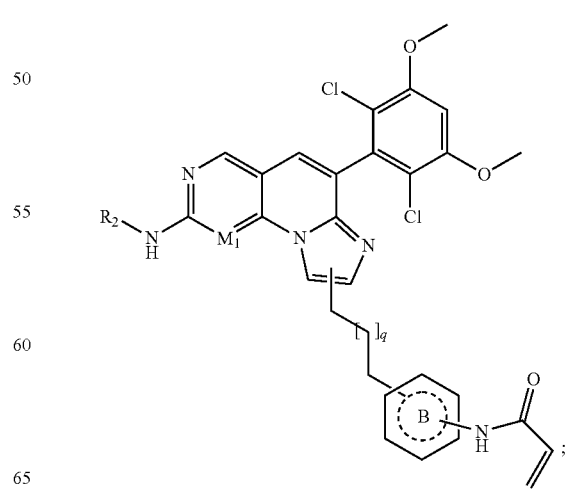;

more preferably selected from

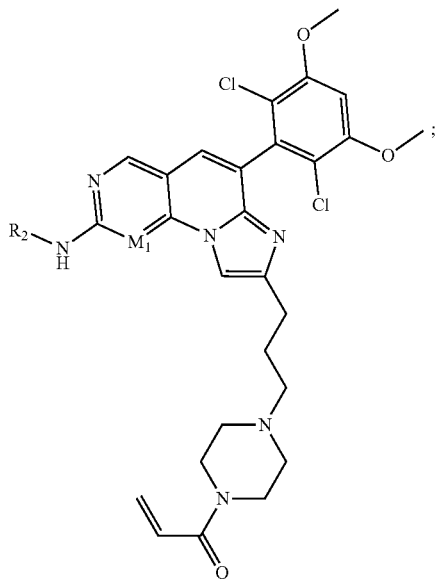

wherein, n is selected from 0, 1 or 2, $M_1$ and $R_2$ are as defined above; ring B is a 5-10 membered aromatic ring or aromatic heterocyclic ring; preferably benzene ring, pyridine ring, oxazole ring or triazole ring.

Furthermore, the compound represented by formula (I), or the pharmaceutically acceptable salt thereof, or the enantiomer, diastereomer, tautomer, solvate, polymorph or prodrug thereof of the present disclosure, wherein the compound represented by formula (I) has a structure selected from:

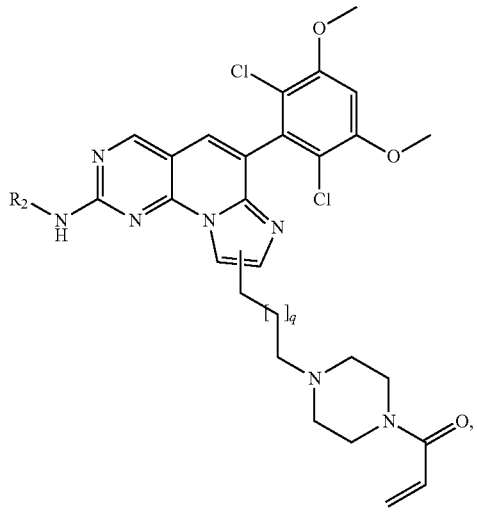

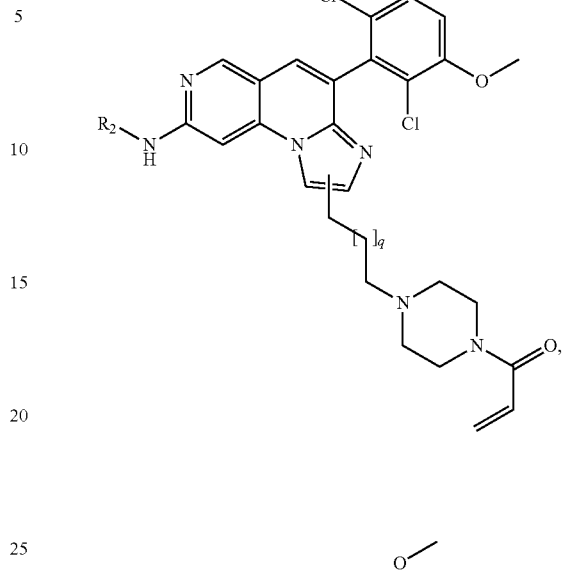

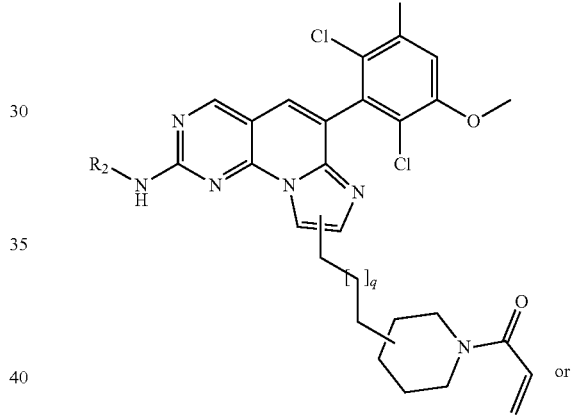

or

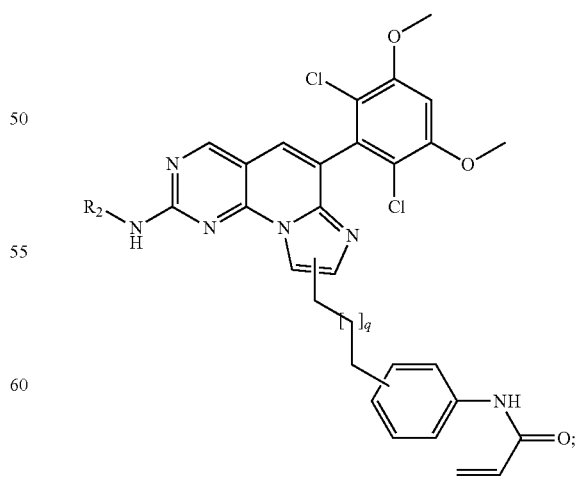

wherein, n is selected from 0, 1 or 2, $R_2$ is as defined above.

more preferably selected from
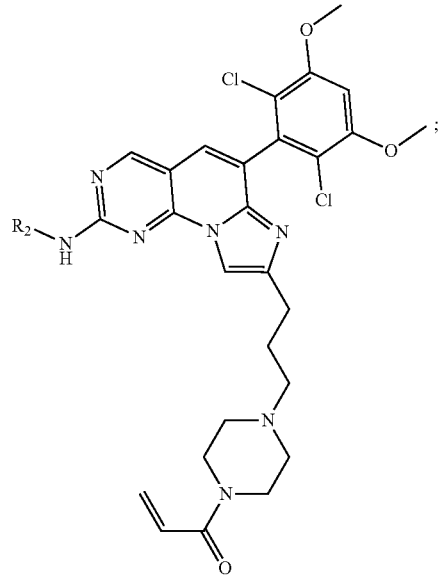
wherein, R₂ is as defined above.
Furthermore, the compound represented by formula (I), or the pharmaceutically acceptable salt thereof, or the enantiomer, diastereomer, tautomer, solvate, polymorph or prodrug thereof of the present disclosure, wherein the compound represented by formula (I) is any one of the compounds as follows:
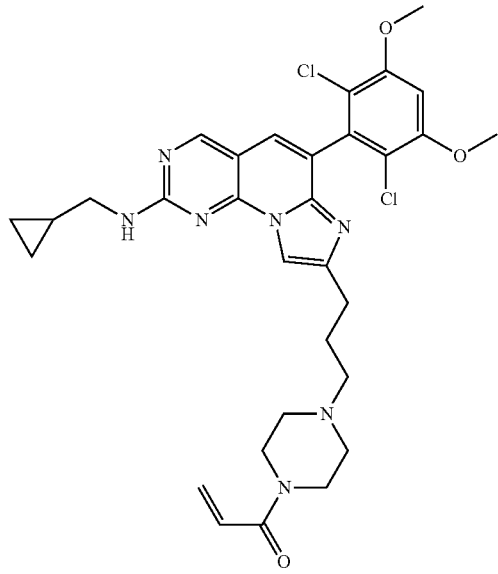
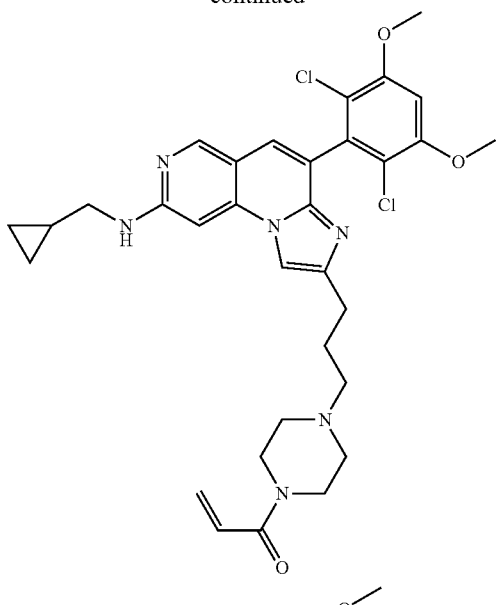
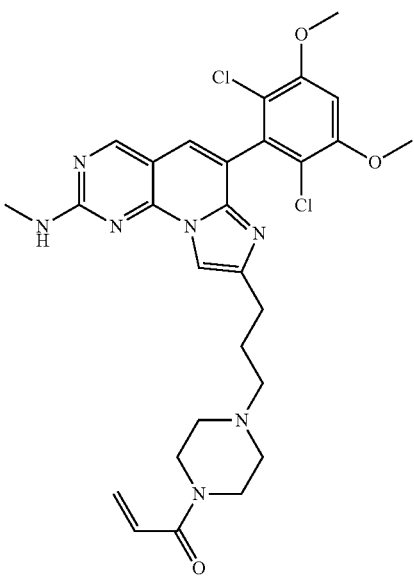
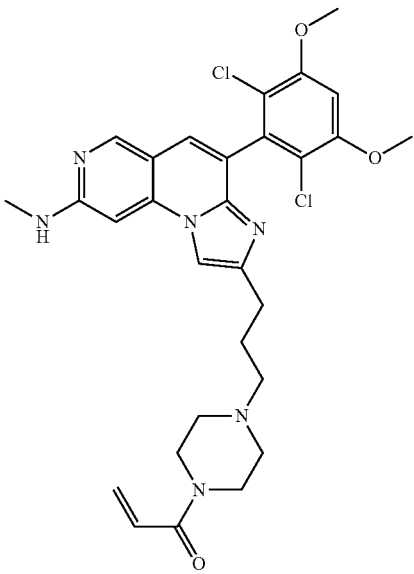

11
-continued
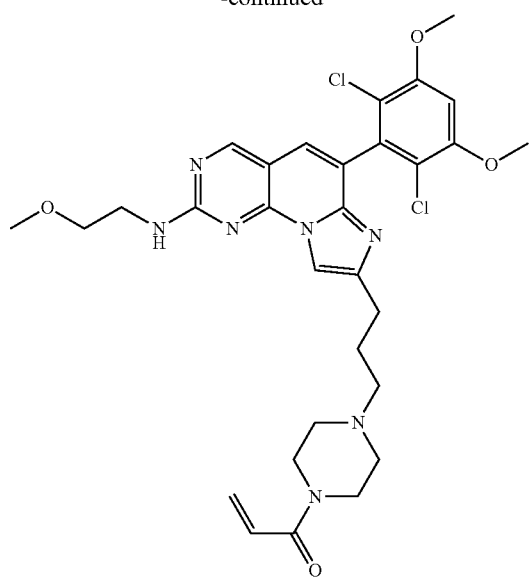
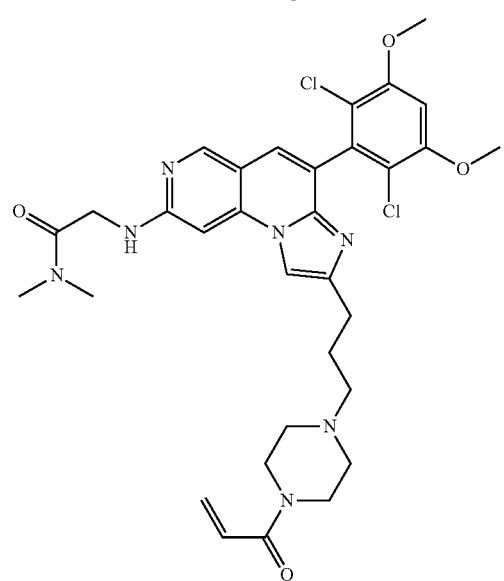
12
-continued
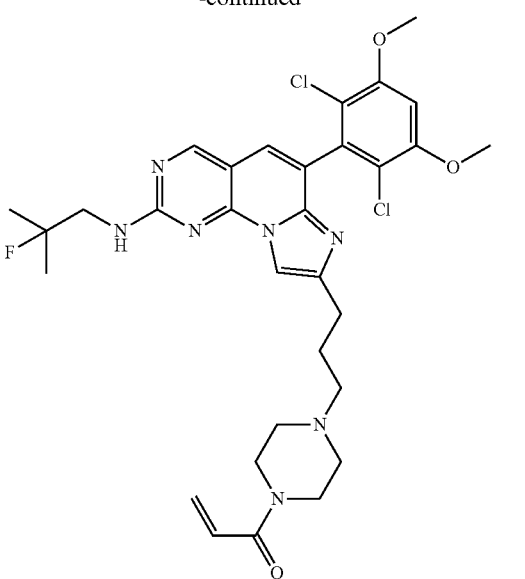
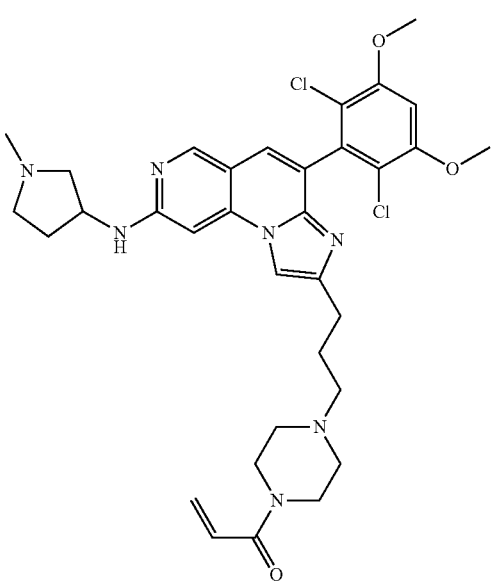

13
-continued
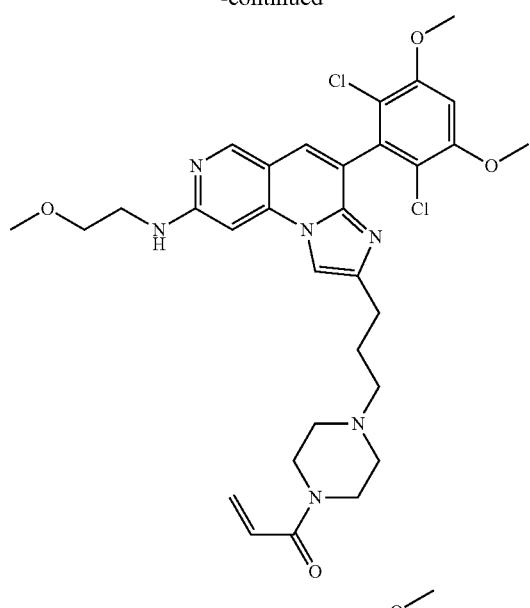
14
-continued
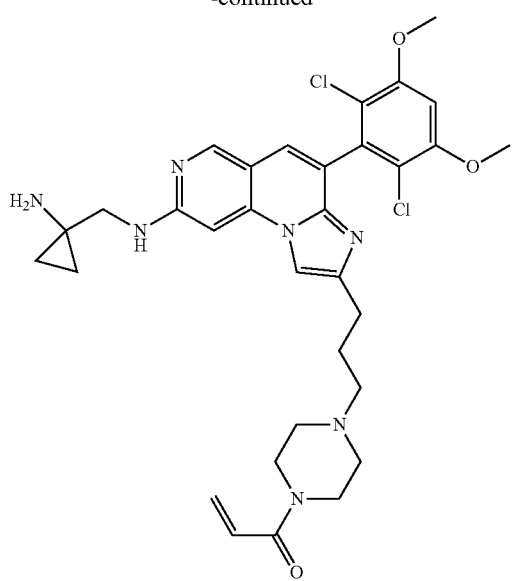
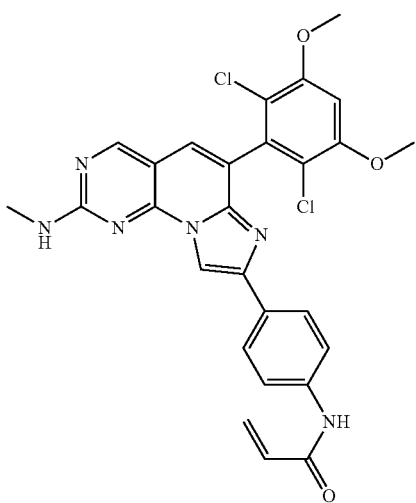
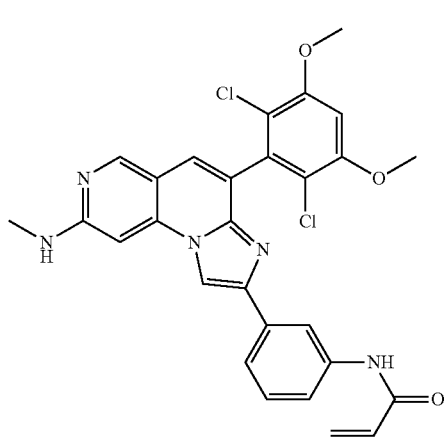

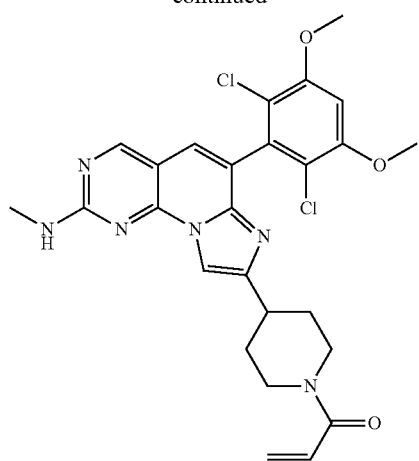
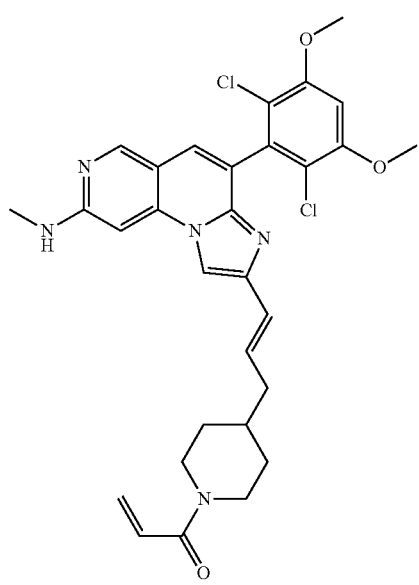
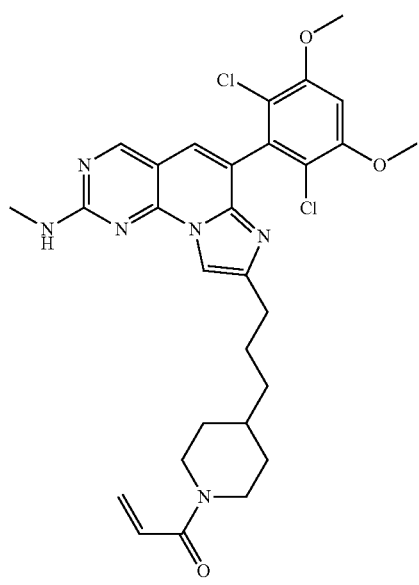
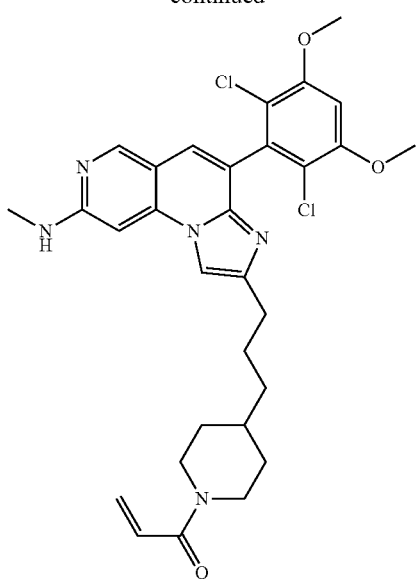
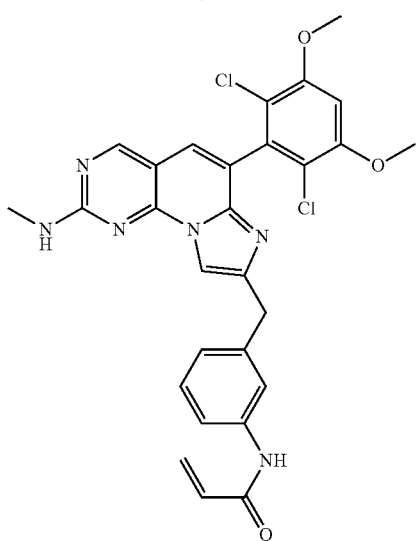
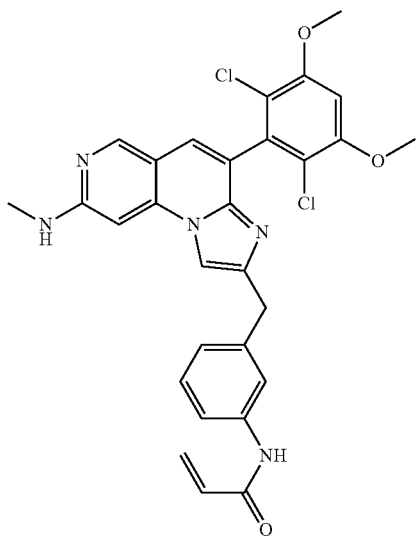

17
-continued
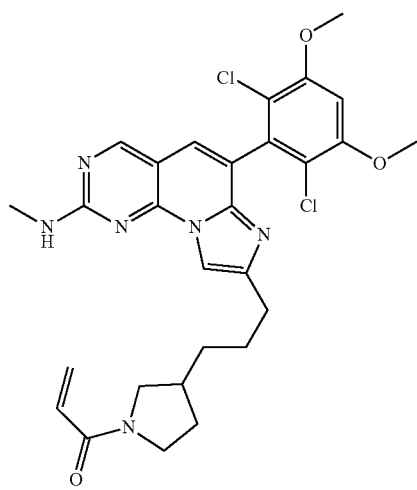
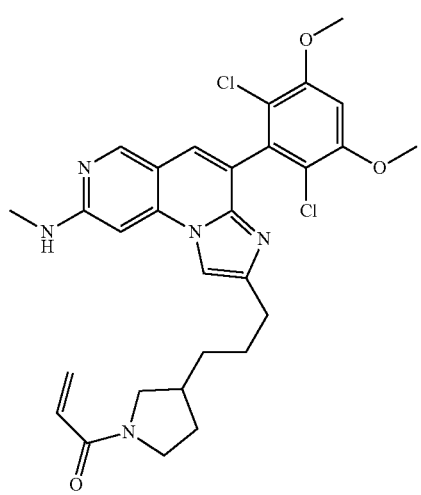
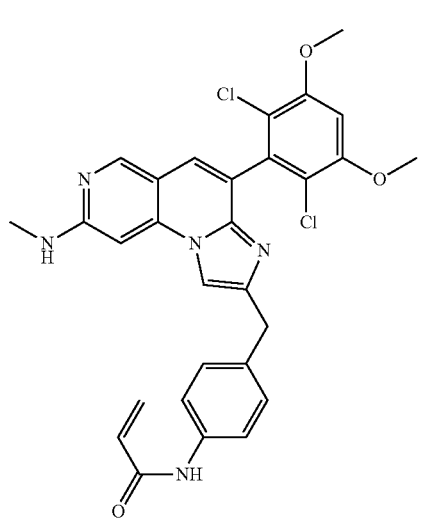
18
-continued
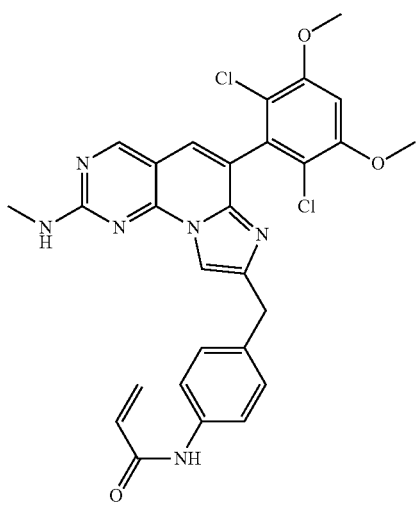
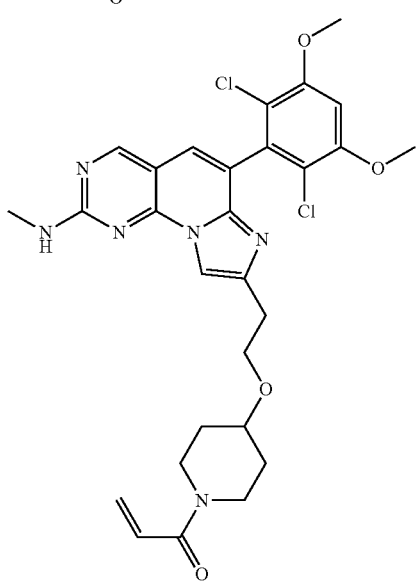
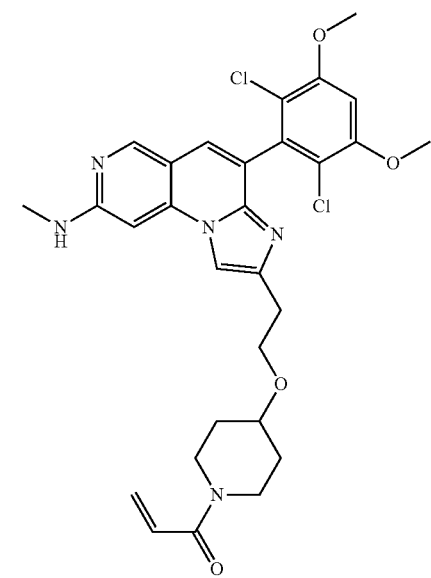

-continued
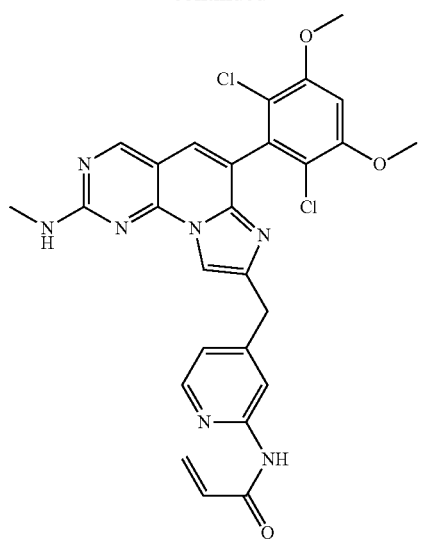
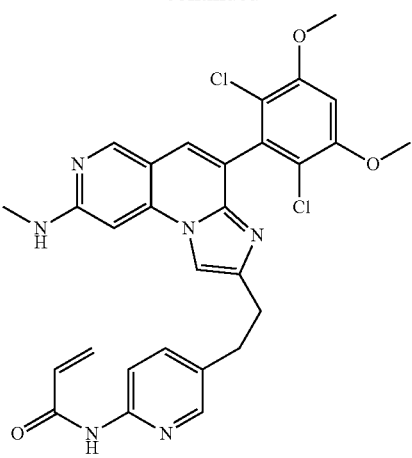
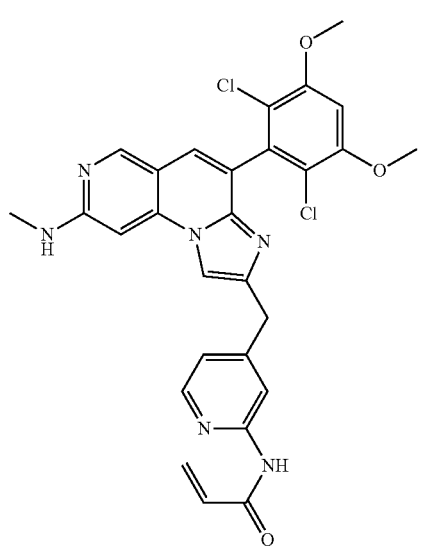
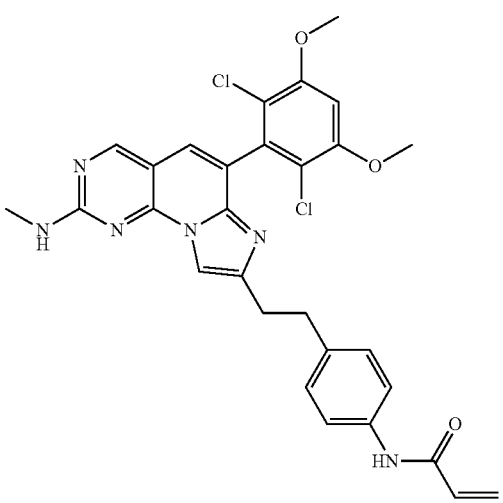
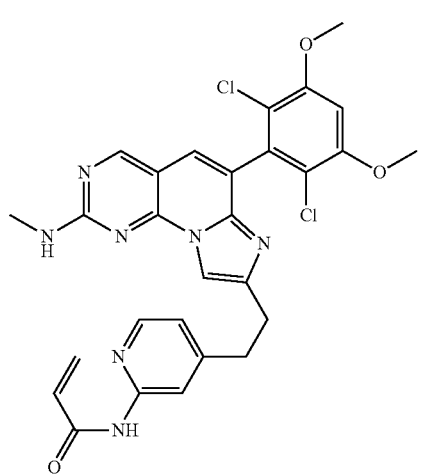
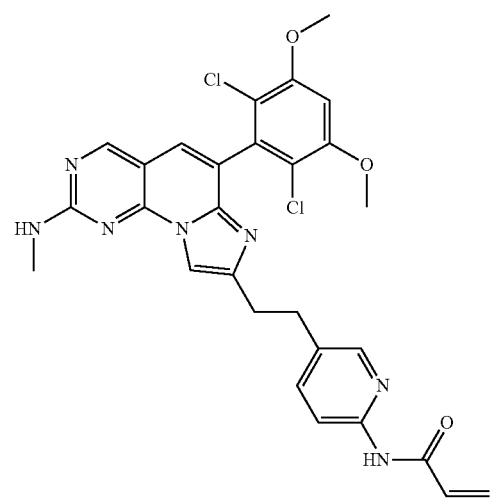

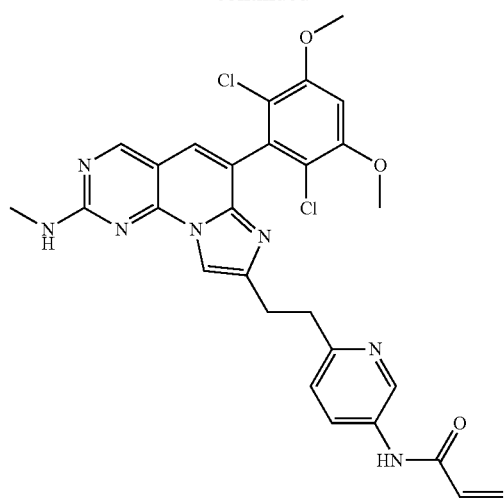
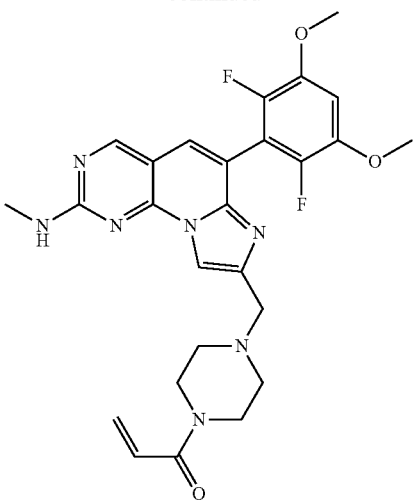
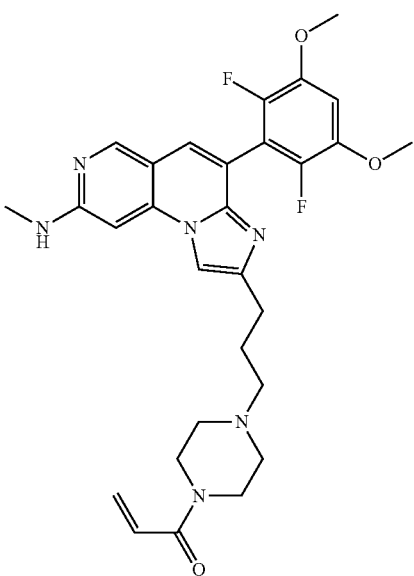
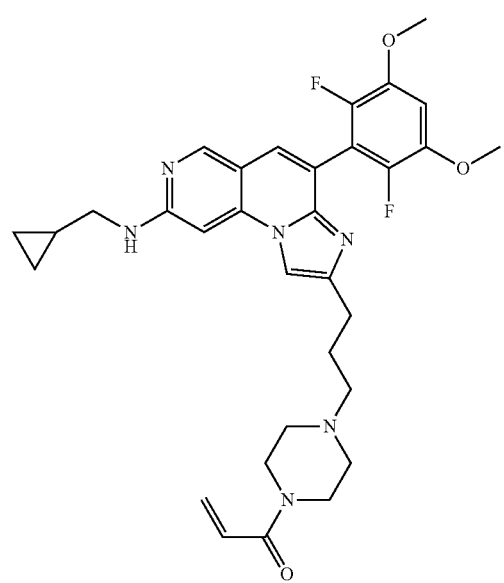
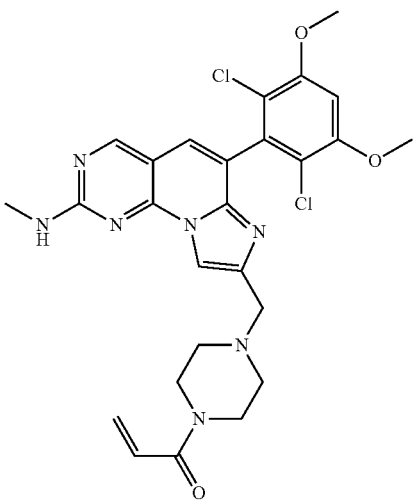

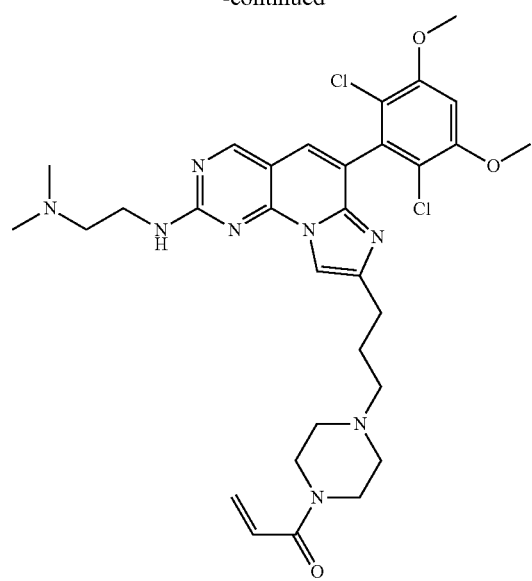
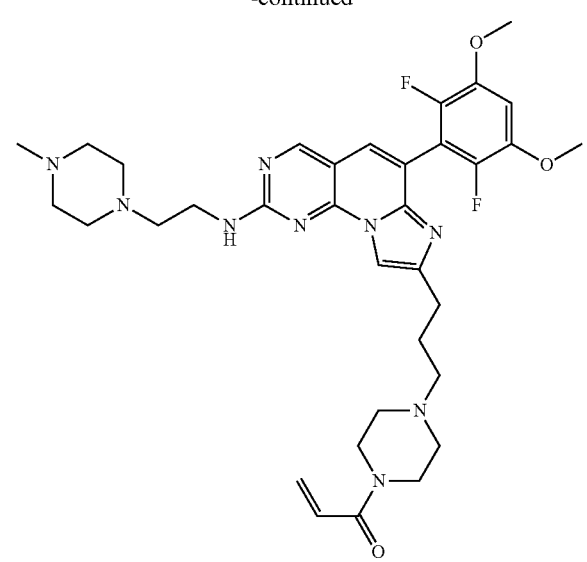
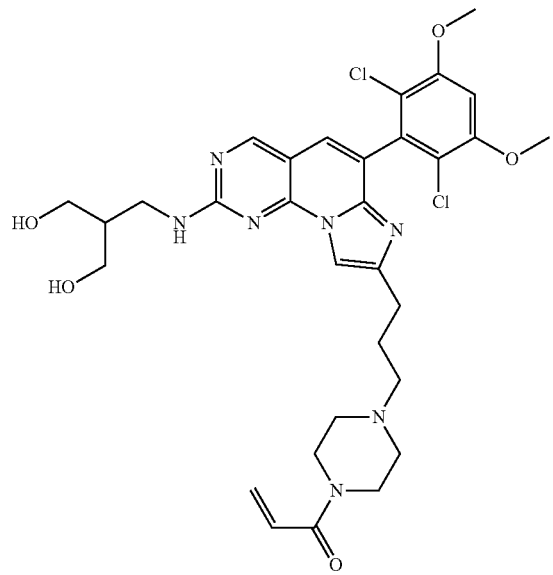
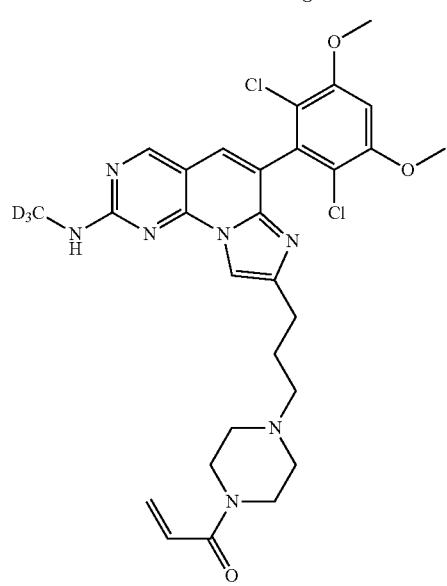
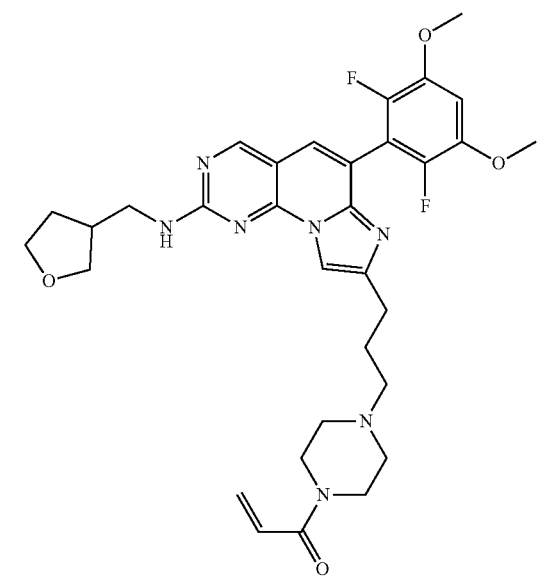
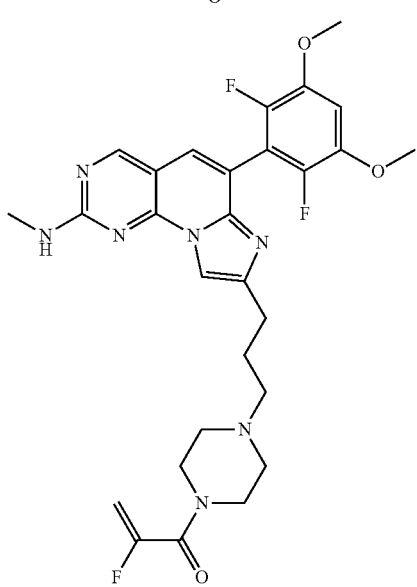

25
-continued
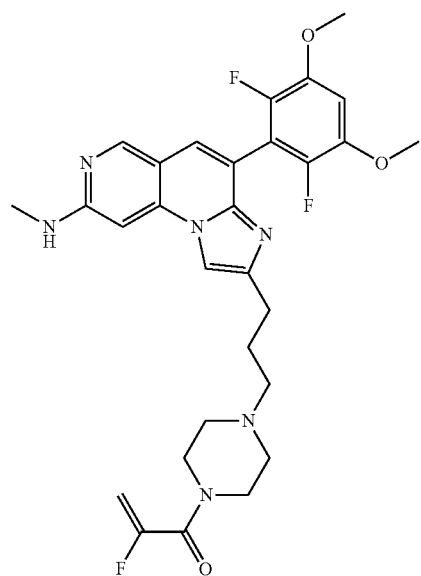
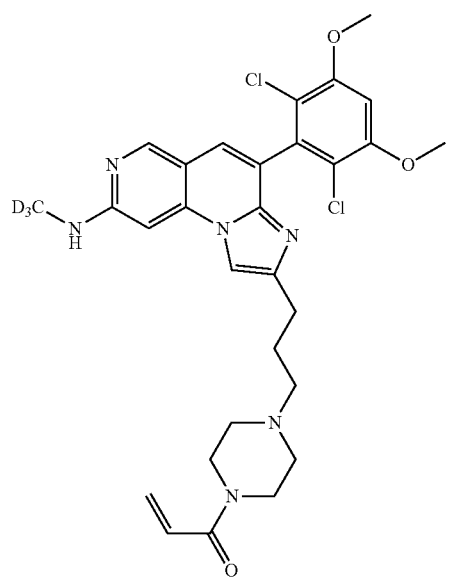
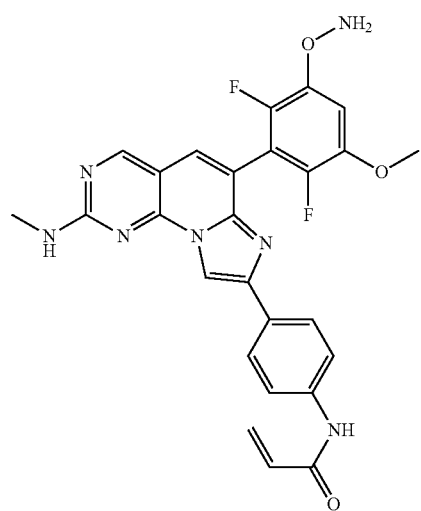
26
-continued
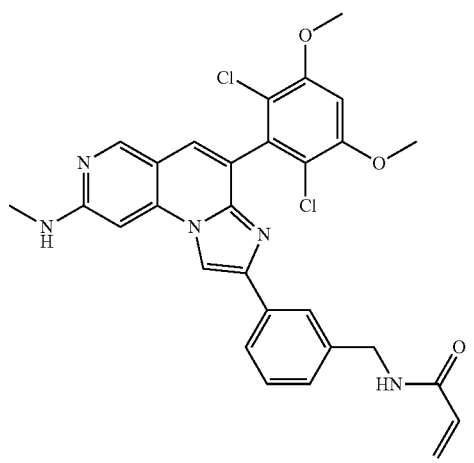
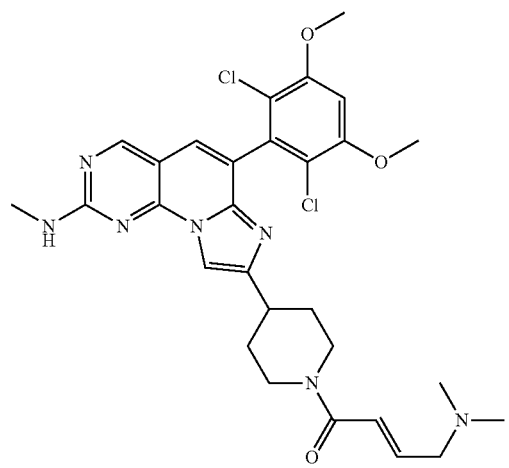
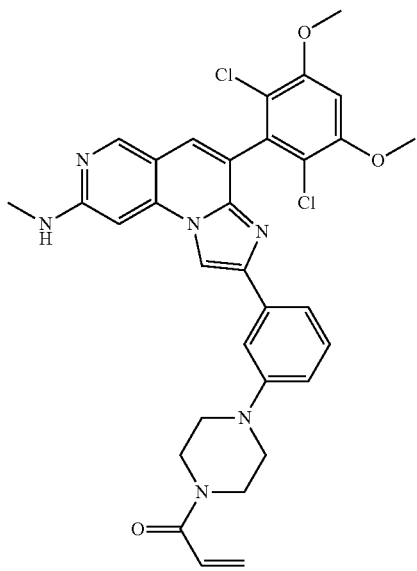

-continued

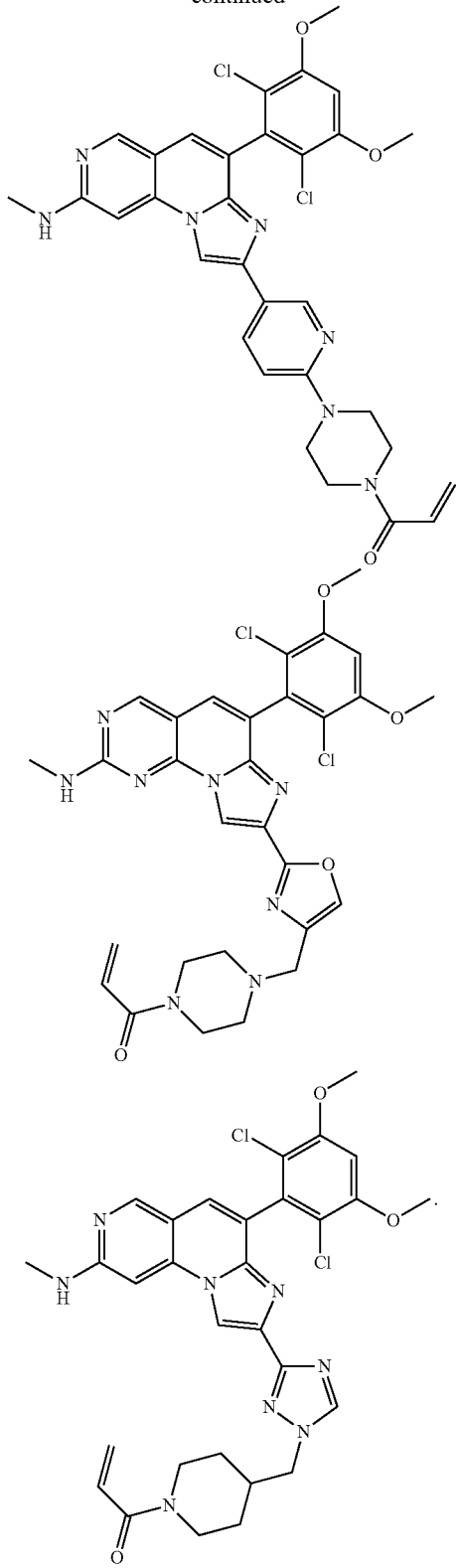

Furthermore, the present disclosure also provided a preparation method of the compound represented by formula (I), comprising the following steps:

a) conducting a condensation reaction with a compound represent by formula (A) and an α-halocarbonyl compound or an equivalent thereof in the presence of an acid or a base to prepare a compound represented by formula (B); and b) conducting a substitution reaction or coupling reaction with the compound represented by formula (B) and an amine compound in the presence of a acid, a base or a transition metal catalyst to prepare a compound represented by formula (C); and c) conducting a condensation reaction with the compound represented by formula (C) and an acrylic acid or acryloyl chloride compound in the presence of a base or a condensation reagent to prepare the compound represented by formula (I);

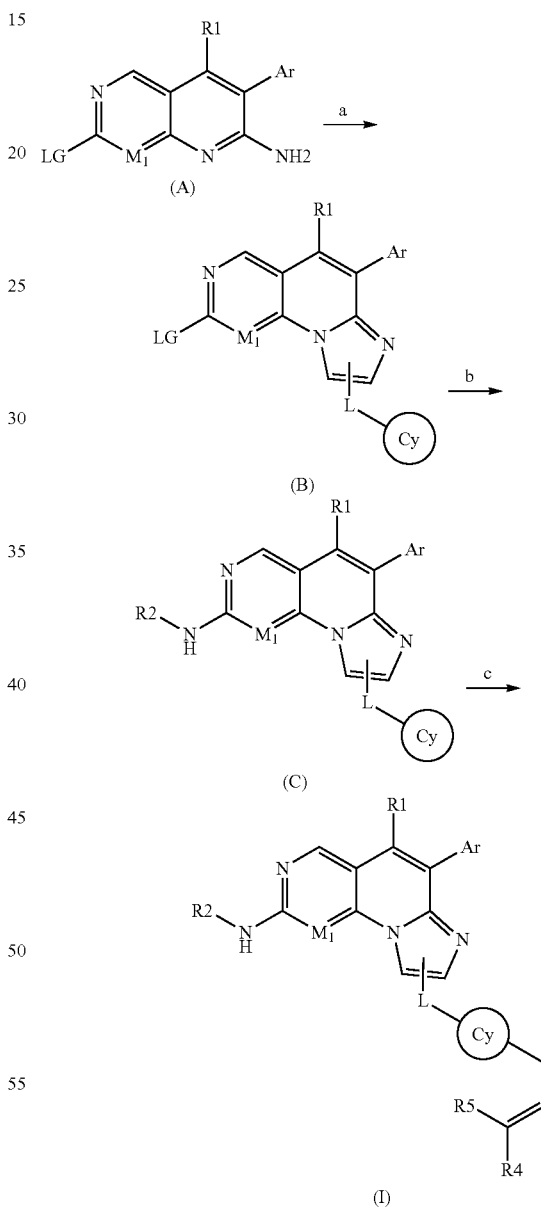

in each of the formulas, LG represents a leaving group conventionally used in such reactions in the art, e.g., halogen, sulfuryl, sulfinyl, sulfonate ester group, and other groups are as defined above.

Preferably, the steps a), b), c) are each performed in a solvent, and the solvents are each independently one or more selected from the group consisting of water, methanol, ethanol, isopropanol, ethylene glycol, N-methylpyrrolidone, dimethyl sulfoxide, tetrahydrofuran, toluene, dichloromethane, 1,2-dichloroethane, acetonitrile, N,N-dimethylformamide, N,N-dimethylacetamide and dioxane;

preferably, the transition metal catalyst is one or more selected from the group consisting of tris(dibenzylideneacetone)dipalladium ($Pd_2(dba)_3$), tetrakis(triphenylphosphine)palladium ($Pd(PPh_3)_4$), palladium acetate, palladium chloride, dichlorobis(triphenylphosphine)palladium, palladium trifluoroacetate, bis(triphenylphosphinepalladium) acetate, [1,1'-bis(diphenylphosphino)ferrocene]palladium dichloride, bis(triphenylphosphine)palladium dichloride and [1,2-bis(diphenylphosphino)ethane] palladium dichloride; the catalyst ligand is one or more selected from the group consisting of tri-tert-butylphosphine, tri-tert-butylphosphine tetrafluoroborate, tri-n-butylphosphine, triphenylphosphine, tri-p-tolylphosphine, tricyclohexylphosphine and tri-o-tolylphosphine;

preferably, the condensation reagent is one or more selected from the group consisting of DCC, DIC, CDI, EDCI, HOAt, HOBt, BOP, PyBOP, HATU and TBTU;

preferably, the base comprises an organic base and/or an inorganic base; wherein the inorganic base is one or more selected from the group consisting of sodium hydride, potassium hydroxide, sodium acetate, potassium acetate, potassium tert-butoxide, sodium tert-butoxide, potassium fluoride, cesium fluoride, potassium phosphate, potassium carbonate, potassium bicarbonate, sodium carbonate and sodium bicarbonate; the organic base is one or more selected from the group consisting of pyridine, triethylamine, N,N-diisopropylethylamine, 1,8-diazabicyclo[5.4.0]undec-7-ene (DBU), hexamethyldisilyl lithium, hexamethyldisilyl sodium and dimethylpyridine;

preferably, the acid is one or more selected from the group consisting of hydrochloric acid, sulfuric acid, phosphoric acid, methanesulfonic acid, toluene sulfonic acid, trifluoroacetic acid, formic acid, acetic acid and trifluoromethanesulfonic acid.

In the present disclosure, the compound represented by formula (A) and all reagents involved in the above preparation method are commercially available, or can be prepared by those skilled in the art by referring to synthesis methods in the prior art.

According to the above preparation method disclosed by the present disclosure, those skilled in the art can adopt the same principle and method to prepare each specific compound involved by the compound represented by formula (I) of the present disclosure.

Furthermore, the present disclosure also provides the pharmaceutical composition comprising a therapeutically effective amount of the compound represented by formula (I), or the pharmaceutically acceptable salt thereof, or an enantiomer, diastereomer, tautomer, solvate, polymorph or prodrug thereof, and at least one pharmaceutical excipient.

Furthermore, the present disclosure also provides a use of the compound represented by formula (I), or the pharmaceutically acceptable salt thereof, or the enantiomer, diastereomer, tautomer, solvate, polymorph or prodrug thereof, or the pharmaceutical composition in the manufacture of a FGFR kinase inhibitor.

Furthermore, the present disclosure also provides a use of the compound represented by formula (I), or the pharmaceutically acceptable salt thereof, or the enantiomer, diastereomer, tautomer, solvate, polymorph or prodrug thereof, or the above pharmaceutical composition in the manufacture of a medicament for preventing and/or treating a disease related to the activity or expression quantity of a protein kinase (especially FGFR kinase), especially in the manufacture of a medicament for preventing and/or treating a tumor. Wherein, the tumor includes but is not limited to one or more selected from the group consisting of non-small cell lung cancer, small cell lung cancer, lung adenocarcinoma, squamous cell lung cancer, breast cancer, prostate cancer, liver cancer, skin cancer, gastric cancer, epithelial cell cancer, gastrointestinal stromal tumor, intestinal cancer, bile duct cancer, gallbladder cancer, colorectal cancer, brain cancer, leukemia, lymphoma, nasopharyngeal cancer, bladder cancer, pancreatic cancer, etc., especially liver cancer or bile duct cancer.

Furthermore, the present disclosure also provides a method for preventing and/or treating a tumor, comprising administering to an individual in need thereof a therapeutically effective amount of the compound represented by formula (I), or the pharmaceutically acceptable salt thereof, or the enantiomer, diastereomer, tautomer, solvate, polymorph or prodrug thereof.

The compound represented by formula (I) can inhibit various tumor cells, especially can efficiently kill hepatocellular carcinoma cells, and is a novel type of therapeutic medicament for hepatocellular carcinoma with a new action mechanism.

Terms

Unless otherwise specified, the scientific and technical terms used herein have the same meaning as commonly understood by those skilled in the art to which the claims belongs. Unless otherwise specified, all patents, patent applications, and publications cited herein are incorporated herein by reference in their entirety.

It is to be understood that the foregoing brief description and the following detailed description are exemplary and explanatory only, which do not limit the subject of the present disclosure in any way. In the present application, unless otherwise specified, singular forms used herein also include plural referents. It must be noted that the singular forms used in the description and the claims include the plural forms of the indicated matters unless otherwise clearly stated herein. It should also be noted that the use of "or" means "and/or" unless otherwise specified. In addition, the terms "include" and other forms such as "comprise", "contain" and "involve" are not limiting.

Definitions of standard chemical terms can be found in references (including Carey and Sundberg, "ADVANCED ORGANIC CHEMISTRY 4TH ED." Vols. A (2000) and B (2001), plenum press, new York). Unless otherwise specified, conventional methods within the technical skills in the art, such as mass spectrometry, NMR, IR and UV/VIS spectrometry and pharmacological methods, are used. Unless a specific definition is proposed, the terms used herein in the description of analytical chemistry, organic synthesis chemistry, and drugs and pharmaceutical chemistry are known in the ar. Standard techniques can be used in chemical synthesis, chemical analysis, drug preparation, formulation and delivery, and treatment of the patients. For example, the reaction and purification can be carried out by using the manufacturer's instructions for the use of the kit, or in a manner known in the art or according to the instructions of the present disclosure. Generally, the above techniques and methods can be implemented by following conventional methods well known in the art according to descriptions in a plurality of general and more specific documents cited and discussed in this specification. In this specification, groups and the substituents thereof can be selected by those skilled in the art to provide stable structural parts and compounds.

In the present disclosure, when one of the variables is selected from a chemical bond, the two groups to which it is connected are directly connected, for example, when L in A-L-Z represents a chemical bond, the structure of A-L-Z is actually A-Z; when the type and scope of substituents are defined in a form similar to "$R^1$-$R^2$-$R^3$-", it means that the substituents shown as "$R^1$-$R^2$-$R^3$-" are directly attached to the parent compound as a whole by $R^3$, and the substituents shown as $R^1$, $R^2$ and $R^3$ are connected to each other sequentially through chemical bonds.

When a substituent is described by a conventional chemical formula written from left to right, the substituent also includes the chemically equivalent substituent obtained when the structural formula is written from right to left. For example, —CH2O— is equivalent to —OCH2-.

The chapter titles used herein are only for the purpose of organizing the article and should not be interpreted as limiting the subject. All literatures or literature parts cited in the present application, including but not limited to patents, patent applications, articles, books, operation manuals and papers, are incorporated herein by reference in their entirety.

Some chemical groups defined herein are preceded by simplified symbols to indicate the total number of carbon atoms present in the group. For example, C1-6 alkyl refers to alkyl containing a total of 1 to 6 carbon atoms as defined below. The total number of carbon atoms in the simplified symbol does not include carbon that may be present in the substituent of the group.

In addition to the foregoing, when used in the specification and claims of the present application, unless otherwise specified, the following terms have the meanings below.

In the present application, the term "halogen" refers to fluorine, chlorine, bromine or iodine.

"Hydroxyl" refers to —OH group.

"Hydroxyalkyl" refers to an alkyl group as defined below substituted by hydroxyl (—OH).

"Carbonyl" refers to —C(═O)— group.

"Nitro" refers to —$NO_2$.

"Cyano" refers to —CN.

"Amino" refers to —$NH_2$.

"Substituted amino" refers to an amino group substituted by one or two selected from the group consisting of alkyl, alkylcarbonyl, aralkyl and heteroaralkyl as defined below, for example, monoalkylamino, dialkylamino, alkylamido, aralkylamino, heteroarylalkylamino.

"Carboxyl" refers to —COOH.

In the present application, as a group or apart of other groups (for example, when used in a group of "alkyl substituted by halogen" or the like), the term "alkyl" refers to a straight or branched hydrocarbon chain group consisting of only carbon atoms and hydrogen atoms, without unsaturated bonds, containing, for example, 1 to 12 (preferably 1 to 8, more preferably 1 to 6) carbon atoms, and connected to the rest of the molecule by a single bond. Examples of alkyl include, but are not limited to, methyl, ethyl, n-propyl, isopropyl, n-butyl, isobutyl, sec-butyl, tert-butyl, n-pentyl, 2-methylbutyl, 2,2-dimethyl propyl, n-hexyl, heptyl, 2-methylhexyl, 3-methylhexyl, octyl, nonyl, decyl, etc.

In the present application, as a group or a part of other groups, the term "alkenyl" refers to a straight or branched hydrocarbon chain group consisting of only carbon atoms and hydrogen atoms, containing at least one double bond, containing, for example, 2 to 14 (preferably 2 to 10, more preferably 2 to 6) carbon atoms, and connected to the rest of the molecule by a single bond, for example, but not limited to, vinyl, propenyl, allyl, but-1-enyl, but-2-enyl, pent-1-enyl, pent-1,4-dienyl, etc.

In the present application, as a group or a part of other groups, the term "alkynyl" refers to a straight or branched hydrocarbon chain group consisting of only carbon atoms and hydrogen atoms, containing at least one triple bond and one or more optional double bonds, containing, for example, 2 to 14 (preferably 2 to 10, more preferably 2 to 6) carbon atoms, and connected to the rest of the molecule by a single bond, for example, but not limited to, ethynyl, prop-1-ynyl, but-1-ynyl, pent-1-ene-4-ynyl, etc.

In the present application, as a group or a part of other groups, the term "cycloalkyl" refers to a stable nonaromatic monocyclic or polycyclic hydrocarbon group consisting of only carbon atoms and hydrogen atoms. The cycloalkyl can include a fused ring system, a bridged ring system or a spiro ring system and have 3 to 15 carbon atoms, preferably 3 to 10 carbon atoms, more preferably 3 to 8 carbon atoms. The cycloalkyl is saturated or unsaturated and can be connected to the rest of the molecule by any suitable carbon atom through a single bond.

Unless otherwise specified in the specification, the carbon atoms in the cycloalkyl group can be optionally oxidized. Examples of cycloalkyl include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-indanyl, 1,2,3,4-tetrahydro-naphthyl, 5,6,7,8-tetrahydro-naphthyl, 8,9-dihydro-7H-benzocycloheptene-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, 7,7-dimethyl-bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-pentalenyl etc.

In the present application, as a group or apart of other groups, the term "heterocyclyl" refers to a stable 3-20 membered nonaromatic cyclic group consisting of 2 to 14 carbon atoms and 1 to 6 heteroatoms selected from N, P, O and S. Unless otherwise specified in the specification, the heterocyclyl can be a monocyclic, bicyclic, tricyclic or polycyclic system, and can include a fused ring system, a bridged ring system or a spiro ring system; the nitrogen, carbon or sulfur atoms in the heterocyclyl can be optionally oxidized; the nitrogen atom can be optionally quaternized; and the heterocyclyl can be partially or completely saturated. The heterocyclyl can be connected to the rest of the molecule by carbon atoms or heteroatoms through single bond. In the heterocyclyl containing fused rings, one or more rings can be aryl or heteroaryl as defined below, provided that the connection point to the rest of the molecule is an atom on the nonaromatic ring. For the purpose of the present disclosure, the heterocyclyl is preferably a stable 4-11 membered non-aromatic monocyclic, bicyclic, bridged or spiro group containing 1 to 3 heteroatoms selected from N, O and S, and more preferably a stable 4-8 membered non-aromatic monocyclic, bicyclic, bridged or spiro group containing 1 to 3 heteroatoms selected from N, O and S. Examples of the heterocyclyl include, but are not limited to, pyrrolidinyl, morpholinyl, piperazinyl, homopiperazinyl, piperidinyl, thiomorpholinyl, 2,7-diaza-spiro[3.5]nonane-7-yl, 2-oxa-6-aza-spiro[3.3]heptane-6-yl, 2,5-diaza-bicyclo[2.2.1]heptane-2-yl, azetidinyl, pyranyl, tetrahydropyranyl, thiopyranyl, tetrahydrofuranyl, oxazinyl, dioxolanyl, tetrahydroisoquinolinyl, decahydroisoquinolinyl, imidazolinyl, imidazolidinyl, quinolizidinyl, thiazolinyl, isothiazolinyl, isoxazolinyl, indolinyl, octahydroindolyl, octahydroisoindolyl, pyrrolidinyl, pyrazolinyl, phthalimido, etc.

In the present application, as a group or a part of other groups, the term "aryl" refers to a conjugated hydrocarbon ring system group containing 6 to 18 carbon atoms, preferably 6 to 10 carbon atoms. For the purpose of the present disclosure, the aryl can be a monocyclic, bicyclic, tricyclic or polycyclic system, and can also be fused to a cycloalkyl or heterocyclyl as defined above, provided that the aryl is connected to the rest of the molecule by a single bond through an atom on the aromatic ring. Examples of aryl include, but are not limited to, phenyl, naphthyl, anthracenyl, phenanthryl, fluorenyl, 2,3-dihydro-1H-isoindolyl, 2-benzoxazolinone, 2H-1,4-benzoxazine-3(4H)-one-7-yl, etc.

In the present application, the term "arylalkyl" refers to the above-defined alkyl substituted by the above-defined aryl.

In the present application, as a group or a part of other groups, the term "heteroaryl" refers to a 5-16 membered conjugated ring system group containing 1 to 15 carbon atoms (preferably 1 to 10 carbon atoms) and 1 to 6 heteroatoms selected from N, O and S arranged on the ring. Unless otherwise specified in the specification, the heteroaryl can be a monocyclic, bicyclic, tricyclic or polycyclic system, and can also be fused to the cycloalkyl or heterocyclyl as defined above, provided that the heteroaryl is connected to the rest of the molecule by a single bond through the atom on the aromatic ring. Nitrogen, carbon or sulfur atoms in the heteroaryl can be optionally oxidized; the nitrogen atom can be optionally quaternized. For the purpose of the present disclosure, the heteroaryl is preferably a stable 5-12 membered aromatic group containing 1 to 5 heteroatoms selected from N, O and S, more preferably a stable 5-10 membered aromatic group containing 1 to 4 heteroatoms selected from N, O and S or a 5-6 membered aromatic group containing 1 to 3 heteroatoms selected from N, O and S. Examples of the heteroaryl include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furanyl, pyrrolyl, triazolyl, tetrazolyl, triazinyl, indolizinyl, isoindolyl, indazolyl, isoindazolyl, purinyl, quinolinyl, isoquinolinyl, naphthyridinyl, naphthyridinyl, quinoxalinyl, pteridinyl, carbazolyl, carbolinyl, phenanthridinyl, phenanthrolinyl, acridinyl, phenazinyl, isothiazolyl, benzothiazolyl, benzothiophenyl, oxatriazolyl, cinnolinyl, quinazolinyl, phenylthio, indolizinyl, o-phenanthrolinyl, isoxazolyl, phenoxazinyl, phenothiazinyl, 4,5,6,7-tetrahydrobenzo[b]thienyl, naphthalopyridinyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the present application, the term "heteroarylalkyl" refers to the alkyl as defined above substituted by the heteroaryl as defined above.

In the present application, "optional" or "optionally" refers to that the event or condition described later may or may not occur, and the description includes both the occurrence and non-occurrence of the event or condition. For example, "optionally substituted aryl" refers to that the aryl is substituted or unsubstituted, and includes both substituted aryl and unsubstituted aryl.

As used herein, the terms "moiety", "structural moiety", "chemical moiety", "group" and "chemical group" refer to a specific fragment or functional group in the molecule.

Chemical moieties are generally considered to be chemical entities embedded in or attached to molecules.

"Stereoisomer" refers to a compound composed of the same atoms, bonded by the same bond, but with different three-dimensional structures. The present disclosure encompasses various stereoisomers and mixtures thereof.

When a compound of the present disclosure contains an olefinic double bond, unless otherwise specified, the compound of the present disclosure is intended to include E- and Z-geometric isomers.

"Tautomer" refers to an isomer formed by proton transfer from one atom of a molecule to another atom of the same molecule. All tautomeric forms of the compounds of the present disclosure are encompassed within the scope of the present disclosure.

The compounds or the pharmaceutically acceptable salts thereof of the present disclosure may contain one or more chiral carbon atoms, and thus can produce enantiomers, diastereomers and other stereoisomeric forms. Each chiral carbon atom can be defined as (R)- or (S)-based on stereochemistry. The present disclosure intends to encompass all possible isomers, as well as racemates and optically pure forms thereof. The compounds of the present disclosure can be prepared by selecting racemates, diastereomers or enantiomers as raw materials or intermediates. Optically active isomers can be prepared by using chiral synthons or chiral reagents, or can be resolved by using conventional techniques, such as crystallization and chiral chromatography.

Conventional techniques for preparing/resolving individual isomers include chiral synthesis from suitable optically pure precursors or resolution of racemates (or racemates of salts or derivatives) by using, for example, chiral high performance liquid chromatography, which can be refer to, for example, Gerald Gubitz and Martin G. Schmid (Eds.), Chiral Separations, Methods and Protocols, *Methods in Molecular Biology*, Vol. 243, 2004; A. M. Stalcup, Chiral Separations, *Annu. Rev. Anal. Chem.* 3:341-63, 2010; Fumiss et al. (eds.), VOGEL'S TESTBOOK CYCLOPEDIA OF PRACTICAL ORGANIC CHEMISTRY 5.sup.TH ED., Longman Scientific and Technical Ltd., Essex, 1991, 809-816; Heller, *Acc. Chem. Res.* 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" refers to a salt formed with an inorganic or organic acid that can retain the biological effectiveness of the free base without other side effects. Inorganic acid salts include but are not limited to hydrochloride, hydrobromide, sulfate, nitrate, phosphate, etc.; organic acid salts include, but are not limited to, formate, acetate, 2,2-dichloroacetate, trifluoroacetate, propionate, caproate, caprylate, caprate, undecenoate, glycolate, gluconate, lactate, sebacate, adipate, glutarate, malonate, oxalate, maleate, succinate, fumarate, tartrate, citrate, palmitate, stearate, oleate, cinnamate, laurate, malate, glutamate, pyroglutamate, aspartate, benzoate, mesylate, benzenesulfonate, p-toluenesulfonate, alginate, ascorbate, salicylate, 4-aminosalicylate and naphthalene disulfonate, etc. These salts can be prepared by methods known in the art.

"Pharmaceutically acceptable base addition salt" refers to a salt formed with an inorganic base or organic base that can retain the biological effectiveness of the free acid without other side effects. Salts derived from inorganic bases include but are not limited to sodium salt, potassium salt, lithium salt, ammonium salt, calcium salt, magnesium salt, iron salt, zinc salt, copper salt, manganese salt, aluminum salt, etc. Preferred inorganic salts are ammonium, sodium, potassium, calcium and magnesium salts. Salts derived from organic bases include but are not limited to the following salts: primary amines, secondary amines and tertiary amines, substituted amines including natural substituted amines, cyclic amines and basic ion exchange resins, for example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, etc. Preferred organic bases include isopropylamine, diethylamine, ethanolamine, trimethylamine, dicyclohexylamine, choline and caffeine. These salts can be prepared by methods known in the art.

"Polymorph" refers to different solid crystalline phases of certain compounds of the present disclosure generated by the presence of two or more different molecular arrangements in solid state. Certain compounds of the present disclosure can have more than one crystal form, and the present disclosure intends to encompass various crystal forms and mixtures thereof.

In general, crystallization will produce solvates of the compounds of the present disclosure. As used herein, the term "solvate" refers to an aggregate comprising one or more molecules of the compound of the present disclosure and one or more solvent molecules. The solvent can be water, in which case the solvate is hydrate. Alternatively, the solvent can be an organic solvent. Therefore, the compounds of the present disclosure can exist as hydrates, including monohydrate, dihydrate, hemihydrate, sesquihydrate, trihydrate, tetrahydrate, etc., and corresponding solvated forms. The compounds of the present disclosure can form real solvates, but in some cases, can also retain only indeterminate water or a mixture of water and part of indeterminate solvent can be retained. The compounds of the disclosure can react in a solvent or precipitate out or crystallize out from a solvent. Solvates of the compounds of the present disclosure are also encompassed within the scope of the present disclosure.

The present disclosure also includes prodrugs of the above compounds. In the present application, the term "prodrug" refers to a compound that can be converted into the bioactive compound of the present disclosure under physiological conditions or by solvent decomposition. Therefore, the term "prodrug" refers to a pharmaceutically acceptable metabolic precursor of the compound of the present disclosure. When administered to an individual in need, the prodrug may not have activity but is converted into the active compound of the present disclosure in vivo. Produgss are usually rapidly converted in vivo to produce the parent compound of the present disclosure, for example by hydrolysis in blood. Prodrugs generally provide the advantages of solubility, histocompatibility or sustained release in mammalian organisms. Prodrugs include known amino protecting groups and carboxyl protecting groups. Specific preparation methods of prodrugs can be referred to Saulnier, M. G., et al., *Bioorg. Med. Chem. Lett.* 1994, 4, 1985-1990; Greenwald, R. B., et al., *J. Med. Chem.* 2000, 43, 475.

In the present application, "pharmaceutical composition" refers to a formulation of the compound of the present disclosure and a medium commonly accepted in the art for delivering bioactive compounds to mammals (e.g., humans). The medium comprises a pharmaceutically acceptable carrier. The purpose of the pharmaceutical composition is to promote the administration of organisms, facilitate the absorption of active ingredients for further exerting biological activity.

As used herein, the term "pharmaceutically acceptable" refers to a substance (e.g., a carrier or diluent) that does not affect the biological activity or properties of the compounds of the present disclosure, and is relatively non-toxic, i.e., the substance can be applied to an individual without causing adverse biological reactions or interacting with any component contained in the composition in an adverse manner.

In the present application, "pharmaceutically acceptable carrier" includes but is not limited to any adjuvants, carriers, excipients, glidants, sweeteners, diluents, preservatives, dyes/colorants, flavoring agents, surfactants, wetting agents, dispersants, suspending agents, stabilizers, isotonic agents, solvents or emulsifiers that are acceptable for human or livestock use permitted by relevant government authorities.

The "tumor" and "disease related to abnormal cell proliferation" etc., in the present disclosure include but are not limited to leukemia, gastrointestinal stromal tumor, histiocytic lymphoma, non-small cell lung cancer, small cell lung cancer, pancreatic cancer, squamous cell lung cancer, lung adenocarcinoma, breast cancer, prostate cancer, liver cancer, skin cancer, epithelial cell cancer, cervical cancer, ovarian cancer, intestinal cancer, nasopharyngeal cancer, brain cancer, bone cancer, esophageal cancer, melanoma, renal cancer, oral cancer, etc.

As used herein, the terms "prophylactic", "prevent" and "avoid" include the possibility for reducing the occurrence or deterioration of a disease or condition in patients.

As used herein, the term "treatment" and other similar synonyms include the following meanings:

(i) preventing the occurrence of the disease or condition in mammals, especially when such mammals are susceptible to such disease or disorder but have not yet been diagnosed as having such disease or disorder;

(ii) inhibition of the disease or condition, i.e., inhibition of its progression;

(iii) alleviation of the disease or condition, i.e., regression of the state of the disease or condition; or (iv) alleviation of the symptoms caused by the disease or disorder.

As use herein, the term "effective amount", "therapeutically effective amount" or "pharmaceutically effective amount" refers to the amount of at least one agent or compound that is sufficient to alleviate one or more symptoms of the disease or condition to be treated to some extent after administration. The result may be reduction and/or remission of signs, symptoms or causes, or any other desired changes in the biological system. For example, an "effective amount" for treatment is the amount of a composition comprising the compound disclosed herein required to provide significant disease relief effects in clinic. Effective amounts suitable for any individual case can be determined using techniques such as dose escalation tests.

As used herein, the terms "take" "administration" "dose" and the like refer to a method capable of delivering a compound or composition to a desired site for biological action. The method includes, but is not limited to, oral route, duodenal route, parenteral injection (including intravenous, subcutaneous, intraperitoneal, intramuscular, intra-arterial injection or infusion), local administration, and rectal administration. Those skilled in the art are familiar with the administration techniques that can be used for the compounds and methods described herein, for example, those described in Goodman and Gilman, The Pharmaceutical Basis of Therapeutics, Current. Pergamon; and Remington's, Pharmaceutical Sciences (current edition), Mack Publishing Co., Easton, Pa. In preferred embodiments, the compounds and compositions discussed herein are administered orally.

As use herein, the terms "drug combination", "combined pharmacotherapy", "combination of drug", "administration of other therapies", "administration of other therapeutic agents" and the like refer to a drug therapy obtained by mixing or combining more than one active ingredient, including fixed and unfixed combinations of active ingredients. The term "fixed combination" refers to the simultaneous administration of at least one compound described herein and at least one synergistic agent to a patient in the form of a single entity or a single dosage form. The term "unfixed combination" refers to simultaneous administration, combination or sequential administration at variable intervals of at least one compound described herein and at least one synergistic formulation to a patient in the form of a separate entity. These are also applied to cocktail therapy, e.g., administration of three or more active ingredients.

Those skilled in the art should also understand that in the method described below, the functional group of the intermediate compound may need to be protected by an appropriate protecting group. Such functional groups include hydroxyl, amino, sulfanyl and carboxylic acid groups. Suitable protecting groups of hydroxyl group include trialkylsilyl or diarylalkylsilyl (e.g., tert-butyl dimethylsilyl, tert-butyl diphenylsilyl or trimethylsilyl), tetrahydropyranyl, benzyl, etc. Suitable protecting groups of amino, amidino and guanidine groups include tert-butoxycarbonyl, benzyloxycarbonyl, etc. Suitable protecting groups of sulfanyl group include —C(O)—R" (wherein R" is alkyl, aryl or aralkyl), p-methoxybenzyl, trityl, etc. Suitable protecting groups of carboxyl group include alkyl, aryl or aralkyl esters.

Protective groups can be introduced and removed according to standard techniques known to those skilled in the art and described herein. The use of protective groups is detailed in Greene, T. W. and P. G. M. Wuts, Protective Groups in Organic Synthesis, (1999), 4th Ed., Wiley. The protecting group can also be a polymer resin.

It should be understood that within the scope of the present disclosure, the above-mentioned technical features of the present disclosure and the technical features described in detail below (e.g., embodiments) can be combined with each other to form a new or preferred technical solution. Limited by space, it will not be described in detail.

DETAILED DESCRIPTION OF THE PREFERRED EMBODIMENTS

After long-term and in-depth research, the inventors have prepared a class of novel compounds having the structure represented by formula I, and have found that the compounds have better FGFR kinase inhibitory activity, and the compounds have a specific inhibitory effect on FGFR kinase at an extremely low concentration, which can be as low as ≤1 nmol/L, and the compounds have quite excellent proliferation inhibitory activity on tumor cells related to FGFR, so that the compounds can be useful for the treatment of diseases such as tumors associated with FGFR kinase mutation or abnormal expressions. Based on the above findings, the inventors have completed the present disclosure.

The present disclosure is further described below by way of embodiments, but the present disclosure is not therefore limited to the scope of the described embodiments. The specific conditions of the experimental methods that are not specified in the embodiments are usually in accordance with conventional methods and conditions, or in accordance with commercial instructions. Unless otherwise stated, percentages and parts are weight percentages and parts by weight.

PREPARATION OF INTERMEDIATES

Intermediate 1: 6-(2,6-dichloro-3,5-dimethoxy-phenyl)-2-methylthio-pyridine [2,3-d]pyrimidin-7-ylamine

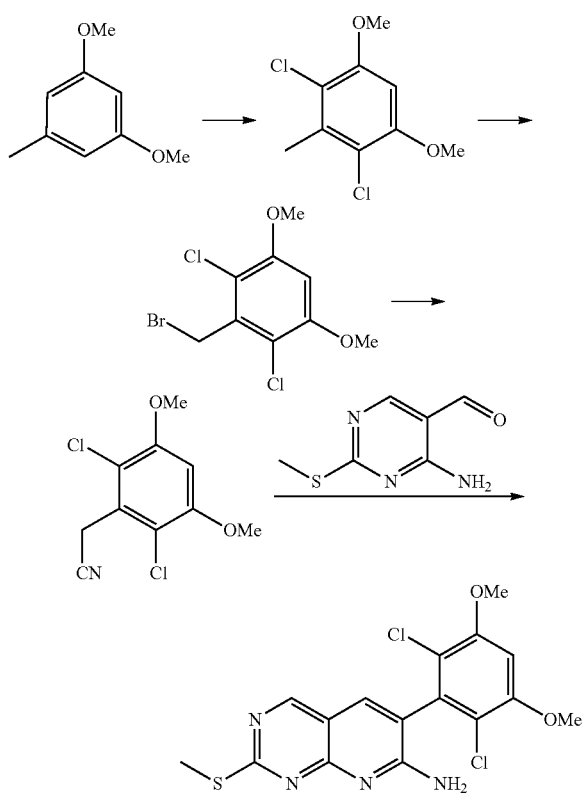

Step 1: 1,3-dimethoxy-5-methylbenzene (30 g, 0.20 mol) and dichloromethane (900 mL) were added to a dry round-bottom flask (1 L), then thionyl chloride (52.5 g, 0.40 mol) was added dropwise to the above solution under ice bath cooling, after the completion of the addition, the resulting solution was stirred at room temperature overnight. After completion of the reaction, sodium bicarbonate aqueous solution was added dropwise to adjust pH=8, the resulting mixture was extracted with dichloromethane, washed with dilute hydrochloric acid and distilled water respectively, dried, and concentrated under reduced pressure to give 2,4-dichloro-1,5-dimethoxy-3-methylphenyl (31 g, white solid), which was directly used in the next step.

Step 2: 2,4-dichloro-1,5-dimethoxy-3-methylbenzene (31 g, 0.14 mol) was dissolved in carbon tetrachloride (600 mL) and filled into a dry round bottom flask (1000 mL), then azodiisobutyronitrile (3.0 g, 0.018 mol) and N-bromosuccinimide (27.6 g, 0.154 mol) were added sequentially at room temperature. The reaction was performed at 80° C. for 3 hours, sodium bicarbonate aqueous solution was added to quench the reaction, then the resulting mixture was extracted with dichloromethane. The organic phase was dried and concentrated, then crystallized with methyl tert-butyl ether to give 3-bromomethyl-2,4-dichloro-1,5-dimethoxybenzene (30 g, white solid).

Step 3: 3-bromomethyl-2,4-dichloro-1,5-dimethoxybenzene (30 g, 0.1 mol) and acetonitrile (500 mL) were added to a dry 1000 mL round bottom flask, then trimethylsilyl cyanide (12 g, 0.34 mmol) and tetrabutylammonium fluoride (100 mL, 1 mol/L) were added at room temperature. The resulting mixture was stirred at room temperature for 1 hour, TLC showed that the reaction was completed. The reaction mixture was concentrated under reduced pressure, and diluted with ethyl acetate. The organic phase was washed with water and saturated brine respectively, dried and concentrated, and the residue was slurried with ethyl acetate to give (2,6-dichloro-3,5-dimethoxy-phenyl)-acetonitrile (20 g, white solid).

Step 4: (2,6-dichloro-3,5-dimethoxy-phenyl)-acetonitrile (10.4 g, 0.028 mol) and N,N-dimethylformamide (100 mL) were added into a dry 250 mL round bottom flask, then 4-amino-2-methylthio-pyrimidine-5-formaldehyde (5 g, 0.02 mol) and potassium carbonate (12.25 g, 0.06 mol) were added sequentially at room temperature, the resulting mixture was stirred overnight until the completion of the reaction. The reaction mixture was extracted with ethyl acetate, the organic phase was washed with distilled water and saturated brine, dried and filtered, concentrated under reduced pressure, and the residue was purified by silica gel column chromatography with eluent system (dichloromethane:methanol=30:1) to give 6-(2,6-dichloro-3,5-dimethoxy-phenyl)-2-methylthio-pyridine[2,3-d] pyrimidin-7-ylamine (3.7 g, yellow solid). LC-MS: ESI[M+H]$^+$=399.0; $^1$H-NMR (400 MHz, CDCl$_3$) δ 8.80 (s, 1H), 7.69 (s, 1H), 6.67 (s, 1H), 3.97 (s, 6H), 2.68 (s, 3H).

Intermediate 2: 7-chloro-3-(2,6-dichloro-3,5-dimethoxy-phenyl)-[1,6]naphthyridine-2-ylamine

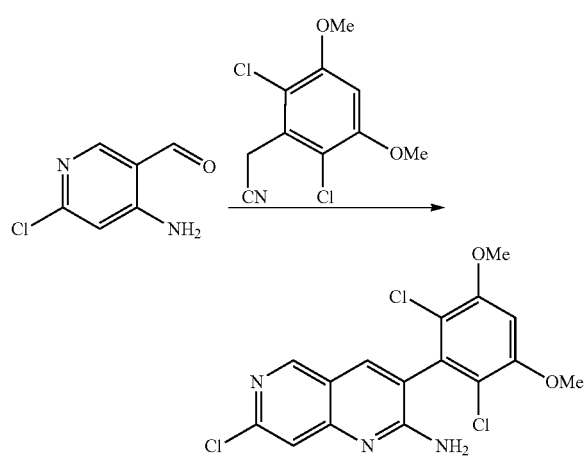

In a dry 250 mL round-bottom flask, 4-amino-6-chloro-pyridine-3-formaldehyde (2 g, 0.013 mol) and N-methylpyrrolidone (20 mL) were added, followed by the addition of (2,6-dichloro-3,5-dimethoxy-phenyl)-acetonitrile (4.4 g, 0.018 mol) and potassium carbonate (5.27 g, 0.039 mol), then the resulting mixture was stirred at 80° C. After completion of the reaction, the reaction mixture was extracted with ethyl acetate, and the organic phase was washed with distilled water and saturated brine sequentially, then dried and filtered, and concentrated under reduced pressure. The residue was purified by silica gel column chromatography with eluent system (dichloromethane:methanol=30:1) to give 7-chloro-3-(2,6-dichloro-3,5-dimethoxy-phenyl)-[1,6]naphthyridine-2-ylamine (0.8 g, yellow solid). LC-MS: ESI [M+H]$^+$=383.9; $^1$H-NMR (400 MHz, DMSO-d$_6$) δ 8.71 (s, 1H), 7.88 (s, 1H), 7.34 (s, 1H), 7.00 (s, 1H), 3.94 (s, 6H).

The following intermediates were prepared by above methods:

| ID. | Structure | Data |
|---|---|---|
| 3 | 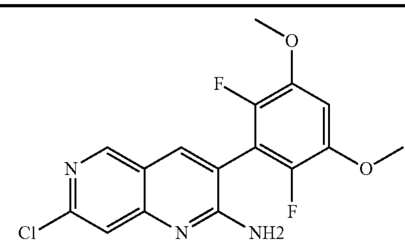 | MS (ESI+) m/z: 352.1/ 354.1 |
| 4 | 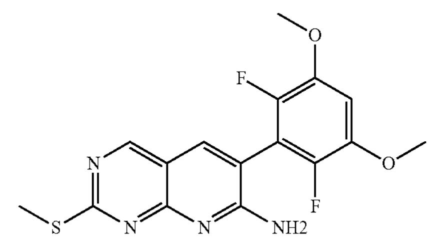 | MS (ESI+) m/z: 365.4 |

Intermediate 5: 3-[4-(2,6-dichloro-3,5-dimethoxy-phenyl)-8-methylthio-3,7,9,9b-tetraaza-cyclopentyl[a]naphthalene-2-yl]-propionaldehyde Step 1: 6-(2,6-dichloro-3,5-dimethoxy-phenyl)-2-methylthio-pyrido[2,3-d]pyrimidin-7-ylamine (4 g) and triethylamine (3 g) were dissolved in N,N-dimethylformamide (15 mL), and methyl 5-chloro-4-oxo-valerate (3.2 g) was added under stirring. After the addition was completed, the resulting mixture was heated to 80° C. and stirred overnight. After the reaction was completed, the mixture was extracted with dichloromethane (40 mL), the organic phase was washed with saturated sodium bicarbonate and water sequentially, dried over anhydrous sodium sulfate, filtered, concentrated under reduced pressure, and purified by column chromatography to give methyl 3-[4-(2,6-dichloro-3,5-dimethoxy-phenyl)-8-methylthio-3,7,9,9b-tetraaza-cyclopentyl[a]naphthalene-2-yl]propanoate (2.4 g). LC-MS: ESI [M+H]+=507.3.

Step 2: methyl 3-[4-(2,6-dichloro-3,5-dimethoxy-phenyl)-8-methylthio-3,7,9,9b-tetraaza-cyclopentyl[a]naphthalene-2-yl]propionate (2.4 g) was dissolved in anhydrous methanol (20 mL), sodium borohydride (150 mg) solid was added in batches under ice bath cooling, the resulting mixture was heated to reflux for 2 hours. The reaction was quenched by adding saturated ammonium chloride solution to the reaction mixture, then the solvent was removed under reduced pressure. The resulting mixture was extracted with dichloromethane, the organic phase was washed with water and saturated brine sequentially, dried over anhydrous sodium sulfate, filtered and concentrated, and purified by column chromatography to give 3-[4-(2,6-dichloro-3,5-dimethoxy-phenyl)-8-methylthio-3,7,9,9b-tetraaza-cyclopentyl[a]naphthalene-2-yl]-prop-1-ol (1.8 g). LC-MS: ESI [M+H]$^+$=480.3.

Step 3: 3-[4-(2,6-dichloro-3,5-dimethoxy-phenyl)-8-methylthio-3,7,9,9b-tetraaza-cyclopentyl[a]naphthalene-2-yl]-prop-1-ol (1.8 g) was dissolved in ethyl acetate (20 mL), then Dess-Martin oxidant (1.3 g) was added, the resulting mixture was heated to reflux for 3 hours.

The reaction was quenched by adding sodium thiosulfate solution into the reaction mixture, and the organic phases was isolated and washed with saturated sodium bicarbonate solution and water respectively, dried over anhydrous sodium sulfate, filtered, concentrated under reduced pressure, and purified by column chromatography to give 3-[4-(2,6-dichloro-3,5-dimethoxy-phenyl)-8-methylthio-3,7,9,9b-tetraaza-cyclopentyl[a]naphthalene-2-yl]-propionaldehyde (1.1 g). LC-MS: ESI [M+H]$^+$=478.3.

Intermediate 6-9 were prepared by the same method as intermediate 5:

Intermediate 6: 3-(8-chloro-4-(2,6-dichloro-3,5-dimethoxyphenyl)imidazo[1,2-a][1,6]naphthyridin-2-yl)propionaldehyde

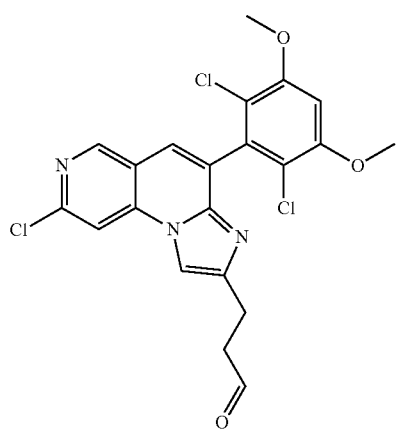 [SMILES: COc1cc(OC)c(Cl)c(-c2cc3cnc(Cl)cc3n3cc(CCC=O)nc23)c1Cl]

LC-MS: ESI [M+H]$^+$=464.3.

Intermediate 7: 3-(6-(2,6-difluoro-3,5-dimethoxy-phenyl)-2-(methylthio)imidazo[1',2':1,6]pyrido[2,3-d]pyrimidin-8-yl)propionaldehyde

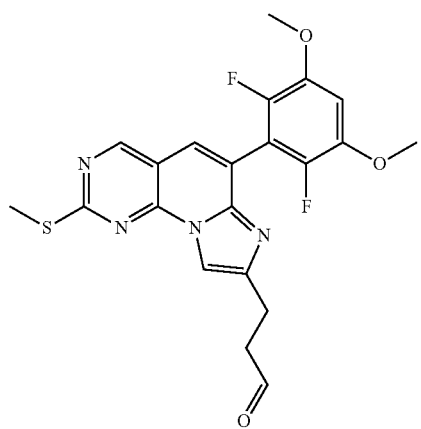

LC-MS: ESI [M+H]$^+$=445.3.

Intermediate 8

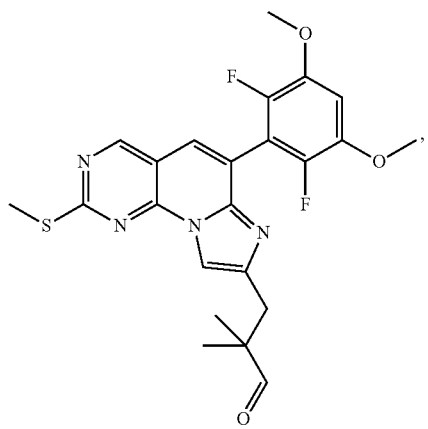

LC-MS: ESI [M+H]$^+$=473.2.

General Synthetic Method 1 of the Target Products

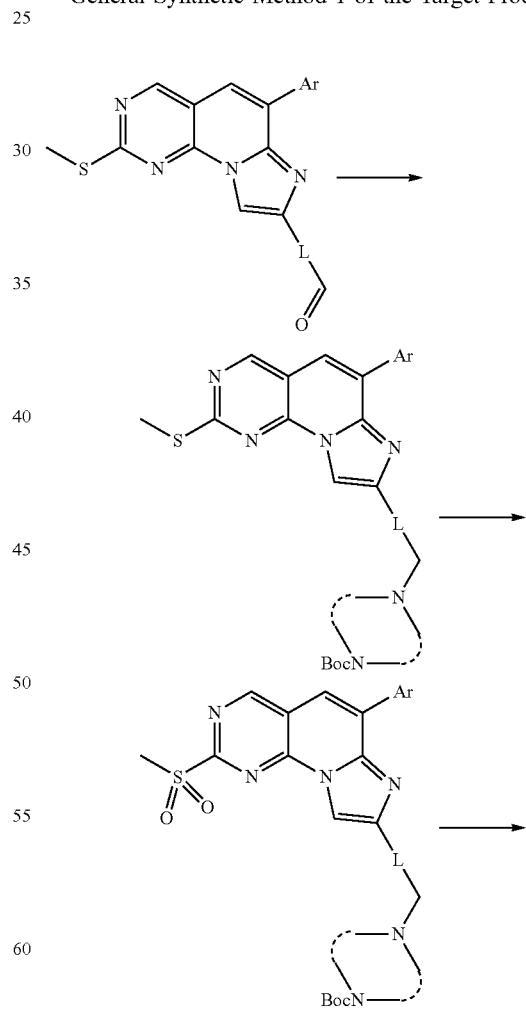

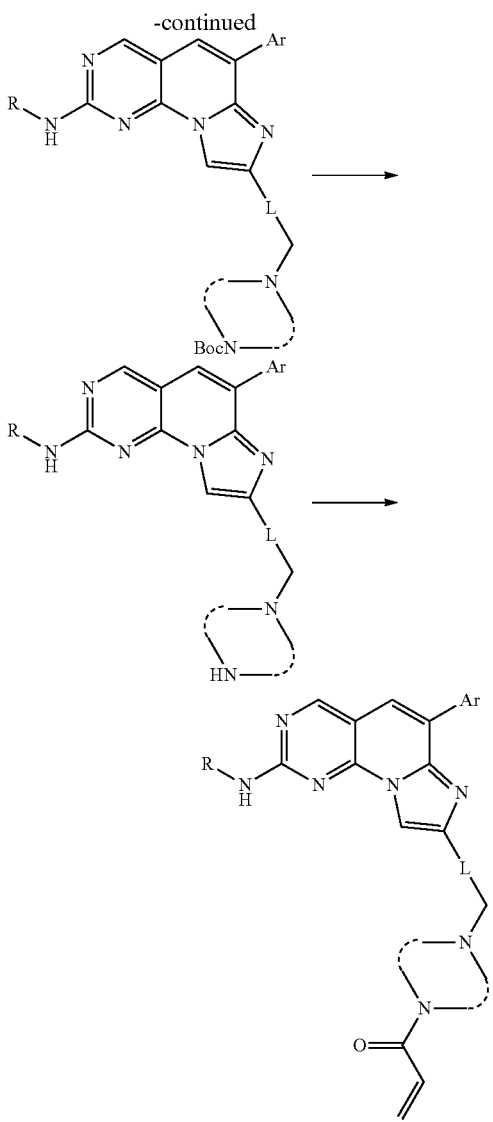

Step 1: Reductive Amination of N-Boc Diamine

Aldehyde intermediate (1 eq.) and N-Boc diamine were dissolved in anhydrous methanol, a drop of glacial acetic acid was added dropwise, and after the resulting mixture was stirred at room temperature for 1 hour, sodium borohydride solid (2 eq.) was added in batches under ice bath cooling, and the resulting mixture was stirred at room temperature overnight.

After the reaction was completed, saturated ammonium chloride solution was added to quench the reaction, the mixture was extracted with ethyl acetate. The organic phase was washed with saturated sodium bicarbonate solution and water respectively, dried over anhydrous sodium sulfate, filtered, concentrated under reduced pressure, and purified by column chromatography to give the target intermediate.

Step 2: Oxidation of Methylthio Group to Methylsulfonyl Group

Methylthio intermediate (1 eq.) was dissolved in dichloromethane, m-chloroperoxybenzoic acid (2 eq.) was added in batches under ice bath cooling, and the resulting mixture was stirred at room temperature overnight. After the reaction was completed, the reaction mixture was quenched with sodium thiosulfate solution, the organic phase was separated, washed with saturated sodium bicarbonate solution and water sequentially, dried with anhydrous sodium sulfate, filtered, concentrated under reduced pressure, and purified by column chromatography to give the intermediate of methylsulfonyl compound.

Step 3: Substituting Sulfonyl Group with Amine

Methylsulfonyl intermediate (1 eq.) and amine (2 eq.) were dissolved in anhydrous N,N-dimethylformamide and the resulting mixture was heated to 100° C. under microwave for 2 hours. After the reaction was completed, the mixture was extracted with dichloromethane, the organic phase was washed with saturated sodium bicarbonate solution and water sequentially, dried over anhydrous sodium sulfate, filtered, concentrated under reduced pressure, then purified by column chromatography to give the intermediate of nitro compound.

Step 4: Removing Boc Protecting Group

The raw material (1 eq.) was dissolved in dichloromethane, cooled in an ice bath, trifluoroacetic acid (10 eq.) was added and the resulting mixture was stirred for 2 hours. After the reaction was completed, the mixture was concentrated under reduced pressure, and the residue was directly used in the next step without purification.

Step 5: Acryloyl Acylation

Piperazine intermediate (1 eq.) and DIPEA (2 eq.) were dissolved in dry N,N-dimethylformamide, and acryloyl chloride (1.2 eq.) was slowly added dropwise under ice bath cooling. After the addition was completed, the reaction was performed at room temperature overnight. The reaction mixture was quenched by dichloromethane and saturated sodium bicarbonate solution, the organic phase was separated, then washed with water and saturated brine respectively, dried over anhydrous sodium sulfate, filtered, concentrated under reduced pressure, the residue was purified by preparative HPLC or Biotage Flash column chromatography to give the target compound.

Using intermediates 5-8 as raw materials, the following compounds were prepared by the steps and methods described in general method 1:

Embodiment 1: 1-(4-(3-(6-(2,6-difluoro-3,5-dimethoxyaniline)-2-(methylamine)imidazo[1',2':1,6]pyrido[2,3-d]pyrimidin-8-yl)propyl)piperazine-1-yl)prop-2-en-1-one

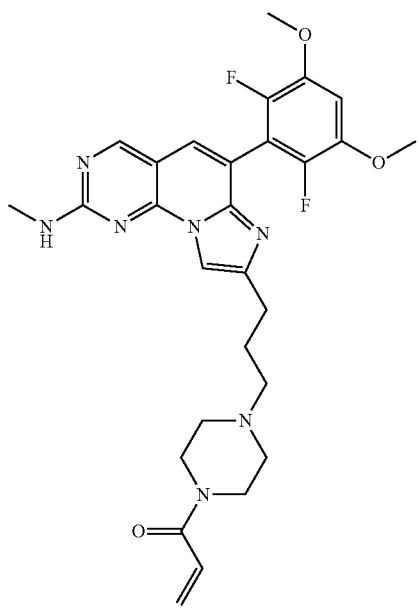

LC-MS: ESI [M+H]⁺=552.3; H-NMR (400 MHz, CD$_3$OD) 8.92 (s, 1H), 8.30 (s, 1H), 8.13 (s, 1H), 7.31 (s, 1H), 7.05 (s, 1H), 6.59-6.65 (dd, J=10.4, 16.8 Hz, 1H), 6.10-6.15 (dd, J=2.0, 16.8 Hz, 1H), 5.65-5.69 (dd, J=2.0, 10.4 Hz, 1H), 3.92 (s, 6H), 3.57-3.60 (m, 4H), 3.01 (s, 3H), 2.70-2.74 (m, 2H), 2.59-2.62 (m, 6H), 1.89-1.94 (m, 2H).

Embodiment 2: 1-(4-(3-(4-(2,6-difluoro-3,5-dimethoxyaniline)-8-(methylamine)imidazo[1,2-a][1,6]naphthyridin-2-yl)propyl)piperazine-1-yl)prop-2-en-1-one

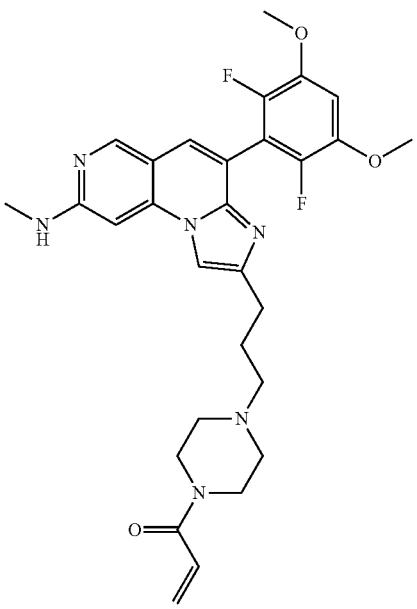

LC-MS: ESI [M+H]⁺=551.3; H-NMR (400 MHz, CD$_3$OD) 8.95 (s, 1H), 8.29 (s, 1H), 8.11 (s, 1H), 7.32 (s, 1H), 7.21 (s, 1H), 7.10 (s, 1H), 6.61-6.65 (dd, J=10.4, 16.8 Hz, 1H), 6.12-6.15 (dd, J=2.0, 16.8 Hz, 1H), 5.63-5.68 (dd, J=2.0, 10.4 Hz, 1H), 3.93 (s, 6H), 3.56-3.61 (m, 4H), 3.03 (s, 3H), 2.71-2.74 (m, 2H), 2.60-2.63 (m, 6H), 1.89-1.93 (m, 2H).

Embodiment 3: 1-(4-(3-(6-(2,6-dichloro-3,5-dimethoxyaniline)-2-(methylamine)imidazo[1',2':1,6]pyrido[2,3-d]pyrimidin-8-yl)propyl)piperazine-1-yl)prop-2-en-1-one Embodiment 4: 1-(4-(3-(2-((cyclopropylmethyl)amino)-6-(2,6-dichloro-3,5-dimethoxyaniline)imidazo[1',2':1,6]pyrido[2,3-d]pyrimidin-8-yl)propyl)piperazine-1-yl)prop-2-en-1-one

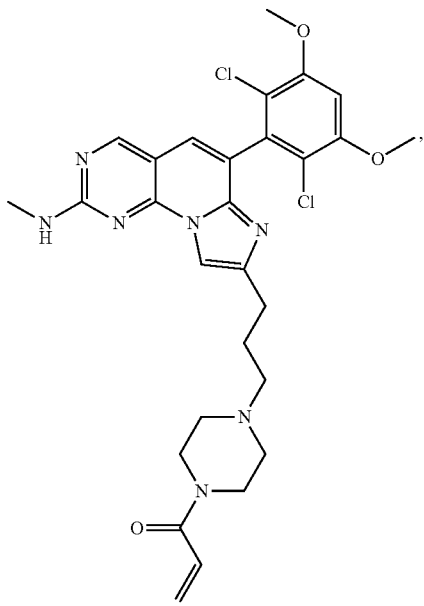

LC-MS: ESI [M+H]$^+$=583.8/585.7; H-NMR (400 MHz, CD$_3$OD) 8.79 (s, 1H), 8.25 (s, 1H), 8.08 (s, 1H), 7.28 (s, 1H), 6.85 (s, 1H), 6.61-6.68 (dd, J=10.4, 16.8 Hz, 1H), 6.10-6.14 (dd, J=2.0, 16.8 Hz, 1H), 5.65-5.68 (dd, J=2.0, 10.4 Hz, 1H), 3.87 (s, 6H), 3.57-3.59 (m, 4H), 3.01 (s, 3H), 2.70-2.74 (m, 2H), 2.59-2.62 (m, 6H), 1.89-1.94 (m, 2H).

LC-MS: ESI [M+2H]$^+$=312.5/313.5; H-NMR (400 MHz, CD$_3$OD) 9.07 (s, 1H), 8.18 (s, 1H), 8.30 (s, 1H), 7.37 (s, 1H), 7.06 (s, 1H), 6.74-6.81 (m, 1H), 6.09 (dd, J=2.4, 16.8 Hz, 1H), 5.66 (dd, J=2.4, 10.4 Hz, 1H), 4.29 (s, 3H), 3.57-3.61 (m, 4H), 3.34-3.37 (m, 2H), 2.65 (t, J=7.2 Hz, 2H), 2.28-2.35 (m, 6H), 1.75-1.82 (m, 2H), 0.97-1.18 (m, 1H), 0.46-0.48 (m, 2H), 0.32-0.34 (m, 2H).

Embodiment 5: 1-(4-(3-(4-(2,6-dichloro-3,5-dimethoxyaniline)-8-(methylamine)imidazo[1,2-a][1,6]naphthyridin-2-yl)propyl)piperazine-1-yl)prop-2-en-1-one

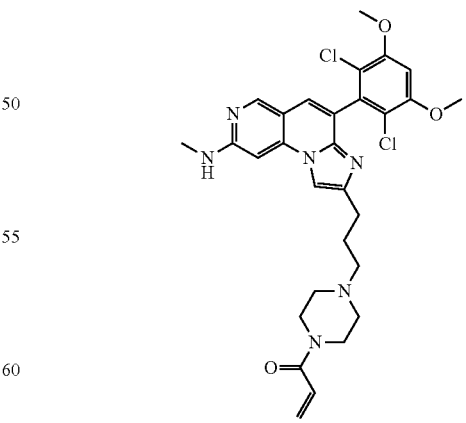

LC-MS: ESI [M+H]$^+$=583.4/585.4. H-NMR (400 MHz, CD$_3$OD) 8.93 (s, 1H), 8.32 (s, 1H), 8.14 (s, 1H), 7.31 (s, 1H), 7.23 (s, 1H), 7.08 (s, 1H), 6.61-6.65 (dd, J=10.4, 16.8 Hz, 1H), 6.12-6.15 (dd, J=2.0, 16.8 Hz, 1H), 5.63-5.68 (dd,

J=2.0, 10.4 Hz, 1H), 3.93 (s, 6H), 3.57-3.65 (m, 4H), 3.03 (s, 3H), 2.71-2.74 (m, 2H), 2.61-2.65 (m, 6H), 1.87-1.92 (m, 2H).

Embodiment 6: 1-(4-(3-(6-(2,6-dichloro-3,5-dimethoxyaniline)-2-((2-methoxyethyl)amino)imidazo[1',2':1,6]pyrido[2,3-d]pyrimidin-8-yl)propyl)piperazine-1-yl)prop-2-en-1-one

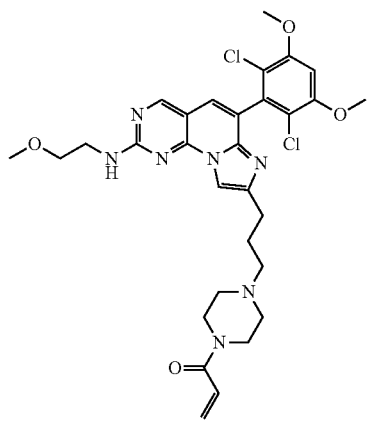

LC-MS: ESI [M+2H]⁺=314.5/315.5; H-NMR (400 MHz, CD₃OD) 8.97 (s, 1H), 8.08 (m, 2H), 7.39 (s, 1H), 7.04 (s, 1H), 6.74-6.81 (m, 1H), 6.09 (dd, J=2.4, 16.8 Hz, 1H), 5.66 (dd, J=2.4, 10.4 Hz, 1H), 4.31 (s, 3H), 3.58-3.64 (m, 4H), 3.51-3.52 (m, 4H), 3.31 (s, 3H), 2.63-2.67 (m, 2H), 2.31-2.35 (, 6H), 1.76-1.81 (m, 2H).

Embodiment 7: 1-(4-(3-(6-(2,6-dichloro-3,5-dimethoxyaniline)-2-((2-(4-methylpiperazine-1-yl)ethyl-ethyl)amino)imidazo[1',2':1,6]pyrido[2,3-d]pyrimidin-8-yl)propyl)piperazine-1-yl)prop-2-en-1-one

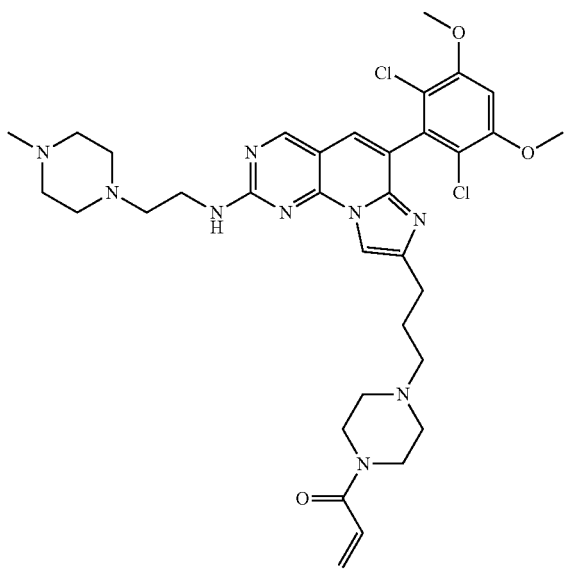

LC-MS: ESI [M+H]⁺=696.1/698.1; H-NMR (400 MHz, CD3OD) 8.77 (s, 1H), 8.01 (s, 1H), 7.15 (s, 1H), 6.67 (s, 1H), 6.52-6.58 (m, 1H), 6.26 (d, J=16.8 Hz, 1H), 6.16 (s, 1H), 5.67 (d, J=10.4 Hz, 1H), 3.96 (s, 6H), 3.67 (bs, 4H), 3.54 (s, 2H), 2.80-2.83 (m, 2H), 2.69-2.71 (m, 2H), 2.42-2.59 (m, 14H), 2.31 (s, 3H), 1.93-1.96 (m, 2H).

Embodiment 8: 1-(4-(3-(6-(2,6-dichloro-3,5-dimethoxyaniline)-2-(ethylamine)imidazo[1',2':1,6]pyrido[2,3-d]pyrimidin-8-yl)propyl)piperazine-1-yl)prop-2-en-1-one

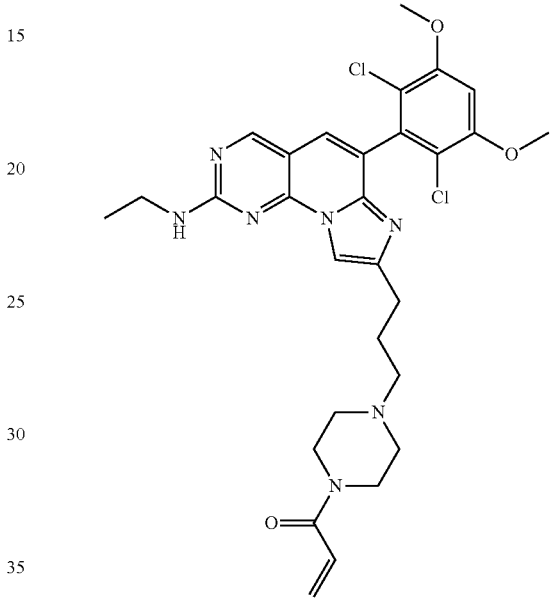

LC-MS: ESI [M+H]⁺=599.7/601.6; H-NMR (400 MHz, CD₃OD) 8.96 (s, 1H), 1.94 (bs, 2H), 7.37 (s, 1H), 7.05 (s, 1H), 6.77 (dd, J=10.4, 16.8 Hz, 1H), 6.08 (dd, J=16.8, 2.0 Hz, 1H), 5.66 (dd, J=10.8, 2.0 Hz, 1H), 3.99 (s, 3H), 3.50 (bs, 6H), 2.65 (t, J=7.2 Hz, 2H), 2.31-2.35 (m, 6H), 1.79 (t, J=7.2 Hz, 2H), 0.85 (bs, 3H).

| 51 | 52 |
|---|---|
| Embodiment 9: 1-(4-(3-(6-(2,6-dichloro-3,5-dimethoxyaniline)-2-((2-(dimethylamine)ethyl)amino)imidazo[1',2':1,6]pyrido[2,3-d]pyrimidin-8-yl)propyl)piperazine-1-yl)prop-2-en-1-one | Embodiment 10: 1-(4-(3-(6-(2,6-dichloro-3,5-dimethoxyaniline)-2-((2,3-dihydroxypropyl)amino)imidazo[1',2':1,6]pyrido[2,3-d]pyrimidin-8-yl)propyl)piperazine-1-yl)prop-2-en-1-one |

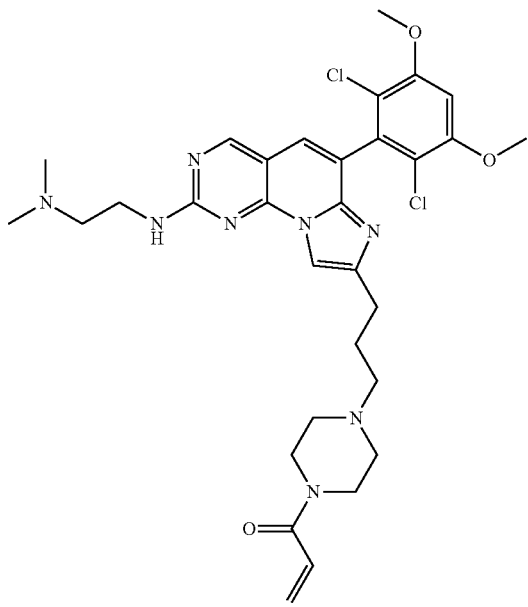

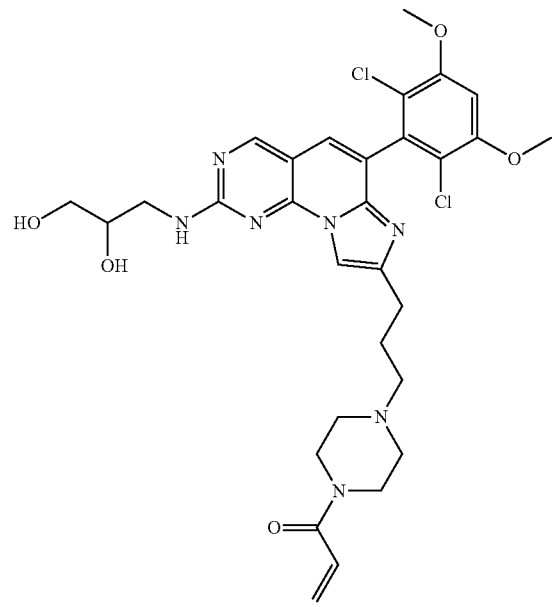 [SMILES: C=CC(=O)N1CCN(CCCc2cn3c(n2)c(-c2c(Cl)c(OC)cc(OC)c2Cl)cc2cnc(NCC(O)CO)nc23)CC1]

LC-MS: ESI [M+H]$^+$=321.1/321.9; H-NMR (400 MHz, CD$_3$OD) 8.76 (s, 1H), 8.00 (s, 1H), 7.15 (s, 1H), 6.66 (s, 1H), 6.52-6.59 (m, 1H), 6.27 (d, J=17.2 Hz, 1H), 6.11 (s, 1H), 5.67 (d, J=10.4 Hz, 1H), 3.96 (s, 6H), 3.68 (m, 4H), 3.54 (m, 4H), 2.78-2.82 (m, 2H), 2.61-2.64 (m, 2H), 2.43 (m, 6H), 2.33 (s, 6H), 1.92-1.95 (m, 2H).

LC-MS: ESI [M+H]$^+$=644.2/646.2.

Embodiment 11: 1-(4-(3-(6-(2,6-dichloro-3,5-dimethoxyaniline)-2-((tetrahydrofuran-3-yl)methyl)amino)imidazo[1',2':1,6]pyrido[2,3-d]pyrimidin-8-yl)propyl)piperazine-1-yl)prop-2-en-1-one

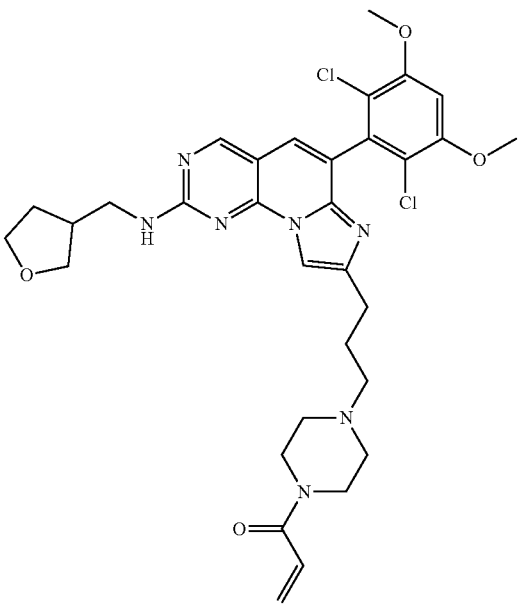 [SMILES: C=CC(=O)N1CCN(CCCc2cn3c(n2)c(-c2c(Cl)c(OC)cc(OC)c2Cl)cc2cnc(NCC4CCOC4)nc23)CC1]

LC-MS: ESI [M+H]$^+$=654.3/656.3.

Embodiment 12: 1-(4-(3-(6-(2,6-dichloro-3,5-dimethoxyaniline)-2-((2-hydroxy-2-methylpropyl)amino) imidazo[1',2':1,6]pyrido[2,3-d]pyrimidin-8-yl)propyl)piperazine-1-yl)prop-2-en-1-one

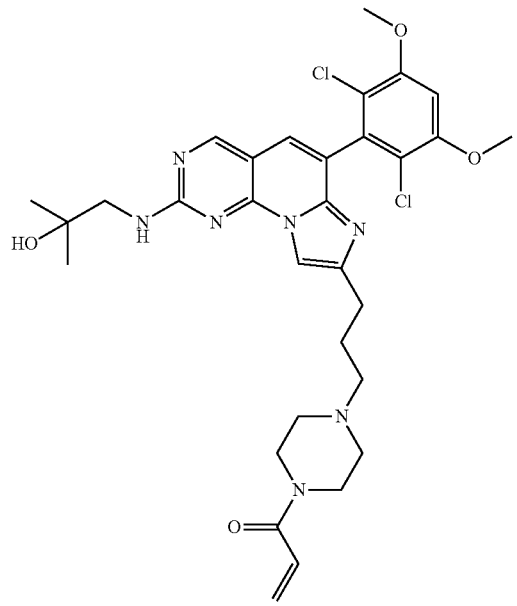 [SMILES: C=CC(=O)N1CCN(CCCc2cn3c(n2)c(-c2c(Cl)c(OC)cc(OC)c2Cl)cc2cnc(NCC(C)(C)O)nc23)CC1]

LC-MS: ESI [M+H]$^+$=642.3/644.3.

Embodiment 13: 3-((8-(3-(4-arcyloylpiperazine-1-yl)propyl-(6-(2,6-dichloro-3,5-dimethoxyaniline)imidazo[1',2':1,6]pyrido[2,3-d]pyrimidin-2-yl)amino)propanenitrile

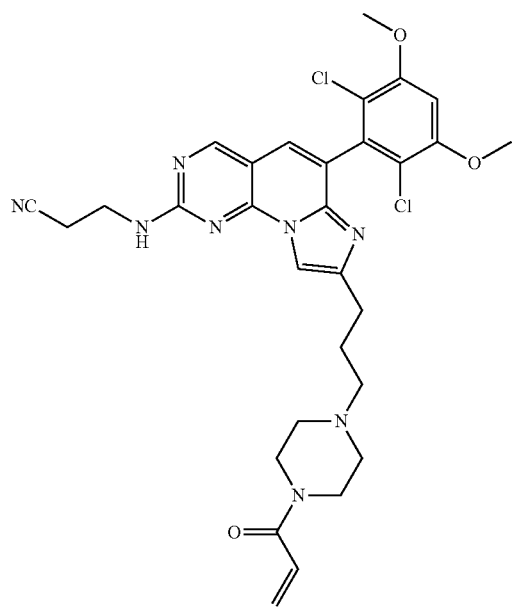 [SMILES: C=CC(=O)N1CCN(CCCc2cn3c(n2)c(-c2c(Cl)c(OC)cc(OC)c2Cl)cc2cnc(NCCC#N)nc23)CC1]

LC-MS: ESI [M+H]$^+$=623.2/625.2.

Embodiment 14: 1-(4-(3-(6-(2,6-dichloro-3,5-dimethoxyaniline)-2-(methylamine)imidazo[1',2':1,6]pyrido[2,3-d]pyrimidin-8-yl)-2,2dimethylpiperazine-1-yl)prop-2-en-1-one

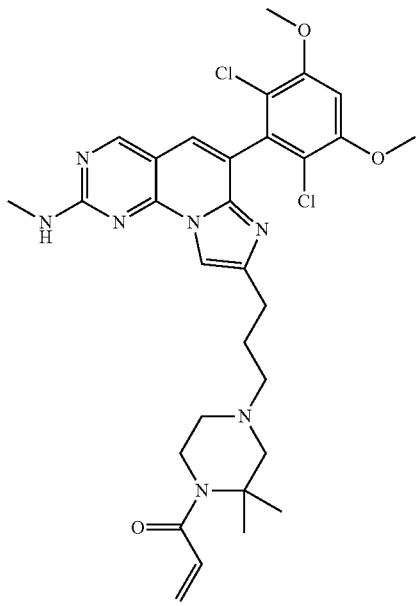

LC-MS: ESI [M+H]$^+$=612.4/614.4.

Embodiment 15: 1-(4-(3-(6-(2,6-dichloro-3,5-dimethoxyaniline)-2-(methylamine)imidazo[1',2':1,6]pyrido[2,3-d]pyrimidin-8-yl)-2,2-dimethylpropyl)piperazine-1-yl)prop-2-en-1-one

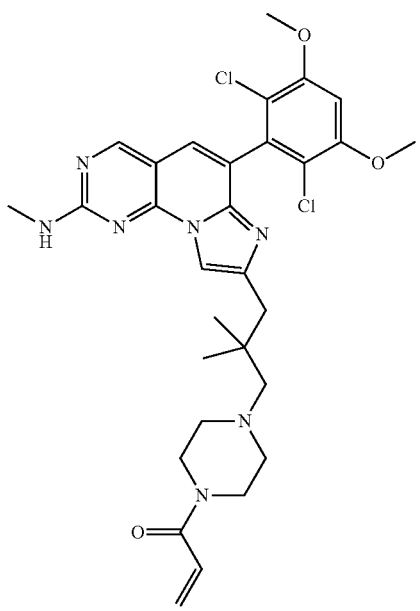

LC-MS: ESI [M+H]$^+$=612.3/614.3.

Embodiment 16: 1-(4-((6-(2,6-dichloro-3,5-phenyldimethoxyphenyl)-2-(methylamine)imidazo[1',2':1,6]pyrido[2,3-d]pyrimidin-8-yl)methyl)piperazine-1-yl)acrylamide

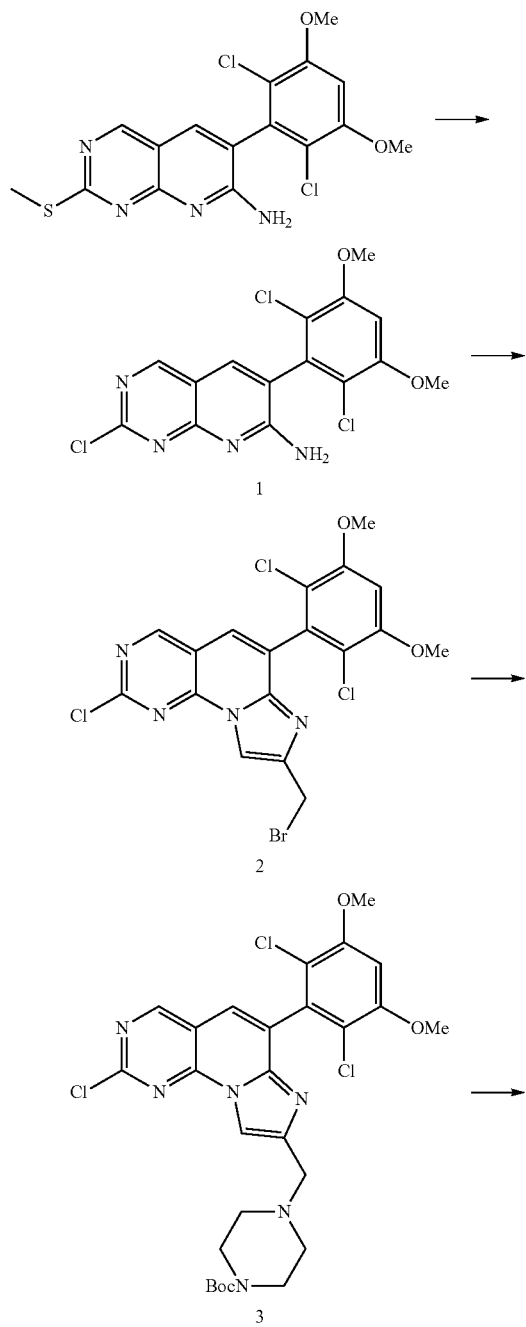

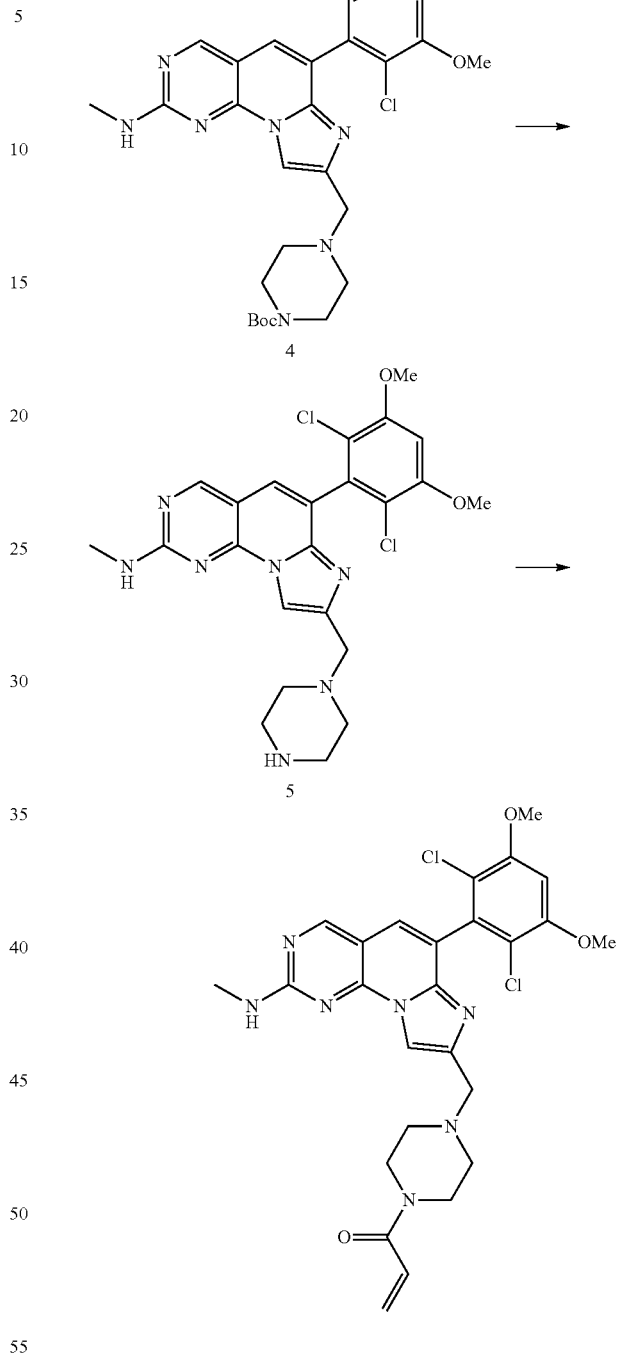

Step 1: 6-(2,6-dichloro-3,5-dimethoxy-phenyl)-2-methylthio-pyrido[2,3-d]pyrimidin-7-ylamine (3 mmol) was dissolved in anhydrous tetrahydrofuran (15 mL), sulfonyl chloride (2.54 mL, 30 mmol) was added thereto under ice bath cooling, and the reaction was carried out at room temperature for 1 hour. After the reaction was completed, saturated sodium bicarbonate aqueous solution was slowly added to the reaction mixture to quench the reaction, then the resulting mixture was extracted with dichloromethane, the organic phase was dried over anhydrous sodium sulfate, filtered, and the solvent was removed evaporation. The residue was purified by silica gel column chromatography to give the intermediate 2-chloro-6-(2,6-dichloro-3,5-dimethoxyphenyl)pyrido[2,3-d]pyrimidin-7-amine (640 mg). LC-MS: 385.1/387.1. ¹H-NMR (400 MHz, CDCl₃) δ 8.80 (s, 1H), 7.69 (s, 1H), 6.67 (s, 1H), 3.97 (s, 6H).

Step 2: The above intermediate (500 mg) was dissolved in anhydrous N,N-dimethylformamide (10 mL), then 1,3-dibromoprop-2-one (1.1 eq) was added at room temperature, the resulting mixture was stirred at 80° C. until the reaction was completed. The reaction mixture was extracted with dichloromethane, washed with saturated sodium bicarbonate and water sequentially, dried over anhydrous sodium sulfate, filtered, and concentrated under reduced pressure. The crude product was directly used in the next step without purification.

Step 3: The crude product was dissolved in anhydrous N,N-dimethylformamide (10 mL), then N-Boc-piperazine (1.1 eq) was added under ice bath cooling, the resulting mixture was stirred at room temperature for 2 hours, then the reaction was completed. The mixture was extracted with dichloromethane, washed with saturated sodium bicarbonate and water sequentially, dried over anhydrous sodium sulfate, filtered, concentrated under reduced pressure. The residue was purified by column chromatography to give the intermediate 4. LC-MS: 602.1/604.1.

Step 4 to Step 6: The embodiment compound 16 was synthesized according to the methods described in general methods 3-5.

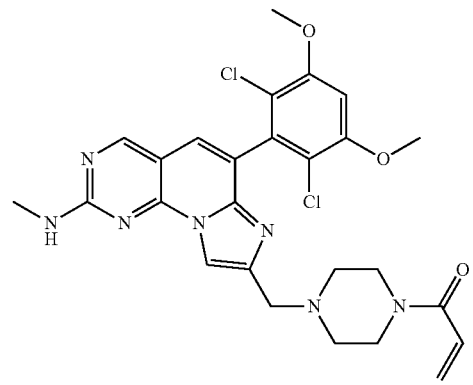 [SMILES: C=CC(=O)N1CCN(Cc2cn3c(n2)c(-c2c(Cl)c(OC)cc(OC)c2Cl)cc2cnc(NC)nc23)CC1]

LC-MS: ESI [M+H]⁺=556.2/558.2.

Embodiment 17: N-(4-(6-(2,6-dichloro-3,5-phenyldimethoxyphenyl)-2-(methylamine)imidazo[1',2':1,6]pyrido[2,3-d]pyrimidin-8-yl)phenyl)acrylamide

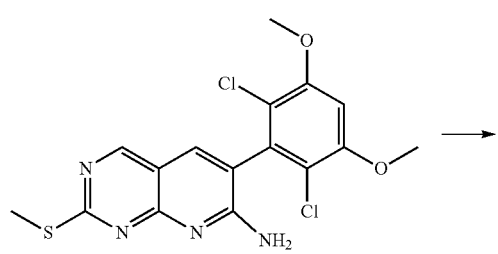

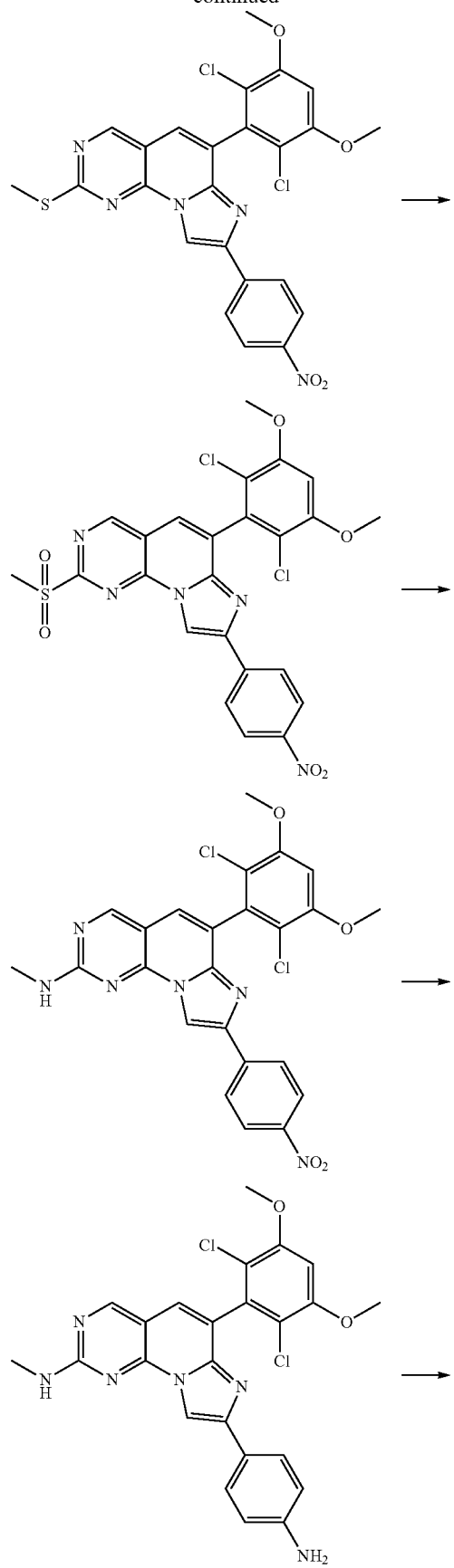

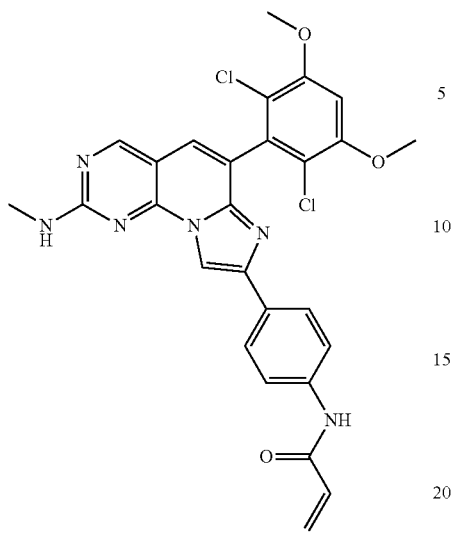

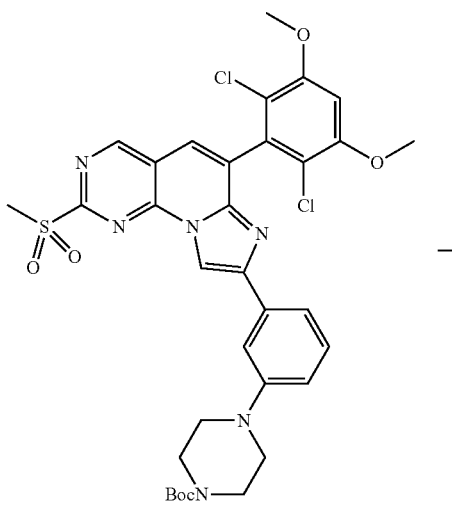

p-Nitro-2-bromoacetophenone was used instead of methyl 5-chloro-4-oxo-valerate, the cyclized product 6-(2,6-dichloro-3,5-dimethoxyphenyl)-2-(methylthio)-8-(4-nitrophenyl)imidazo[1',2':1,6]pyrido[2,3-d]pyrimidine was synthesized according to the same method as in the first step of intermediate 5, LC-MS: ESI [M+H]$^+$=542.4/544.4.

Then the intermediate 8-(4-aminophenyl)-6-(2,6-dichloro-3,5-dimethoxyphenyl)-N-methylimidazo[1',2':1,6]pyrido[2,3-d]pyrimidin-2-amine was prepared by the method of methylthio oxidation reaction in the second step, and the methylamine substitution reaction in the third step of the general preparation methods of the embodiments, LC-MS: ESI [M+H]$^+$=496.1/498.1.

The target compound, N-(4-(6-(2,6-dichloro-3,5-phenyldimethoxyphenyl)-2-(methylamine)imidazo[1',2':1,6]pyrido[2,3-d]pyrimidin-8-yl)phenyl)acrylamide, was synthesized by the method of acryloyl reaction in the fifth step of the general methods of the embodiments. LC-MS: ESI [M+H]$^+$=549.2/551.2, H-NMR (400 MHz, CD$_3$OD) 8.79 (s, 1H), 8.49 (s, 1H), 7.86 (d, J=8.0 Hz, 1H), 7.77 (s, 1H), 7.58 (d, J=7.2 Hz, 1H), 7.21 (s, 1H), 6.62 (s, 1H), 6.36-6.40 (m, 1H), 6.18-6.20 (m, 1H), 5.62-5.70 (m, 2H), 3.96 (s, 6H), 3.20 (d, J=4.8 Hz, 3H).

Embodiment 18: 1-(4-(3-(6-(2,6-dichloro-3,5-dimethoxyphenyl)-2-(methylamine)imidazo[1',2':1,6]pyrido[2,3-d]pyrimidin-8-yl)phenyl)piperazine-1-yl)acrylamide

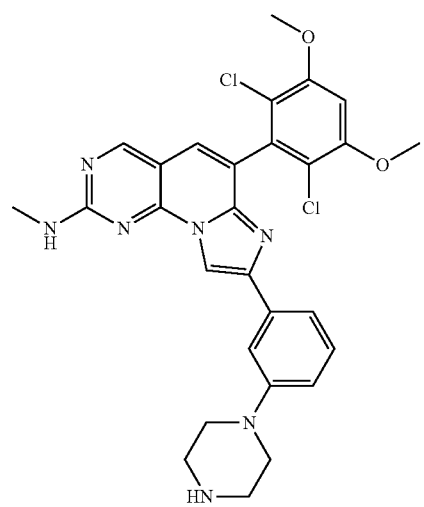

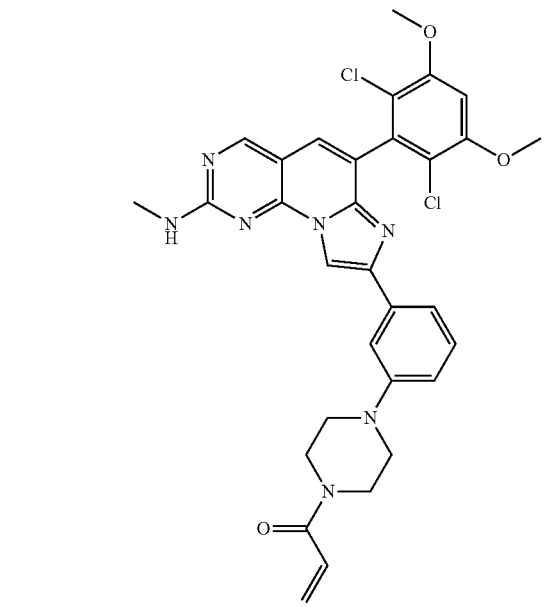

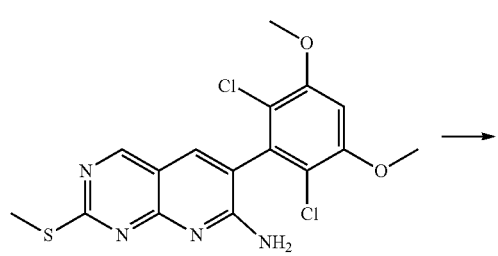

Tert-butyl-4-(3-(2-bromoacetyl)phenyl)piperazine-1-formate was used instead of methyl 5-chloro-4-oxo-valerate, and the target compound was synthesized by the same method as in Embodiment 17. LC-MS: ESI [M+H]$^+$=618.2/620.2.

Embodiment 19: N-(3-(6-(2,6-dichloro-3,5-dimethoxyphenyl)-2-(methylamino)imidazo[1',2':1,6]pyrido[2,3-d]pyrimidin-8-yl)benzyl)acrylamide

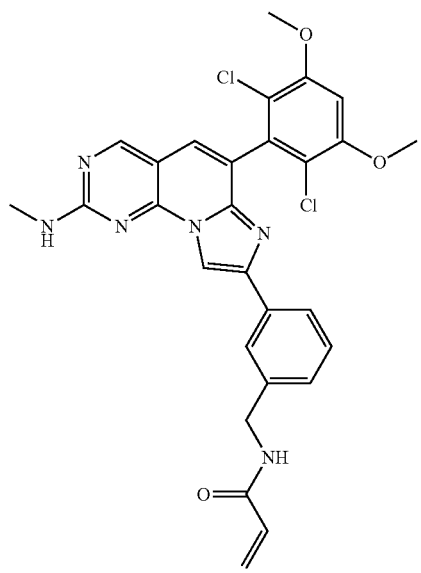

Tert-butyl (3-(2-bromoacetyl)benzyl)formate was used instead of methyl 5-chloro-4-oxo-valerate, the target product was prepared according to the same method as in Embodiment 17. LC-MS: ESI [M+H]$^+$=563.1/565.1.

Test Example 1: Determination of Inhibitory Activities of Compounds of the Present Disclosure on Kinases FGFR1 and FGFR4

(1). Preparation of 1×Kinase buffer; (2) Preparation of the gradient concentrations of the compounds: the concentration of the compounds to be tested started from 10 µM, which was 3-fold diluted to prepare 10 dilutions, and then tested in duplicated wells. The compounds were 100-fold serially diluted into 10 dilutions with different final concentrations in 96-well plates, each of which was further diluted with 1×Kinase buffer to prepare an intermediate dilution having a concentration of 5 times the final concentration; (3) adding 5 µL of each of the prepared compound solution into the compound wells of 384-well plates, and each concentration set single well; adding 5 µL of 5% DMSO into negative control wells and positive control wells respectively; (4) preparing a kinase solution having a concentration of 2.5 times the final concentration with 1×kinase buffer; (5) adding 10 µL of kinase solution at a concentration of 2.5 times the final concentration into the compound wells and the positive control wells respectively; and adding 10 µL of 1×Kinase buffer into the negative control wells; (6) centrifuging at 1000 rpm for 30 seconds, and incubating at room temperature for 10 minutes after shaking and mixing evenly; (7) preparing a mixed solution of ATP and Kinase substrate 22 having a concentration of 2.5 times the final concentration with 1×Kinase Buffer; (8) adding 10 µL of the mixed solution of ATP and substrate at a concentration of 2.5 times the final concentration to initiate the reaction; (9) Centrifuging the 384-well plates at 1000 rpm for 30 seconds, and incubating at 28° C. for corresponding time respectively after shaking and mixing; (10) adding 30 µL of stop detection solution to stop the kinase reaction, centrifuging at 1000 rpm for 30 seconds, and shaking and mixing the mixture evenly; (11) reading the conversion rate by Caliper Ezreader II. The dose-effect curve was fitted by the log (inhibitor) vs. response-variable slope of GraphPad Prism 5 with the log value of concentration as the X axis and the percentage inhibition rate as the Y axis, then the IC$_{50}$ value of each compound on the enzyme activity was obtained.

2. Results: Embodiments 1 to 19 provided by the present disclosure have better inhibitory activities on FGFR1 and FGFR4, the IC$_{50}$ values of the inhibitory activities, most of the embodiment compounds have IC$_{50}$ values less than 10 nM, and some embodiment compounds (e.g., Embodiment 3) even have IC$_{50}$ values less than 1 nM, showing stronger inhibitory activities. As shown in Table 1.

Test Example 2: Effect of the Compounds of the Present Disclosure on Proliferation Ability of Tumor Cells Mediated by FGFR 1. Test method: inoculating Hep3B cells (ATCC) in logarithmic growth phase at an appropriate density in a 96-well culture plate, with 100 µL per well. After overnight culture, different concentrations of compounds were added to stay for 72 hours, and menstruum control group (negative control) was set, and the incubation was performed under the condition of 5% CO$_2$ at 37° C. Adding 10 mM compound stock solution to the cells, after the cells were incubated with the compounds for 72 hours, the effects of the compounds on cell proliferation were determined by CellTiter-Glo (Promega) method. 30 µL CTG reagent was added to each well and the resulting mixtures were placed in a 37° C. incubator for 2-4 hours. Then the plate was read by a full-wavelength microplate enzyme reader Envision at a wavelength of 450 nm.

The inhibition rates (%) of the compounds on tumor cell growth were calculated by the following formula: inhibition rate (%)=(OD negative control well−OD administration well)/OD negative control well×100%. IC$_{50}$ values were obtained by four parameters regression using Graphpad Prism 5 software.

2. Results: All of the embodiment compounds 1-19 provided by the present disclosure have Hep3B cells inhibitory activities with IC$_{50}$ values less than 500 nM, most of the embodiment compounds have inhibitory activities with IC$_{50}$ values less than 50 nM, and some embodiment compounds (e.g., Embodiment 3) have inhibitory activities with IC$_{50}$ values even less than 10 nM, showing stronger cell proliferation inhibitory activities, as shown in Table 1.

TABLE 1

The inhibitory activities of the embodiment compounds 1-19 on FGFR1/FGFR4 kinases and Hep3B cell proliferation

| No. | FGFR1 IC$_{50}$ (nM) | FGFR4 IC$_{50}$ (nM) | Hep3B IC$_{50}$ (nM) |
| --- | --- | --- | --- |
| 1 | +++ | +++ | +++ |
| 2 | +++ | +++ | +++ |
| 3 | +++ | +++ | +++ |
| 4 | +++ | +++ | +++ |
| 5 | +++ | +++ | +++ |
| 6 | +++ | +++ | +++ |

TABLE 1-continued

The inhibitory activities of the embodiment compounds 1-19 on FGFR1/FGFR4 kinases and Hep3B cell proliferation

| No. | FGFR1 IC$_{50}$ (nM) | FGFR4 IC$_{50}$ (nM) | Hep3B IC$_{50}$ (nM) |
|---|---|---|---|
| 7  | +++ | +++ | ++  |
| 8  | +++ | +++ | +++ |
| 9  | +++ | +++ | ++  |
| 10 | +++ | +++ | ++  |
| 11 | +++ | +++ | ++  |
| 12 | +++ | +++ | ++  |
| 13 | +++ | +++ | ++  |
| 14 | +++ | ++  | ++  |
| 15 | +++ | ++  | ++  |
| 16 | +++ | +   | ++  |
| 17 | +++ | +   | ++  |
| 18 | +++ | +   | ++  |
| 19 | +++ | +   | ++  |
| 20 |     |     |     |

In Table 1, IC$_{50}$ <20 nM is indicated by "+++", 20 nM < IC$_{50}$ <200 nM is indicated by "++", IC$_{50}$ >200 nM is indicated by "+".

Test Example 3: Inhibitory Activities of the Embodiment Compounds on Different Kinases The inhibitory activities of the compounds of the present disclosure on different kinases such as EGFR, VEGFR, PDGFR, FGFR, RET, MET, Src, Lyn, Syk, MEK, CDK, RA, ROS, etc., were also determined. Some embodiment compounds (e.g., Embodiment 3 and Embodiment 17) exhibit better kinase selectivity, with a selectivity greater than 100 times.

Test Example 4: Proliferation Inhibitory Activities of the Embodiment Compounds on Different Tumor Cells SRB staining method or CCK8 method was used to test the proliferation inhibitory activity on various tumor cells, such as HuH-7, J-7, DM114, SNU-16, KG1, UM-UC-14, HCT 116, NCI-1H716, MCF-7, Colo-205, KMS 11, RT-112, OPM-2, NCI-H460, SNU-869, CNE, NCI-H2122, NCI-H1299, A549, MG63, Kappars-299, SK-OV-3, U87MG, BT474, LNCAP, A498, KYSE140, HUCC-T1, PANC-1, etc., some embodiment compounds (e.g., Embodiment 3 and Embodiment 17) exhibited stronger inhibitory activities on proliferation of different cells and better anti-tumor activities, with proliferation inhibitory activities less than 100 nM on various tumor cells.

Test Example 5: ADME-PK Test of the Embodiment Compounds (1) Metabolic stability test: 150 μL system of liver microsome (final concentration 0.5 mg/mL) was used for metabolic stability incubation, the system contained NADPH (final concentration 1 mM), 1 μM test compound and positive control Midazolam or negative control Atenolol, then the reaction was terminated with Tinidazole-containing acetonitrile at 0 min, 5 min, 10 min and 30 min respectively, and the mixtures were vortexed for 10 minutes and centrifuged for 10 minutes at 15000 rmp, 50 μL of the supernatants were added into 96-well plate for injection. The metabolic stability of the compounds was calculated by measuring the relative reduction of the original drug.

(2) Direct inhibition test (DI test): Direct inhibition incubation was carried out with 100 μL system of human liver microsome (final concentration 0.2 mg/mL), the system containing NADPH (final concentration 1 mM), 10 μM compound, positive inhibitor cocktail (Ketoconazole 10 μM, Quinidine 10 μM, Sulfaphenazolum 100 μM, α-Naphthoflavone 10 μM, Tranylcypromine 1000 μM), negative control (BPS containing 0.1% DMSO) and mixed probe substrates (Midazolam 10 μM, Testosterone 100 μM, Dextromethorphan 10 M, Diclofenac 20 μM, Phenacetin 100 μM, Mephenytoin 100 μM) was incubated for 20 minutes and then the reaction was terminated. The relative activity of enzymes was calculated by measuring the relative production of metabolites.

(3) LC/MS/MS method was used to measure the drug concentration in plasma at different time points after the embodiment compounds were administered to the rats or mice by intragastric administration and intravenous injection respectively, so as to study the pharmacokinetic behavior of the compounds of the present disclosure in rats or mice and evaluate the pharmacokinetic characteristics thereof. Experimental scheme: the experimental animals were healthy adult male SD rats or BALB/c mice, provided by Shanghai Sippr-Bk Laboratory Animals Co. Ltd; administration method and sample collection: SD rats or BALB/c mice were given the compounds by intravenous injection (suspensions of 3 mg/kg and 1 mg/mL of the compounds to be tested) and intragastric administration (suspensions of 10 mg/kg and 1 mg/mL of the compounds to be tested), respectively, and 0.4 mL of blood was taken from fundus venous plexus of the rats or mice before administration and on 2, 5, 15, 30, 60, 90, 120, 240, 360, 480 and 1440 min after administration; 50 μL of plasma sample was taken, and 200 μL of acetonitrile solution containing internal standard was added respectively to precipitate protein, the mixture was vortexed for 10 minutes and centrifuged at 6000 rpm/min for 10 minutes; 200 μL of the supernatant was centrifuged again at 6000 rpm for 10 minutes; then 75 μL of the supernatant was taken, diluted with gradient initial mobile phase, and centrifuged at 6000 rpm for 10 minutes; finally, 70 μL of the supernatant was added into a 96-well plate for injection, the injection volume was 5 μL for LC-MS-MS analysis.

2. Some embodiment compounds (e.g., Embodiment 3 and Embodiment 17) exhibit better ADME properties and good absorption and metabolism properties in rats and mice, and AUC/Cmax and other indicators demonstrate excellent druggability of the compounds.

Test Example 6: Inhibitory Effect of the Embodiment Compounds on Xenograft Tumors Growth in Nude Mice 1. The tumor tissue in vigorous growth period was cut into about 1.5 mm$^3$, and subcutaneously inoculated into the right armpit of nude mice under sterile condition. The diameter of the subcutaneous transplanted tumors in nude mice was measured with vernier caliper, and the animals were randomly divided into groups when the average volume of the tumor reached about 130 mm$^3$. The embodiment compounds (prepared to the desired concentration with water for injection containing 1% Tween 80 for later use) were orally administered at a predetermined dose every day for three weeks, while a same amount of menstruum was administered in the menstruum control group. During the whole experiment, the diameter of the xenograft tumor was measured twice a week and the weight of the mice was weighed at the same time. The tumor volume (TV) was calculated by the formula: $TV = \frac{1}{2} \times a \times b^2$, where a and b represent length and width respectively. According to the measured results, the relative tumor volume (RTV) was calculated by the formula: RTV=Vt/V0, where V0 was the tumor volume measured when the mice were divided into cages for administration (i.e., d0) and Vt was the tumor volume at each measurement. The evaluation index of anti-tumor activity was 1) relative tumor proliferation rate T/C (%), which was calculated by the formula: T/C (%)=(TRTV/CRTV)×100%, TRTV: RTV in the treatment group; CRTV: RTV in the negative control group; 2) tumor volume growth inhibition rate GI %, which was calculated by the formula: GI %=[1−(TVt−TV0)/(CVT−CT0)]×100%, where TVt was the tumor volume measured at each time in the treatment group; TV0 is the tumor volume measured when the mice were divided into cages for administration in the treatment group; CVt was the tumor volume measured at each time in the control group; CV0 was the tumor volume measured when the mice were divided into cages for administration in the control group; 3) tumor weight inhibition rate, which was calculated by the formula: tumor weight inhibition rate %=(Wc−WT)/WC×100%, Wc: tumor weight in the control group, WT: tumor weight in the treatment group.

2. Some embodiment compounds (e.g., Embodiment 3 and Embodiment 17) exhibit better anti-tumor effect in nude mice, and the anti-tumor rate can reach more than 80% at a lower dose (even less than 20 mg/kg).

Although specific embodiments of the present disclosure are described above, those skilled in the art should understand that these are merely examples for illustration and various changes or modifications can be made to the embodiments without departing from the principles and essence of the present disclosure. Therefore, the scope of protection of the present invention is defined by the appended claims.

What is claimed is:

1. A compound represented by formula (I), or a pharmaceutically acceptable salt thereof, or an enantiomer, diastereomer, or tautomer thereof,

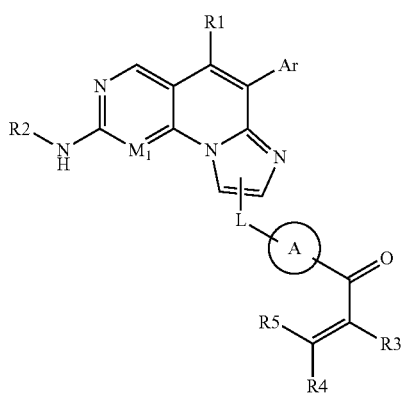

(I)

wherein:
$R_1$ is hydrogen, halogen, $C_1$-$C_3$ alkyl, or cyano;
$R_2$ is hydrogen, $C_1$-$C_{10}$ alkyl, 3-8 membered cycloalkyl or heterocycloalkyl, or 5-8 membered aryl or heteroaryl;
each of $R_3$, $R_4$ and $R_5$ is independently hydrogen, halogen, cyano, alkyl, sulfuryl, sulfinyl, acyl, sulfonyl, or nitro;
$M_1$ is $CR_6$ or N;
$R_6$ is hydrogen, halogen, or $C_1$-$C_3$ alkyl;
Ar is 5-6 membered aryl or heteroaryl;
L is a chemical bond, $C_1$-$C_{10}$ alkyl, alkenyl, alkynyl, alkoxyl, alkylthio, alkylamino, acyl, sulfonyl, 4-8 membered cycloalkyl or heterocycloalkyl, or 5-10 membered aryl or heteroaryl;
A is 4-8 membered cycloalkyl or heterocycloalkyl, or 5-10 membered aryl or heteroaryl;
one or more hydrogen atoms in each of the above groups are optionally substituted by the substituent independently selected from the group consisting of deuterium, halogen, hydroxyl, amino, cyano, sulfuryl or sulfinyl, $C_1$-$C_8$ alkyl, $C_3$-$C_8$ cycloalkyl, $C_1$-$C_8$ alkoxyl, $C_1$-$C_8$ alkylamino, $C_2$-$C_6$ alkenyl, $C_2$-$C_6$ alkynyl, $C_2$-$C_6$ acyl or sulfonyl, 5-8 membered aryl or heteroaryl, 4-8 membered saturated cycloalkyl and heterocycloalkyl;
or, $R_2$ is $N(CH_3)_2C(=O)CH_2—$ or $N(R_7)(R_8)—(CH_2)_z—$; each of $R_7$ and $R_8$ is independently hydrogen or $C_1$-$C_6$ alkyl, z is 1, 2, 3 or 4;
or, each of $R_3$, $R_4$ and $R_5$ is independently $N(R_9)(R_{10})—(CH_2)_p—$; wherein $R_9$ and $R_{10}$ are both $C_1$-$C_6$ alkyl, p is 1 or 2;
wherein, the heteroaryl comprises 1-3 heteroatoms independently selected from the group consisting of N, O, P and S; the heterocycloalkyl comprises 1-3 heteroatoms independently selected from the group consisting of N, O, P and S.

2. The compound represented by formula (I), or the pharmaceutically acceptable salt thereof, or the enantiomer, diastereomer, or tautomer thereof according to claim 1, wherein,
in the formula,
$M_1$ is CH or N;
and/or, $R_1$ is hydrogen, halogen, or $C_1$-$C_3$ alkyl;
and/or, $R_2$ is hydrogen, $C_1$-$C_6$ alkyl, $C_1$-$C_6$ deuterated alkyl, $C_1$-$C_6$ haloalkyl, 5-8 membered aryl or heteroaryl, 4-6 membered cycloalkyl or heterocycloalkyl-$(CH_2)x-$, $O(R_6)—(CH_2)y-$, $N(R_7)(R_8)—(CH_2)z-$, $N(CH_3)_2C(=O)CH_2—$, $HOC(CH_3)_2CH—$ or $CH(CH_2OH)_2—CH_2—$; each of $R_6$, $R_7$ and $R_8$ is independently hydrogen or $C_1$-$C_6$ alkyl; each of x is independently 0, 1, 2, 3 or 4; each of y and z is independently 1, 2, 3 or 4;
and/or, each of $R_3$, $R_4$ and $R_5$ is independently hydrogen, halogen or $N(R_9)(R_{10})—(CH_2)p-$; wherein $R_9$ and $R_{10}$ are both $C_1$-$C_6$ alkyl, p is 1 or 2;
and/or, Ar is phenyl;
and/or, L is a chemical bond, $—(CH_2)_d—$, $—(CH_2)_e—CH=CH—$, or $—O—(CH_2)_n—$, wherein d is 1, 2 or 3, e is 1 or 2, n is 1, 2, 3 or 4;
and/or, A is 5-6 membered heterocycloalkyl, 5-6 membered heteroaryl-NH—, -Ph-$(CH_2)_o$—NH—, or 5-6 membered heteroaryl-$(CH_2)_m$-5-6 membered heterocycloalkyl-; wherein o is 0 or 1;
wherein, L is invariably connected to the side of aryl, heteroaryl or non-fatty amino in the structure of A.

3. The compound represented by formula (I), or the pharmaceutically acceptable salt thereof, or the enantiomer, diastereomer, or tautomer thereof according to claim 2, wherein,
in the formula,
$R_2$ is H, methyl, $—CD_3$, $—CH_2C(CH_3)_2F$, $N(CH_3)_2C(=O)CH_2—$, $HOC(CH_3)_2CH—$, $CH(CH_2OH)_2—CH_2—$,

,

CH₃OCH₂CH₂—,
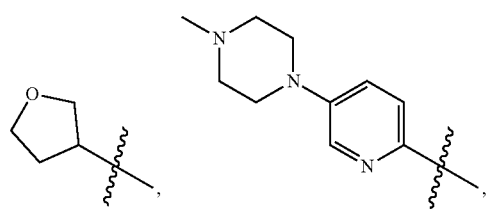
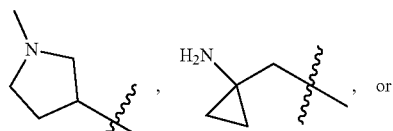
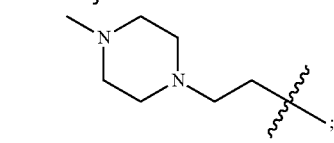
and/or, L is a chemical bond, —CH₂—, —CH₂CH₂—, —CH₂CH₂CH₂—, —CH₂—CH=CH—, or —O—CH₂CH₂—;
and/or, A is
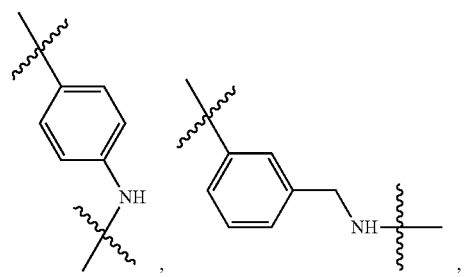
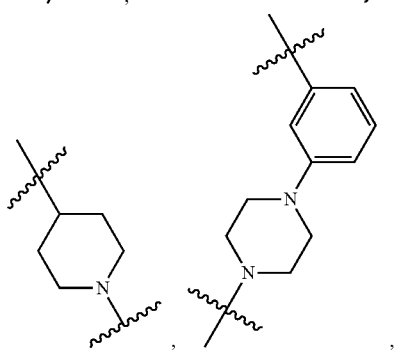
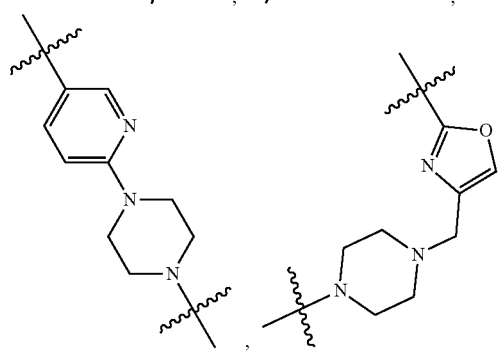
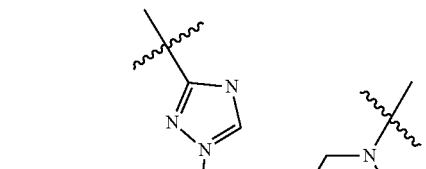
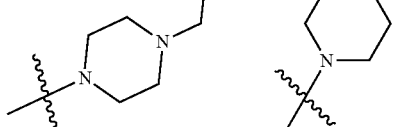
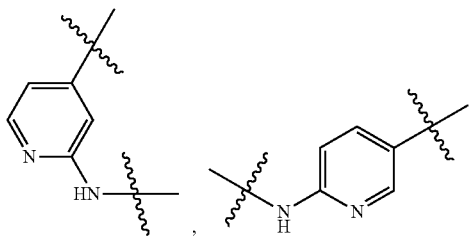
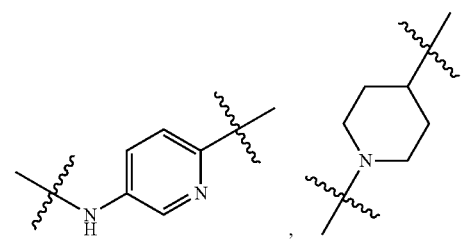
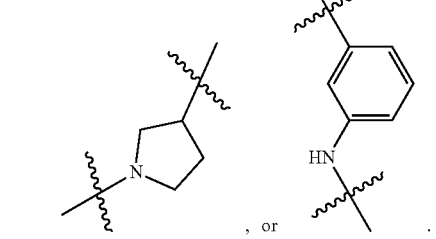, or 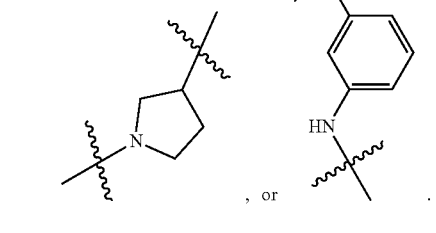.
4. The compound represented by formula (I), or the pharmaceutically acceptable salt thereof, or the enantiomer, diastereomer, or tautomer thereof according to claim 1, wherein,
the compound represented by formula (I) has a structure of:

69
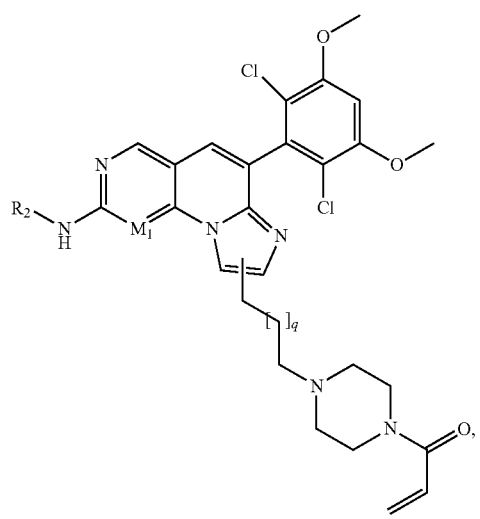
, or
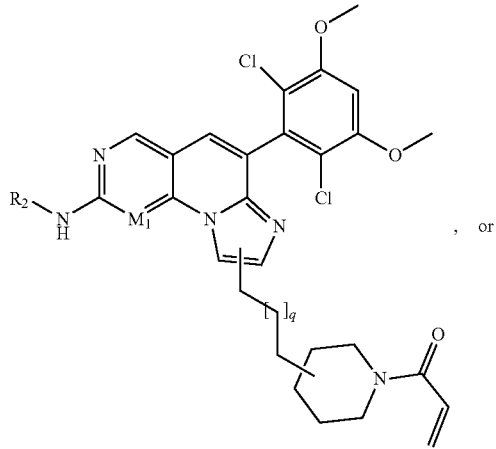
, or
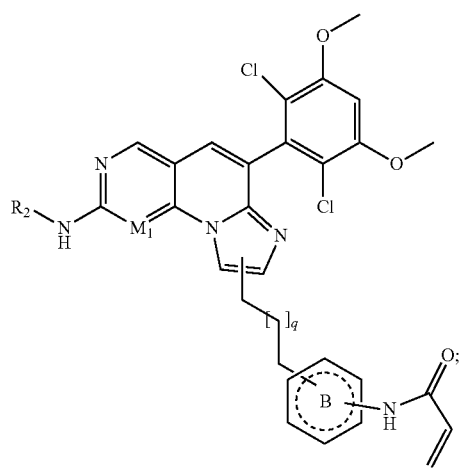
70
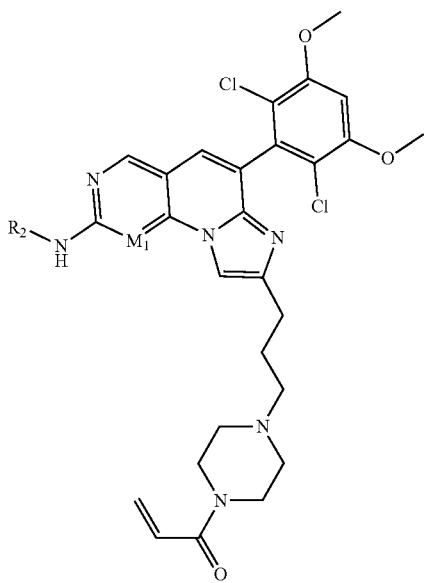
wherein, q is 0, 1 or 2, $M_1$ and $R_2$ are as defined in claim 1; ring B is 5-10 membered aromatic ring or aromatic heterocyclic ring.
5. The compound represented by formula (I), or the pharmaceutically acceptable salt thereof, or the enantiomer, diastereomer, or tautomer thereof according to claim 1, wherein,
the compound represented by formula (I) has a structure of:
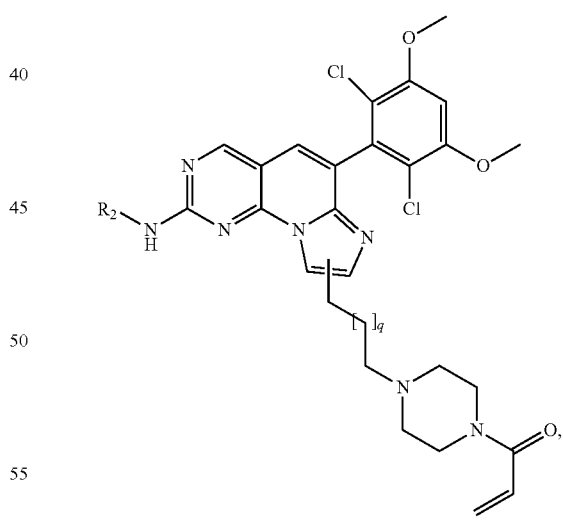

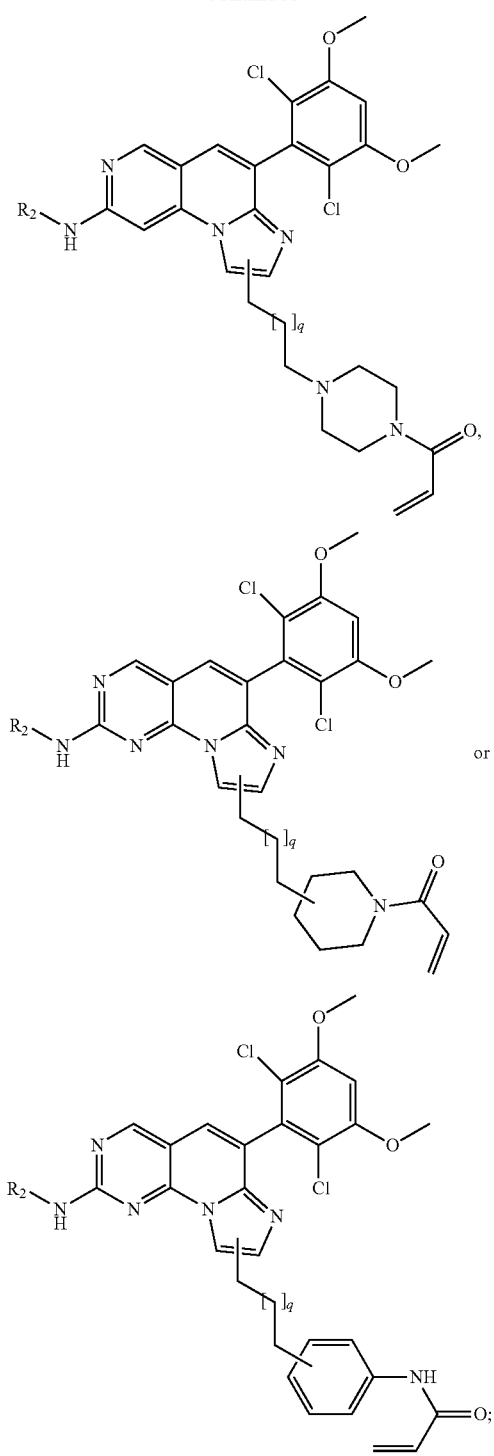
wherein, q is 0, 1 or 2, R₂ is as defined in claim 1
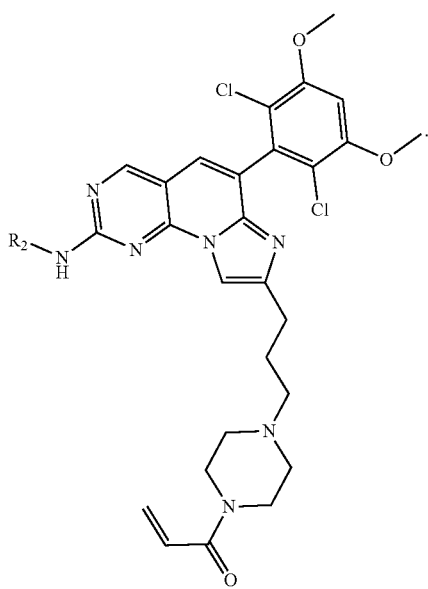
6. The compound represented by formula (I), or the pharmaceutically acceptable salt thereof, or the enantiomer, diastereomer, or tautomer thereof according to claim 1, wherein,
the compound represented by formula (I) is selected from the group consisting of:
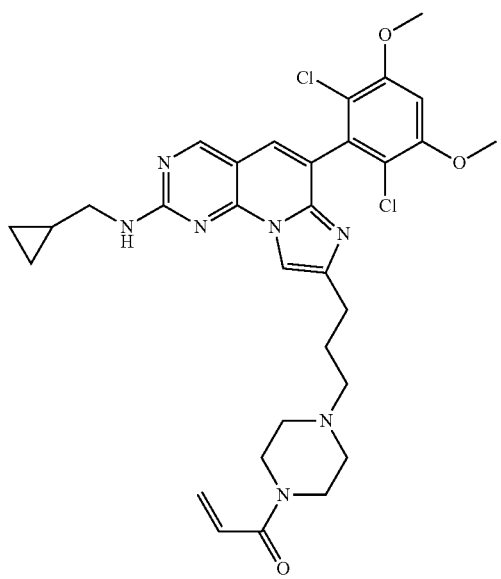

73
-continued
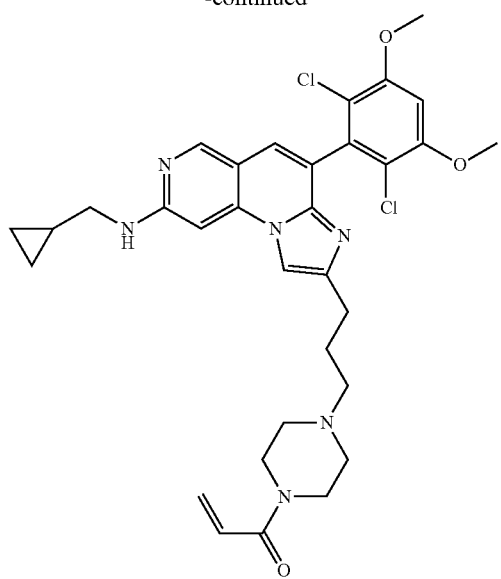
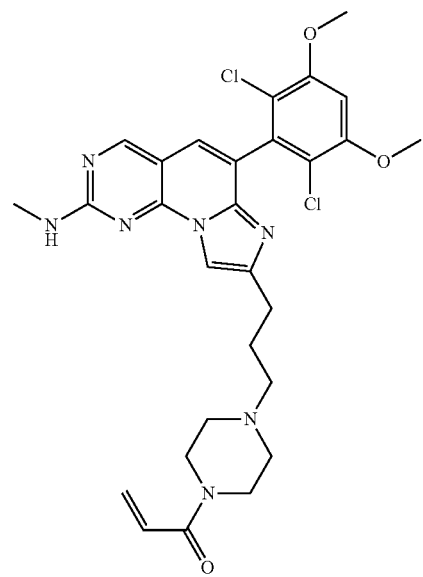
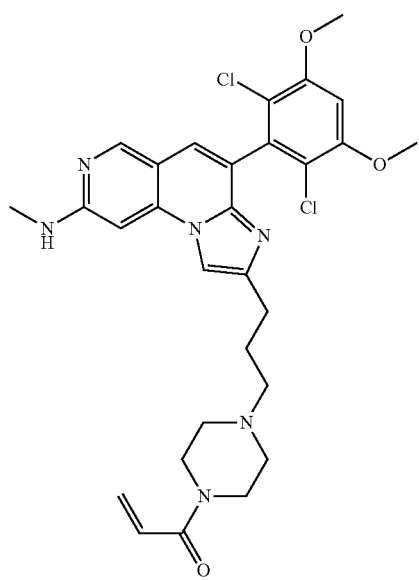
74
-continued
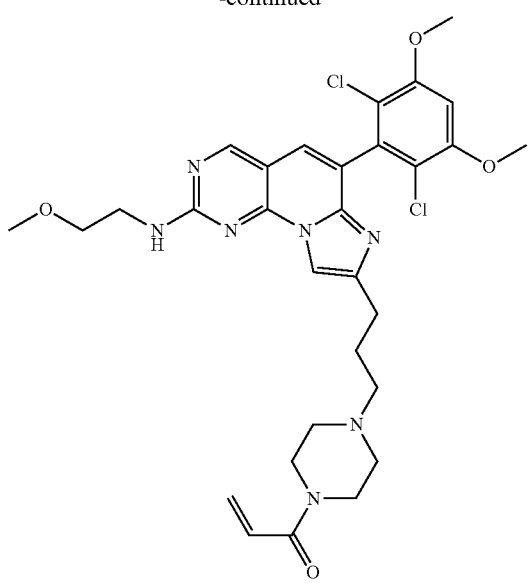
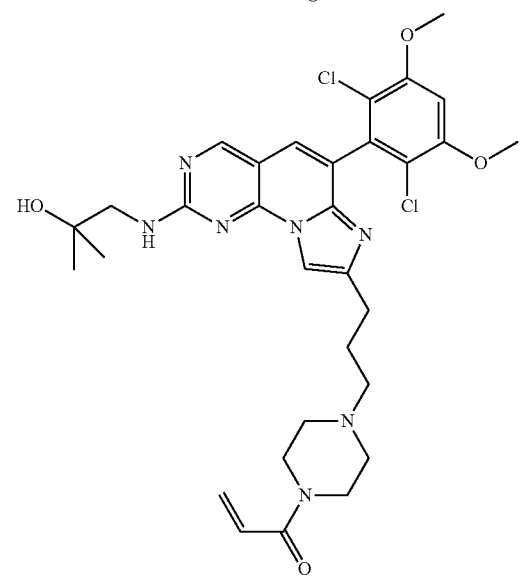
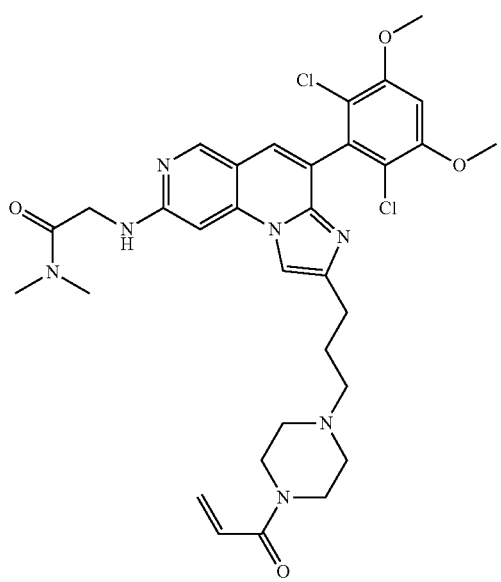

75
-continued
76
-continued
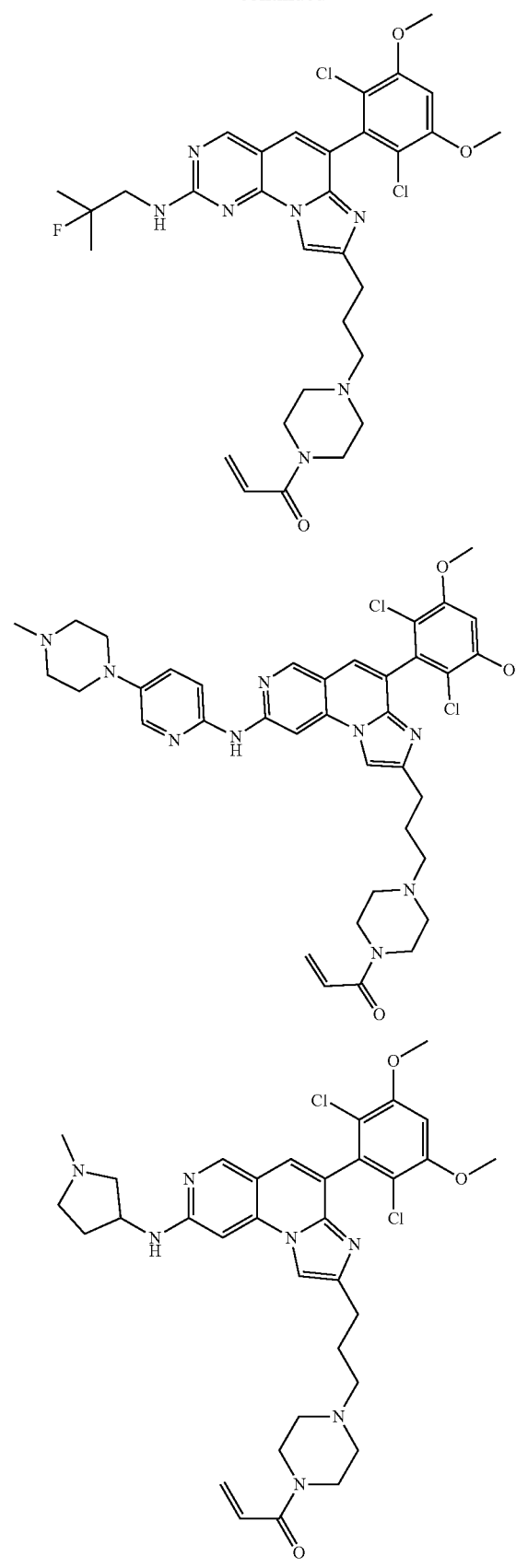
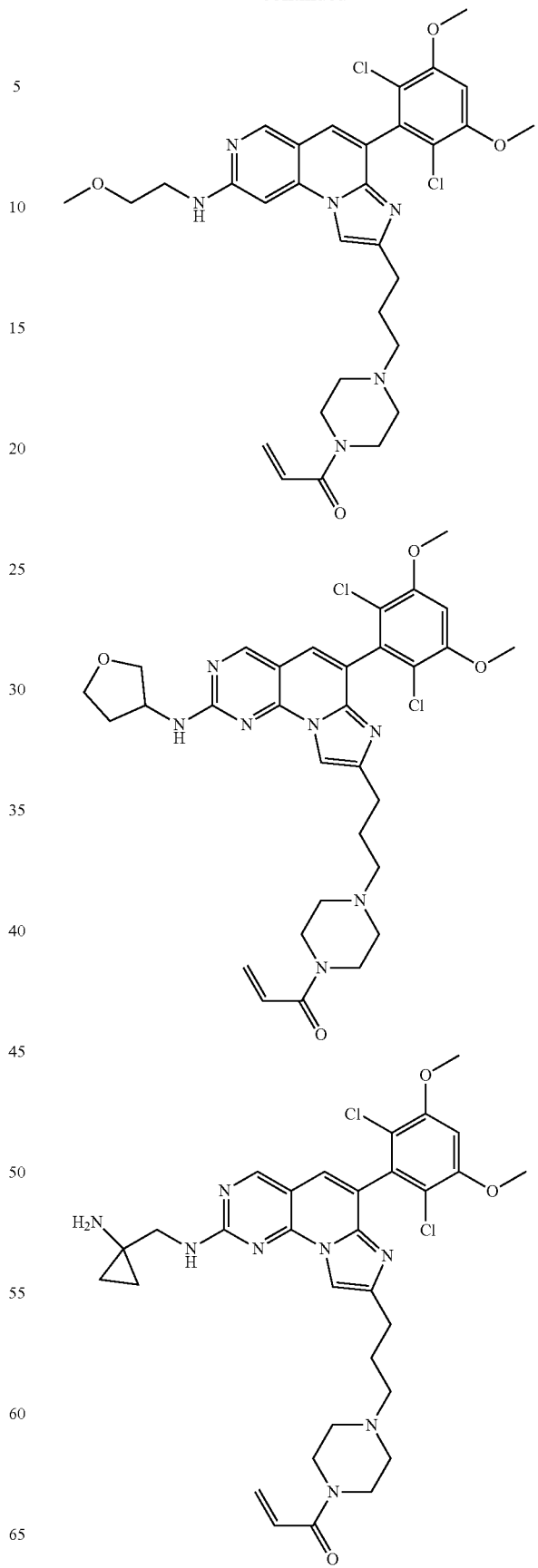

77
-continued
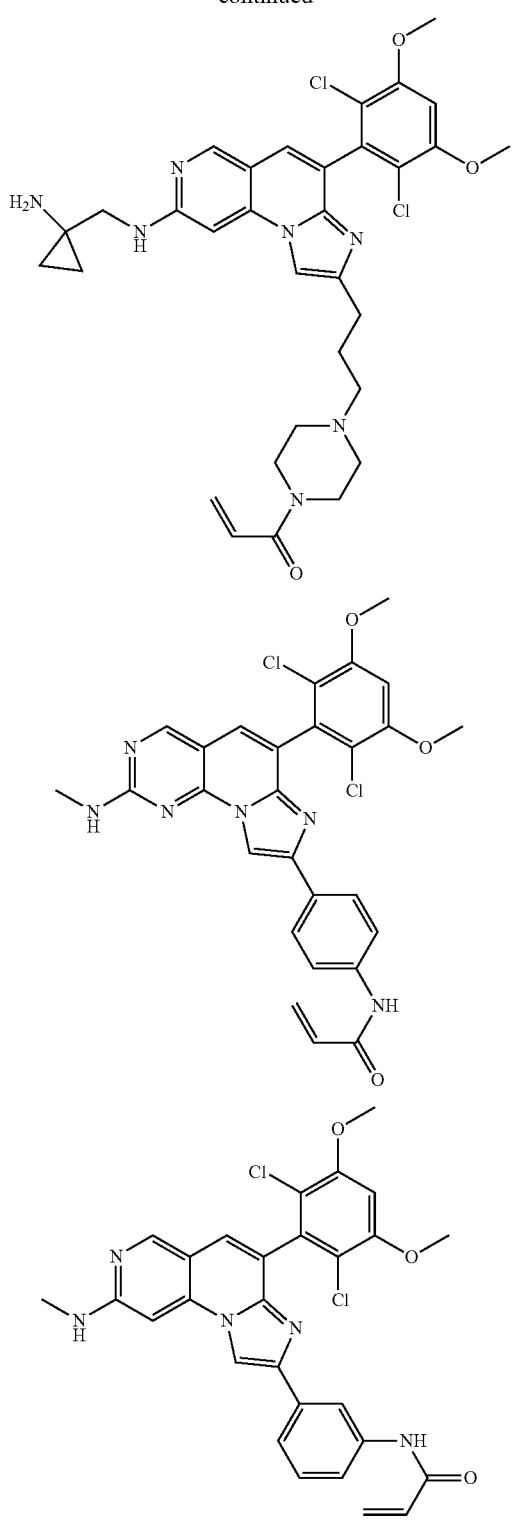
78
-continued
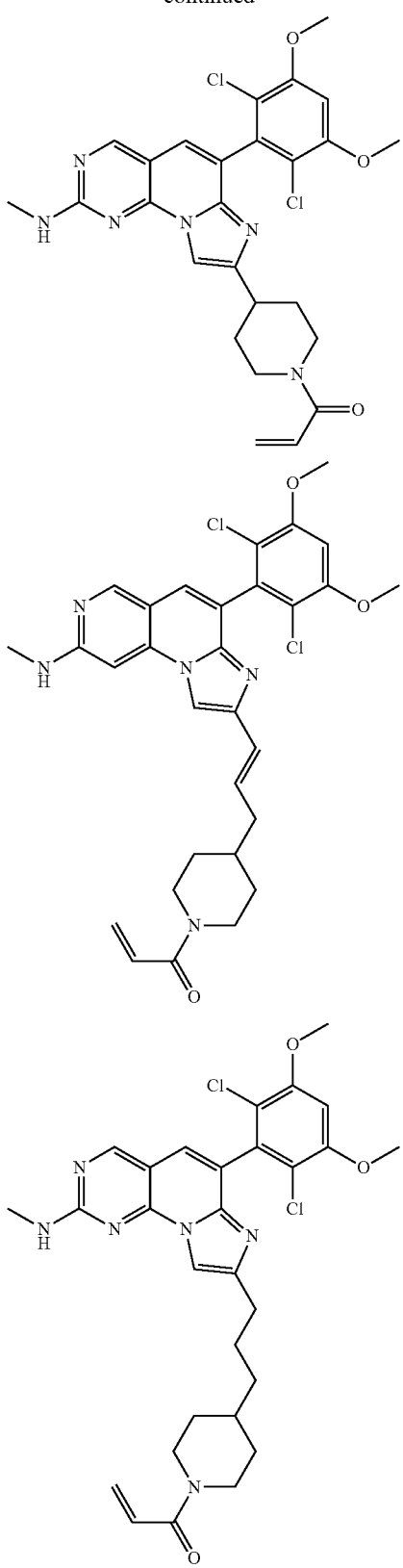

79
-continued
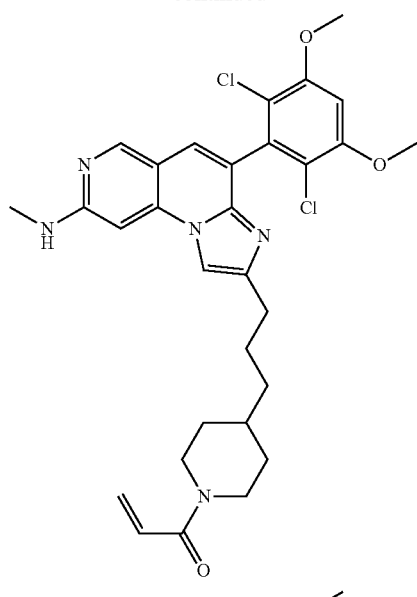
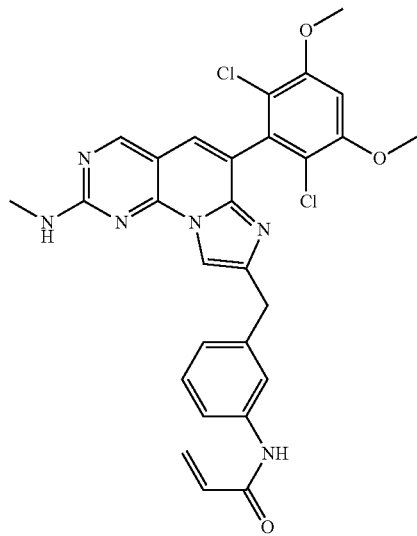
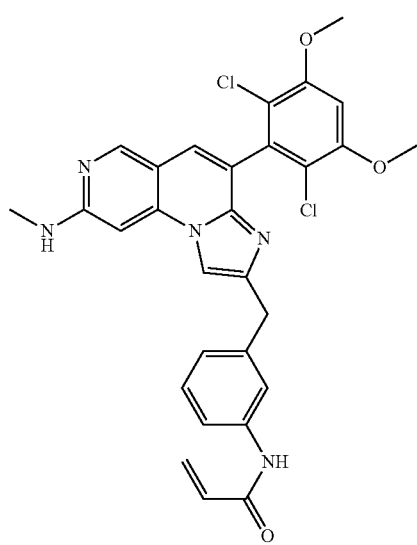
80
-continued
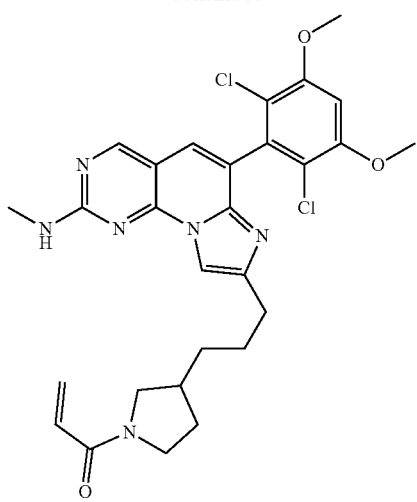
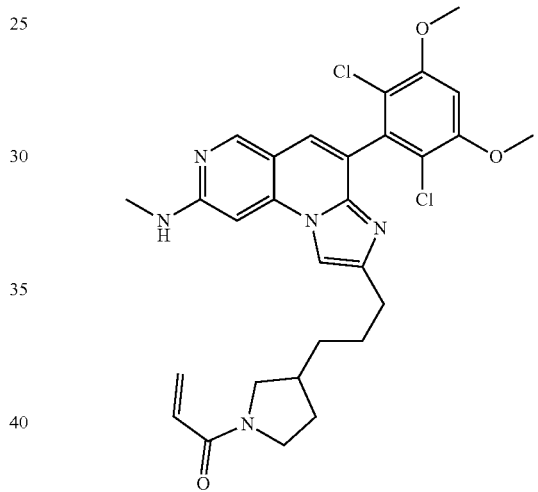
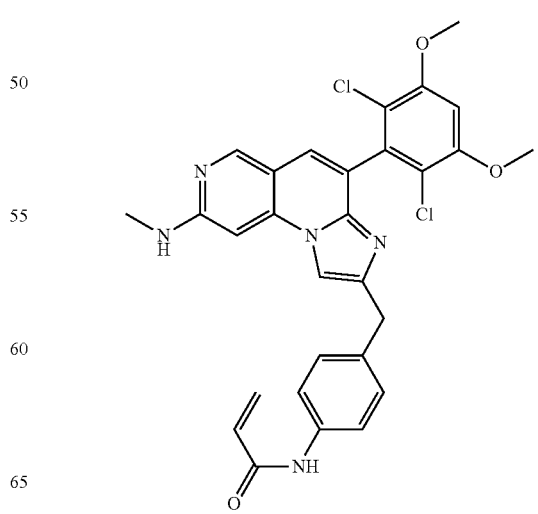

81
-continued
82
-continued
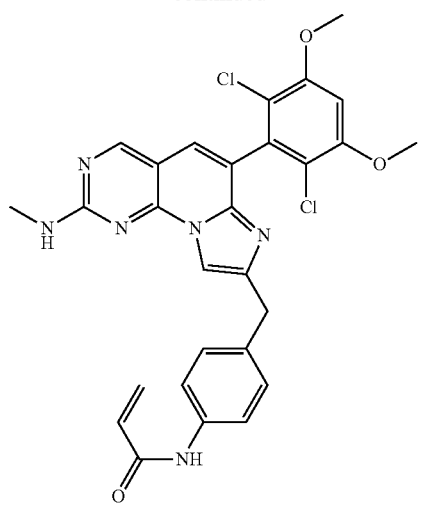
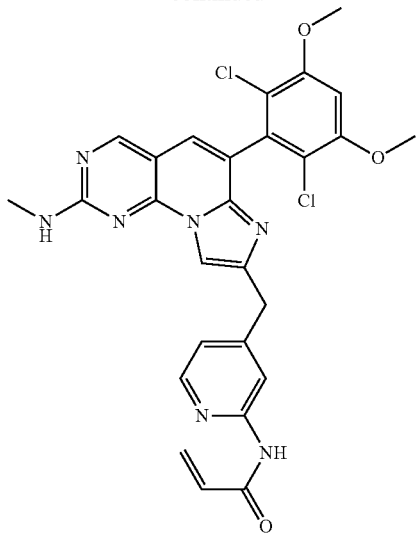

83
-continued
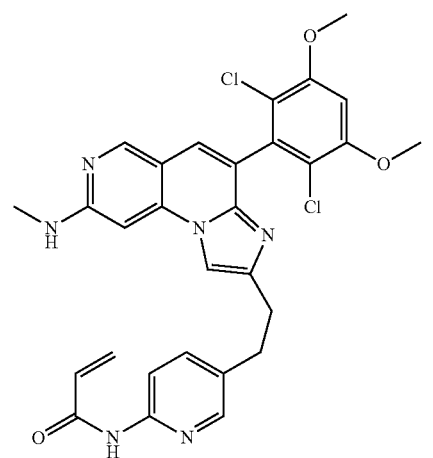
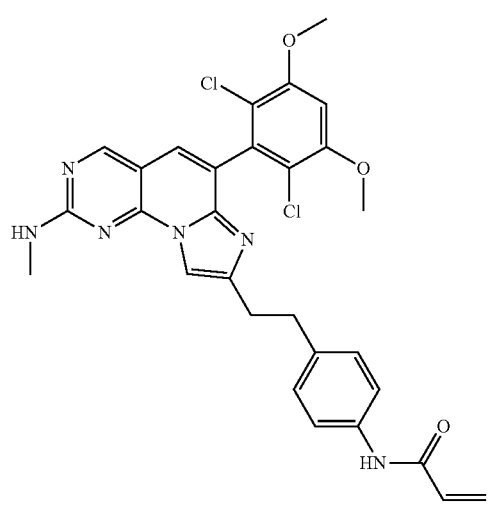
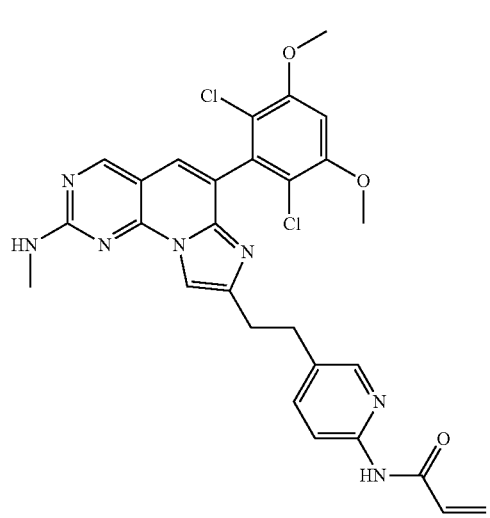
84
-continued
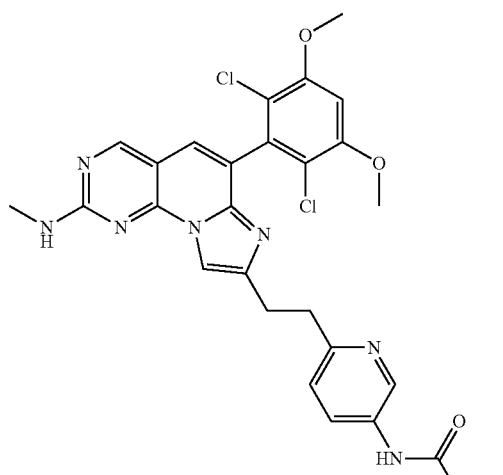
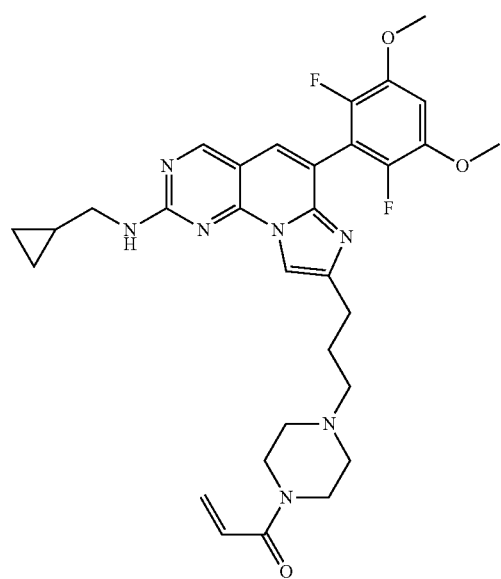
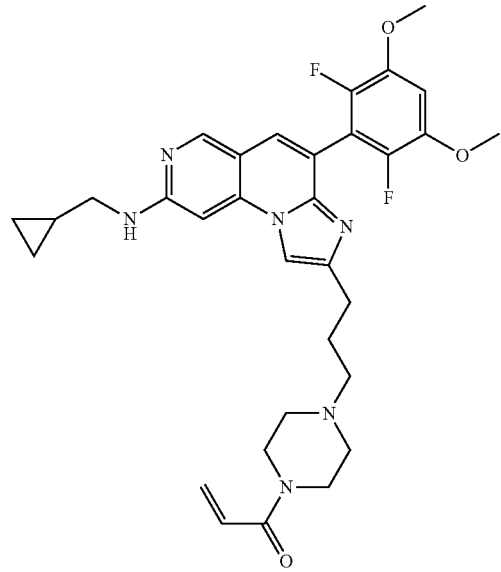

85
-continued
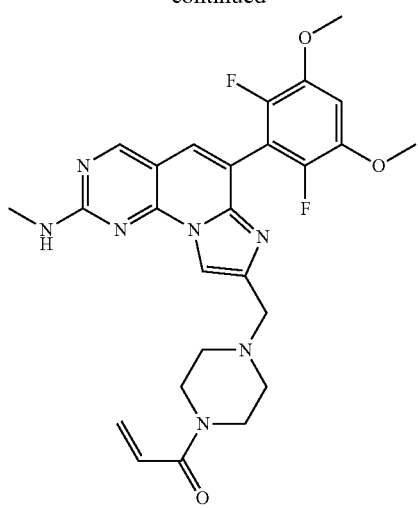
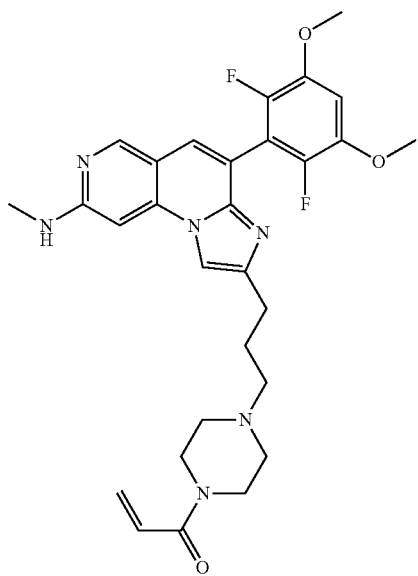
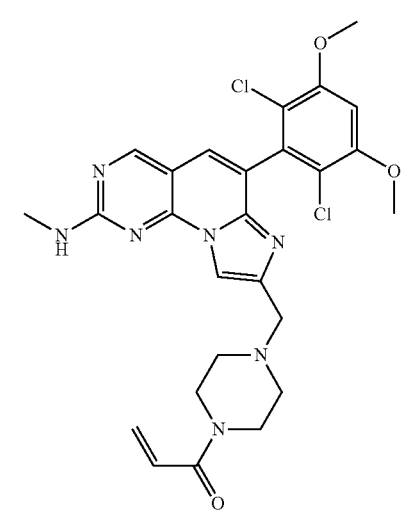
86
-continued
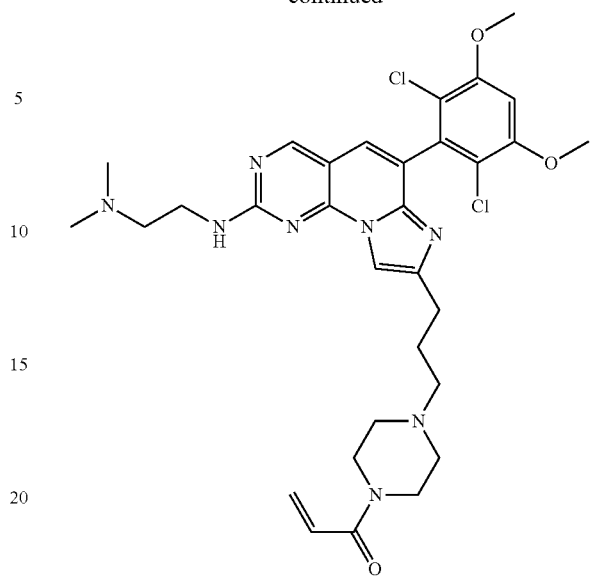
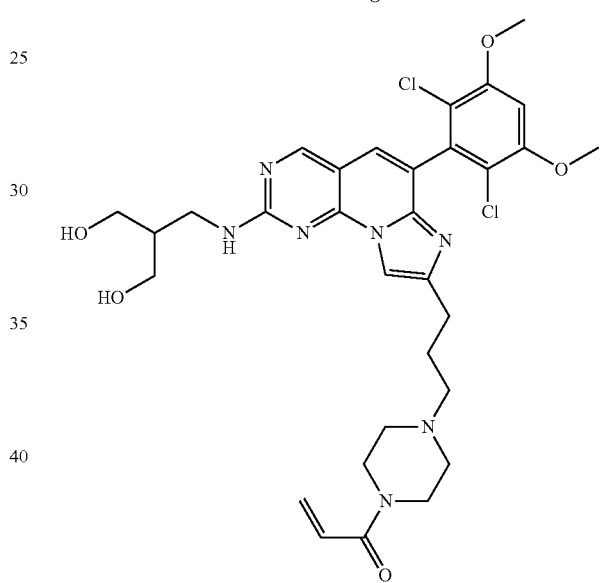
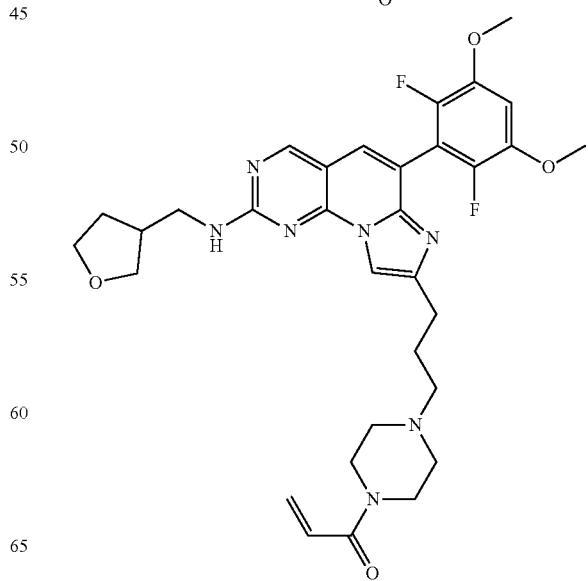

87
-continued
88
-continued
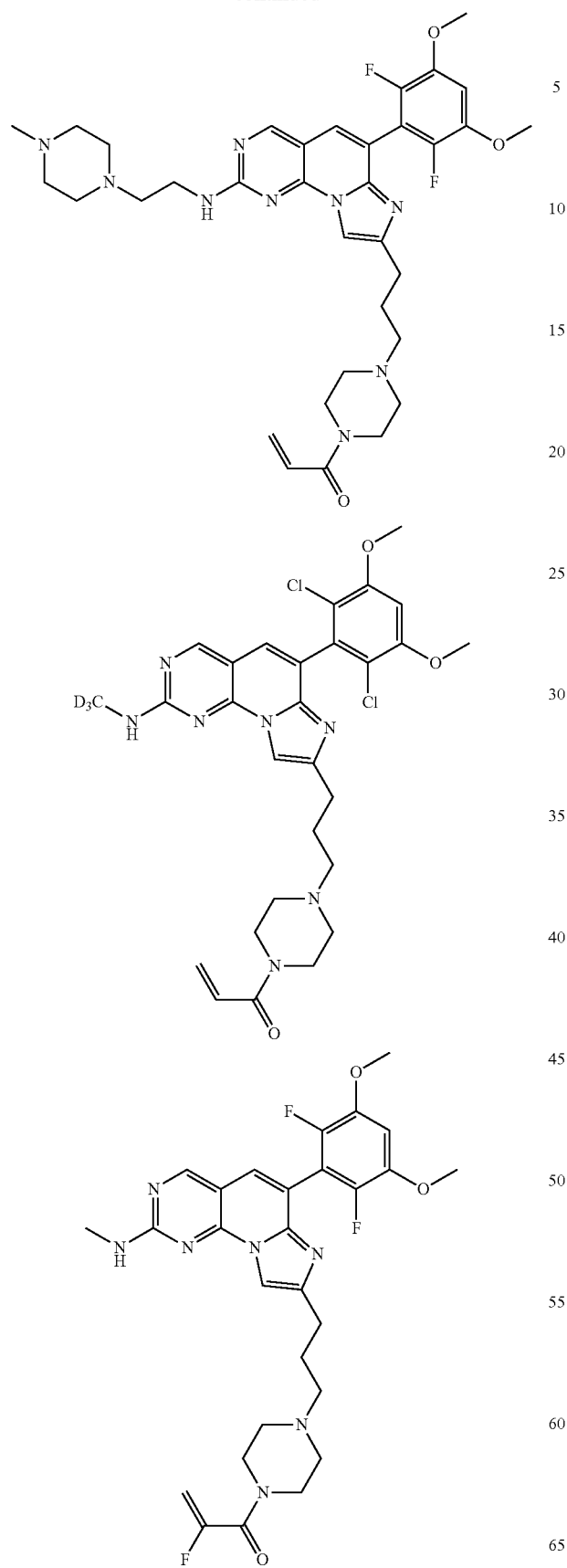
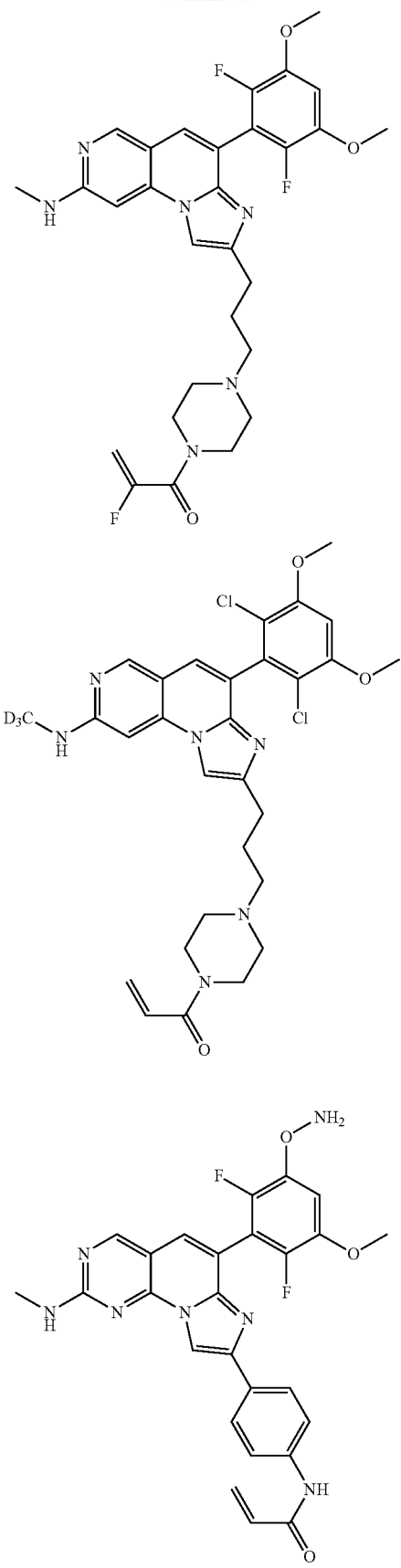

89
-continued
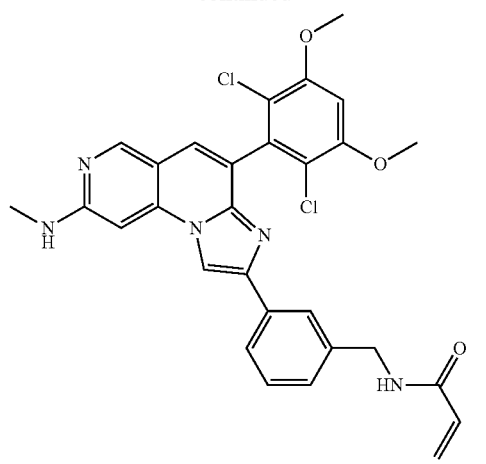
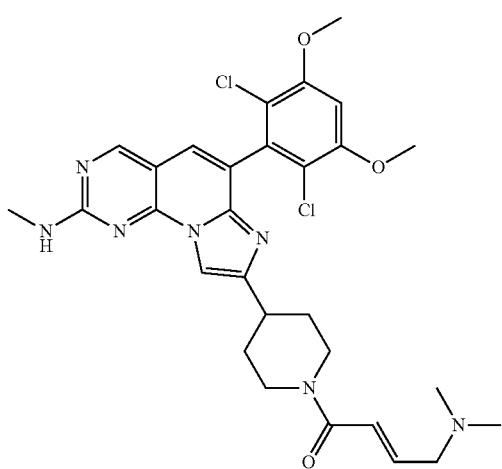
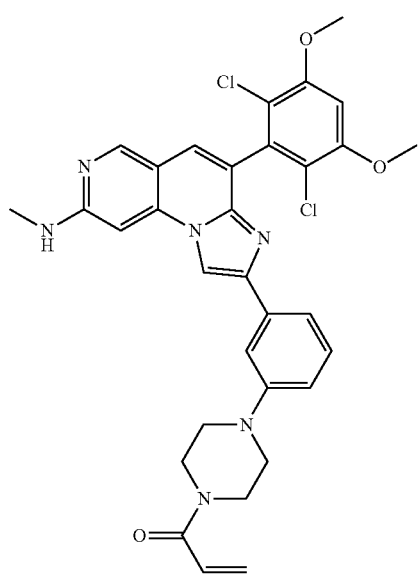
90
-continued
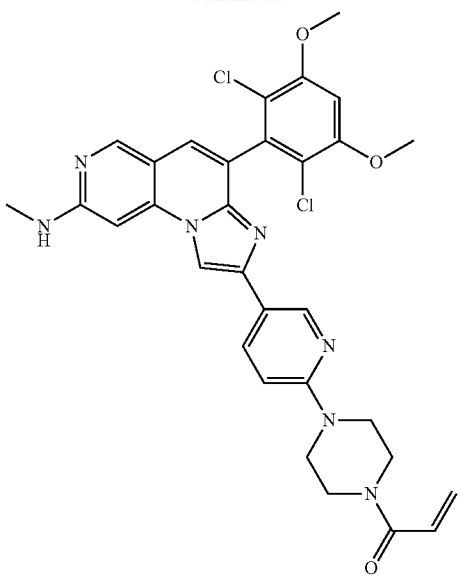
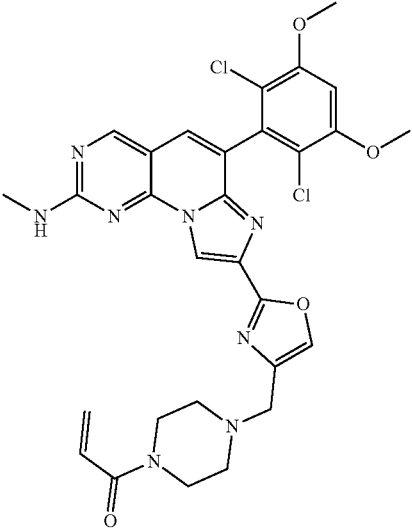

91
-continued
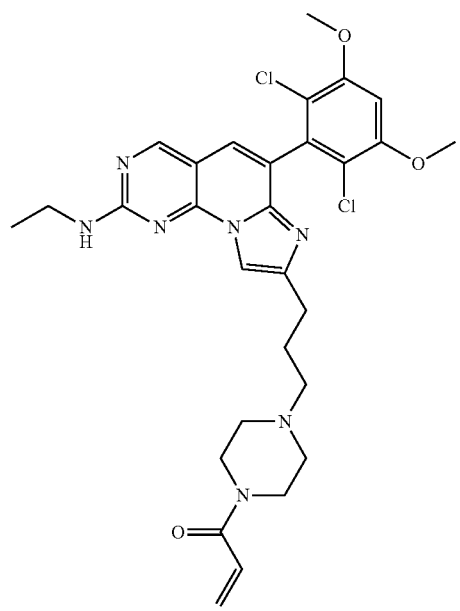
92
-continued
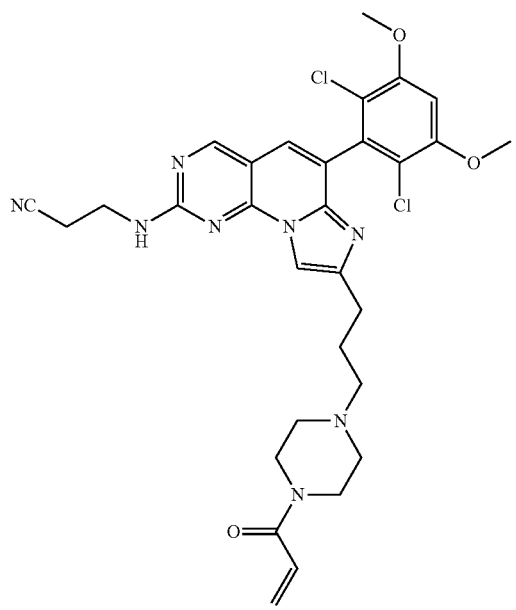
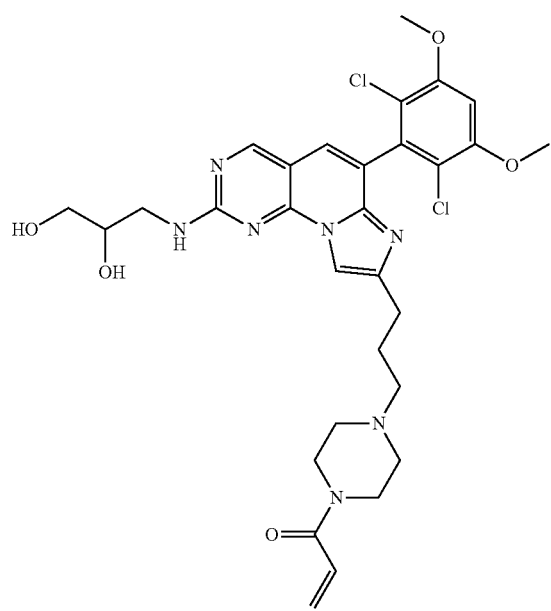
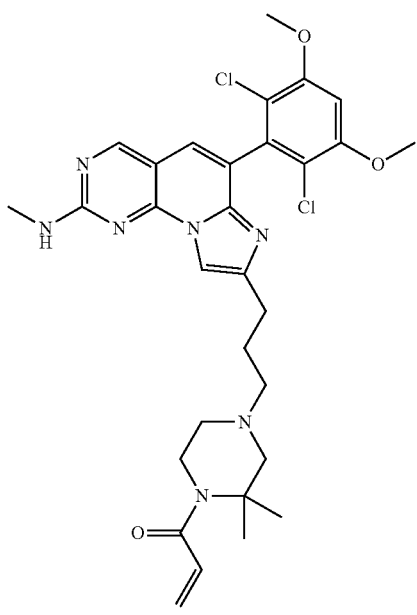

93
-continued
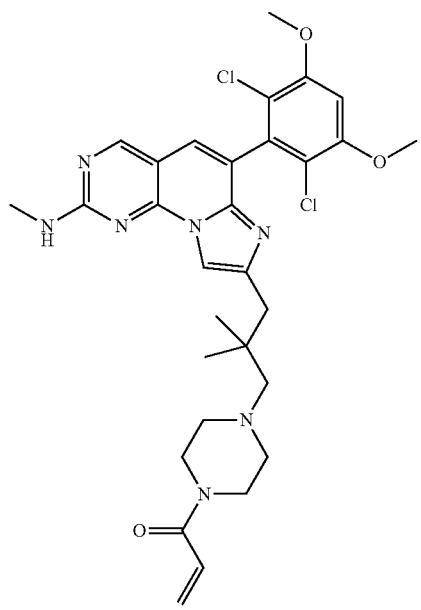
94
-continued
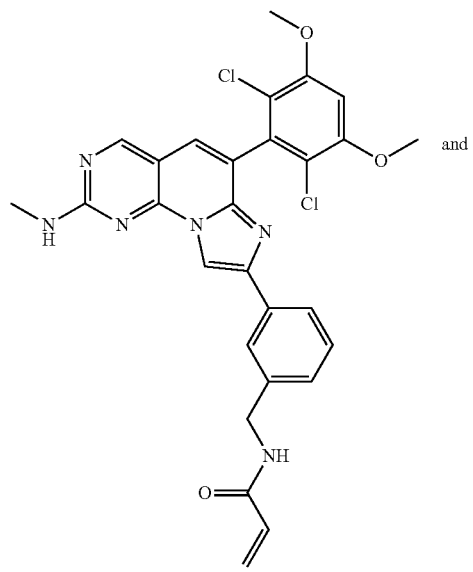
and
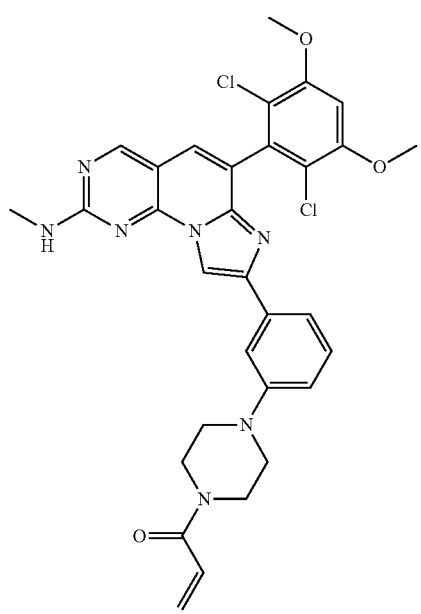
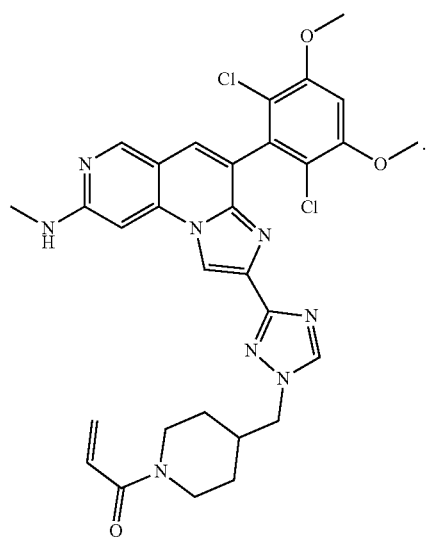

7. A preparation method of the compound represented by formula (I) as defined in claim 1, comprising the following steps:
   a) conducting a condensation reaction with a compound represent by formula (A) and an α-halocarbonyl compound or an equivalent thereof in the presence of an acid or a base to prepare a compound represented by formula (B); and
   b) conducting a substitution reaction or coupling reaction with the compound represented by formula (B) and an amine compound in the presence of an acid, a base or a transition metal catalyst to prepare a compound represented by formula (C); and
   c) conducting a condensation reaction with the compound represented by formula (C) and an acrylic acid or acryloyl chloride compound in the presence of a base or a condensation reagent to prepare the compound represented by formula (I);

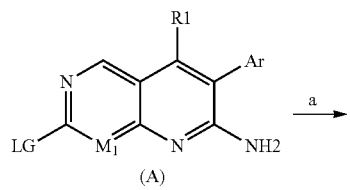
(A)

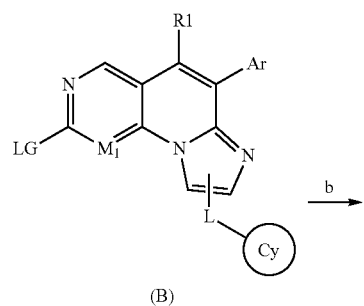
(B)

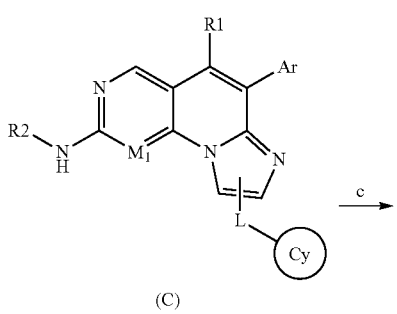
(C)

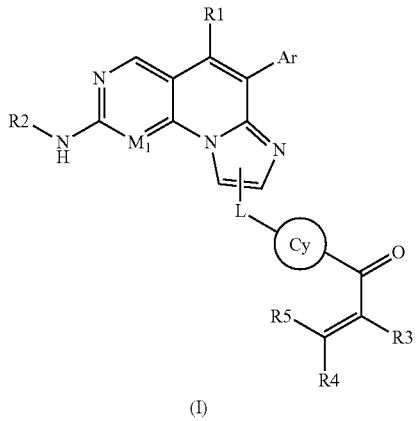
(I)

in each of the formulas, LG is halogen, sulfuryl, sulfinyl, or sulfonate ester group, and other groups are as defined in claim 1.

8. A pharmaceutical composition comprising a therapeutically effective amount of the compound represented by formula (I), or the pharmaceutically acceptable salt thereof, or the enantiomer, diastereomer, or tautomer thereof as defined in claim 1, and at least one pharmaceutical excipient.

9. A method of inhibiting FGFR kinase in a subject in need thereof, comprising administering a therapeutically effective amount of the compound represented by formula (I), or the pharmaceutically acceptable salt thereof, or the enantiomer, diastereomer, or tautomer thereof as defined in claim 1 to the subject.

10. The compound represented by formula (I), or the pharmaceutically acceptable salt thereof, or the enantiomer, diastereomer, or tautomer thereof according to claim 2, wherein,
   in the definition of $R_2$, the 5-8 membered aryl or heteroaryl is pyridinyl;
   and/or, in the definition of $R_2$, the 4-6 membered cycloalkyl or heterocycloalkyl is cyclopropyl, tetrahydrofuryl, piperazinyl, piperidinyl or tetrahydropyrrolyl;
   and/or, $R_3$ is hydrogen or fluorine, and $R_4$ and $R_5$ are hydrogen;
   and/or, in the definition of Ar, one or more hydrogen atoms in the phenyl are substituted by the substituent independently selected from the group consisting of halogen, cyano, $C_1$-$C_8$ alkyl, $C_1$-$C_8$ alkoxyl, amino, hydroxyl, $C_2$-$C_6$ acyl or sulfonyl;
   and/or, in the definition of A, the 5-6 membered heterocycloalkyl is piperazinyl, piperidinyl or tetrahydropyrrolyl;
   and/or, in the definition of A, the 5-6 membered heteroaryl is pyridinyl, oxazolyl or triazolyl;
   and/or, the two substituents on A are located in meta or para-position with respect to each other.

11. The compound represented by formula (I), or the pharmaceutically acceptable salt thereof, or the enantiomer, diastereomer, or tautomer thereof according to claim 10, wherein,
   in the definition of $R_2$, the pyridinyl is further substituted by one 6 membered heterocycloalkyl;
   and/or, in the definition of $R_2$, the cyclopropyl, tetrahydrofuryl, piperazinyl, piperidinyl or tetrahydropyrrolyl is further substituted by $C_1$-$C_6$ alkyl or amino;
   and/or, in the definition of Ar, the phenyl is substituted by two halogens and two $C_1$-$C_8$ alkoxyls.

12. The compound represented by formula (I), or the pharmaceutically acceptable salt thereof, or the enantiomer, diastereomer, or tautomer thereof according to claim 4, wherein ring B is benzene ring, pyridine ring, oxazole ring or triazole ring.

13. The compound represented by formula (I), or the pharmaceutically acceptable salt thereof, or the enantiomer, diastereomer, or tautomer thereof according to claim 1, wherein the compound represented by formula (I) has a structure of:

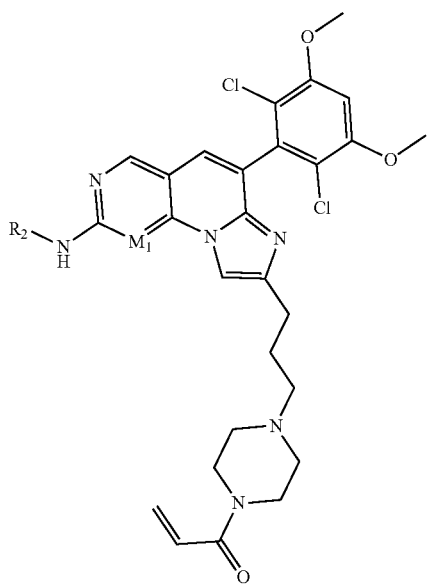

wherein $M_1$ and $R_2$ are as defined in claim 1.

14. The compound represented by formula (I), or the pharmaceutically acceptable salt thereof, or the enantiomer, diastereomer, or tautomer thereof according to claim 1, wherein the compound represented by formula (I) has a structure of

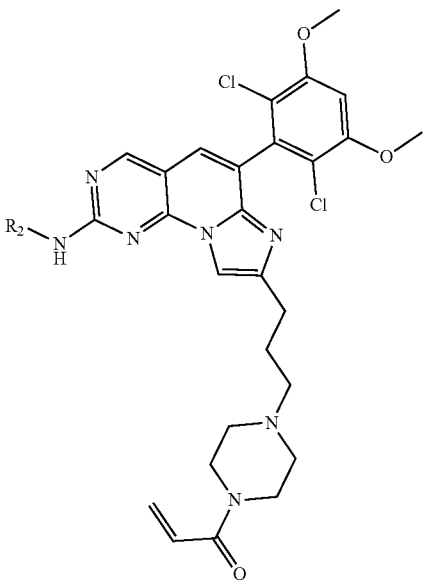

wherein $R_2$ is as defined in claim 1.

15. A method of treating a tumor in a subject in need thereof, comprising administering a therapeutically effective amount of the compound represented by formula (I), or the pharmaceutically acceptable salt thereof, or the enantiomer, diastereomer, or tautomer thereof as defined in claim 1 to the subject.

16. The method according to claim 15, wherein the tumor is non-small cell lung cancer, small cell lung cancer, lung adenocarcinoma, squamous cell lung cancer, breast cancer, prostate cancer, liver cancer, skin cancer, gastric cancer, epithelial cell cancer, gastrointestinal stromal tumor, intestinal cancer, bile duct cancer, gallbladder cancer, colorectal cancer, brain cancer, leukemia, lymphoma, nasopharyngeal cancer, bladder cancer, pancreatic cancer.

17. The method according to claim 16, wherein the tumor is liver cancer or bile duct cancer.

* * * * *